(12) United States Patent
Jaimovich et al.

(10) Patent No.: US 11,939,636 B2
(45) Date of Patent: Mar. 26, 2024

(54) METHODS AND SYSTEMS FOR IMPROVING PATIENT MONITORING AFTER SURGERY

(71) Applicant: GUARDANT HEALTH, INC., Redwood City, CA (US)

(72) Inventors: Ariel Jaimovich, Redwood City, CA (US); Yupeng He, Redwood City, CA (US); Oscar Westesson, Berkeley, CA (US); William J. Greenleaf, Menlo Park, CA (US)

(73) Assignee: Guardant Health, Inc., Palo Alto, CA (US)

( * ) Notice: Subject to any disclaimer, the term of this patent is extended or adjusted under 35 U.S.C. 154(b) by 0 days.

(21) Appl. No.: 16/889,659

(22) Filed: Jun. 1, 2020

(65) Prior Publication Data

US 2021/0017605 A1    Jan. 21, 2021

Related U.S. Application Data

(60) Provisional application No. 62/855,736, filed on May 31, 2019.

(51) Int. Cl.
  *C12Q 1/6886* (2018.01)

(52) U.S. Cl.
  CPC ...... *C12Q 1/6886* (2013.01); *C12Q 2600/112* (2013.01); *C12Q 2600/156* (2013.01); *C12Q 2600/158* (2013.01)

(58) Field of Classification Search
  None
  See application file for complete search history.

(56) References Cited

U.S. PATENT DOCUMENTS

| | | |
|---|---|---|
| 5,912,148 A | 6/1999 | Eggerding |
| 6,130,073 A | 10/2000 | Eggerding |
| 6,210,891 B1 | 4/2001 | Nyren et al. |
| 6,258,568 B1 | 7/2001 | Nyren |
| 6,582,908 B2 | 6/2003 | Fodor et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 7,537,898 B2 | 5/2009 | Bost et al. |
| 9,598,731 B2 | 3/2017 | Talasaz |
| 9,902,992 B2 | 2/2018 | Talasaz et al. |
| 2001/0053519 A1 | 12/2001 | Fodor et al. |
| 2003/0152490 A1 | 8/2003 | Trulson et al. |
| 2011/0160078 A1 | 6/2011 | Fodor et al. |
| 2013/0325360 A1* | 12/2013 | Deciu ............... G16B 30/10 702/20 |
| 2014/0296081 A1 | 10/2014 | Diehn et al. |
| 2016/0032396 A1 | 2/2016 | Diehn et al. |
| 2017/0211143 A1 | 7/2017 | Shendure et al. |
| 2018/0251848 A1 | 9/2018 | Diehn et al. |

FOREIGN PATENT DOCUMENTS

| | | |
|---|---|---|
| WO | 2008063655 A2 | 5/2008 |
| WO | 2014039556 A1 | 3/2014 |
| WO | 2014151117 A1 | 9/2014 |
| WO | 2016040901 A1 | 3/2016 |
| WO | 2016187030 A1 | 11/2016 |
| WO | 2018009723 A1 | 1/2018 |
| WO | 2018119452 A2 | 6/2018 |
| WO | 2020160414 A1 | 8/2020 |

OTHER PUBLICATIONS

Ehrlich et al. (2002 Oncogene vol. 21 p. 5400) (Year: 2002).*
Abbosh, C et al. "Phylogenetic ctDNA analysis depicts early-stage lung cancer evolution" Nature (2017) 545 (7655):446-451.
Anonymous "Seeing beyond the limit: Detect residual disease and asses treatment response" Natera Signatera 2019.
Anonymous: "Fractionation of Differentially Methylated Regions with the MethylMiner(TM) Methylated DNA Enrichment Kit and Deep Sequencing with the SOLiD(TM) System" (2009), pp. 1-8, XP055724166, Retrieved from the Internet: URL:http://tools.thermofisher.com/content/sfs/brochures/cms_074154.pdf.
Anonymous: "TruSeq DNA Methylation Library Preparation Guide" (2014), pp. 1-20, XP055283756, Retrieved from the Internet: URL:http://support.illumina.com/content/dam/illumina-support/documents/documentation/chemistry_documentation/samplepreps_truseq/truseq-dna-methylation/truseq-dna-methylation-library-prep-guide-15066014-a.pdf.

(Continued)

*Primary Examiner* — Katherine D Salmon
(74) *Attorney, Agent, or Firm* — Indhu Kanakaraj

(57) ABSTRACT

In an aspect, a method for detecting the presence or absence of cancer in a subject comprises: (a) obtaining samples from the subject from different time points, wherein a first sample obtained at first time point is a polynucleotide sample from a tumor tissue specimen and a second sample obtained at second time point is a cell-free polynucleotide sample from a blood sample; (b) processing polynucleotides from each of the samples, comprising: i) tagging at least a portion of the polynucleotides, thereby generating tagged parent polynucleotides; ii) amplifying at least a portion of the tagged parent polynucleotides to generate progeny polynucleotides; iii) enriching at least a portion of the progeny polynucleotides for target genomic regions; thereby generating enriched polynucleotides; and iv) sequencing at least a portion of the enriched polynucleotides to generate sequencing reads; and (c) analyzing genomic regions for at least one epigenetic feature from the sequencing reads.

15 Claims, 8 Drawing Sheets

(56) References Cited

OTHER PUBLICATIONS

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.
Belinsky, S.A. "Unmasking the lung cancer epigenome" Annu. Rev. Physiol. (2015) 77:453-474.
Cock, PJA, et al. "The Sanger FASTQ file format for sequences with quality scores, and the Solexa/Illumina FASTQ variants" NAR (2009) 38(6):1767-1771.
Cuddapah, S. et al. "Global analysis of the insulator binding protein CTCF in chromatin barrier regions reveals demarcation of active and repressive domains" Genome Res (2009) 19:24-32.
Danecek, P. et al. "The variant call format and VCFtools" Bioinformatics (2011) 27(15):2156-2158.
Decock, A. et al. "Methyl-CpG-binding domain sequencing reveals a prognostic methylation signature in neuroblastoma for the Children's Cancer and leukemia Group (CCLG)", Oncotarget, (2016) 7:1960-1972, XP055477850, Retrieved from the Internet: URL:https://www.ncbi.nlm.nih.gov/pmc/articles/PMC4811509/pdf/oncotarget-07-1960.pdf.
Ehrlich, M. "DNA hypomethylation in cancer cells" Epigenomics 1:239-259.
Furonaka, O. et al. "Aberrant methylation and loss of expression of O6-methylguanine-DNA methyltransferase in pulmonary squamous cell carcinoma and adenocarcinoma" Pathol Int (2005) 55:303-309.
Gai, W. et al. "Epigenetic Biomarkers in Cell-Free DNA and Applications in Liquid Biopsy" Genes (2019) 10(1):32 (14 pages).
Gomes, A. et al. "Promoter hypermethylation of DNA repair genes MLH1 and MSH2 in adenocarcinomas and squamous cell carcinomas of the lung" Rev. Port. Pneumol. (2014) 20:20-30.
Guo, M. et al. "Hypermethylation of the GATA genes in lung cancer" Clin Cancer Res (2004) 10(23):7917-7924.
Guo, Y.A. et al. "Mutation hotspots at CTCF binding sites coupled to chromosomal instability in gastrointestinal cancers" Nature Commun (2018) 9:1520.
Heller, G. et al. "Expression and methylation pattern of TSLC1 cascade genes in lung carcinomas" Oncogene (2006) 25:959-968.
Hon, G.C. et al. "Global DNA hypomethylation coupled to repressive chromatin domain formation and gene silencing in breast cancer" Genome Res (2012) 22:246-258.
Hopkins-Donaldson, S. et al. "Silencing of death receptor and caspase-8 expression in small cell lung carcinoma cell lines and tumors by DNA methylation" Cell Death Differ. (2003) 10:356-64.
Hulbert, A. et al. "Early Detection of Lung Cancer Using DNA Promoter Hypermethylation in Plasma and Sputum" Clin. Cancer Res. (2017) 23:1998-2005.
International search report and written opinion dated Oct. 20, 2020 for PCT/US2020/035605.
Kang, S. et al. "CancerLocator: non-invasive cancer diagnosis and tissue-of origin prediction using methylation profiles of cell-free DNA" Genome Biology (2017) 18(1):53 XP055682390.
Katainin, R. et al. "CTCF/cohesin-binding sites are frequently mutated in cancer" Nature Genetics (2015) 47:818- 821.
Kikuchi, S. et al. "Promoter Methylation of DAL-1/4.1B Predicts Poor Prognosis in Non Small Cell Lung Cancer" Clin Canc Res (2005) 11:2954-2961.
Kim, D-H. et al. "p16INK4a and Histology-specific Methylation of CpG Islands by Exposure to Tobacco Smoke in Non-Small Cell Lung Cancer" Canc Res (2001) 61:3419-3424.
Kim, D-H. et al. "Promoter methylation of DAP-kinase: association with advanced stage in non-small cell lung cancer" Oncogene. (2001) 20:1765-1770.
Lam, K. et al. "DNA methylation based biomarkers in colorectal cancer: A systematic review" Biochim Biophys Acta (2016 ) 1866(1):106-20.

Levy, S.E. et al. "Advancements in Next-Generation Sequencing" Ann Rev Genomics & Hum Genetics (2016) 17:95-115.
Li, et al., The Sequence Alignment/Map format and SAMtools, Bioinformatics, 2009, 25(16):2078-9.
Li, W. et al. "CancerDetector: ultrasensitive and non-invasive cancer detection at the resolution of individual reads using cell-free DNA methylation sequencing data" Nucleic Acids Research (2018) 46(15):e-89-e89.
Licchesi, J. et al. "Epigenetic alteration of Wnt pathway antagonists in progressive glandular neoplasia of the lung" Carcinogenesis (2008) 29:895-904.
Lissa, D. et al. "Methylation analyses in liquid biopsy" Transl Lung Cancer Res (2016) 5(5):492-504.
Liu, L. et al. "Comparison of Next-Generation Sequencing Systems" J Biomed & Biotech (2012) Article ID251364:1-11.
Liu, Y. et al. "Bisulfite-free direct detection of 5-methylcytosine and 5-hydroxymethylcytosine at base resolution" Nature Biotech (2019) 37(4):424-429.
Maclean, D. et al. "Application of 'next-generation' sequencing technologies to microbial genetics" Nature Rev Microbiol (2009) 7:287-296.
Martin, D. et al. "Genome-wide CTCF distribution in vertebrates defines equivalent sites that aid the identification of disease-associated genes" Nature Structural Mol Bio (2011) 18:708-714.
Noguera Da Costa, A. et al. "Detection of cancer-specific epigenomic changes in bio fluids: Powerful tools in biomarker discovery and application" Mol Oncol (2012) 6(6):704.715.
Doki, A. et al. "A Panel of Novel Detection and Prognostic Methylated DNA Markers in Primary Non-Small Cell Lung Cancer and Serum DNA" (2017) Clin. Cancer Res. 23:7141-7152.
Palmisano, W. et al. "Aberrant Promoter Methylation of the Transcription Factor Genes PAX5 alpha and beta in Human Cancers" Cancer Res (2003) 63:4620-4625.
Parashar, S. et al. "DNA methylation signatures of breast cancer in peripheral T-cells" BMC Cancer (2018) 18(1) XP055723843.
Rhee, H.S. et al. "Comprehensive genome-wide protein-DNA interactions detected at single-nucleotide resolution" Cell (2011) 147:1408-1419.
Schutsky, E.K. et al., "Nondestructive, base-resolution sequencing of 5-hydroxymethylcytosine using a DNA deaminase" Nature Biotech (2018); 36:1083-1090.
Shi, Y-X et al. "Genome-wide DNA methylation profiling reveals novel epigenetic signatures in squamous cell lung cancer" BMC Genomics (2017) 18:901.
Skvortsova, T.E. et al. "Cell-free and cell-bound circulating DNA in breast tumours: DNA quantification and analysis of tumour-related gene methylation" Br J Cancer (2006) 94(10):1492-1495.
Snyder, M.W. et al. "Cell-free DNA Comprises an In Vivo Nucleosome Footprint that Informs Its Tissues-Of-Origin" Cell (2016) 164:57-68 & Supplemental Information.
Song, C-X. et al. "Selective chemical labeling reveals the genome-wide distribution of 5-hydroxymethylcytosine" Nature Biotech (2011) 29:68-72.
Stewart, C.M. et al. "Circulating cell-free DNA for non-invasive cancer management" Cancer Genetics (2018) 228-229:169-179.
Toyooka, K.O. et al. "Loss of Expression and Aberrant Methylation of the CDH13 (H-Cadherin) Gene in Breast and Lung Carcinomas" Cancer Res. (2001) 61:4556-4560.
Voelkerding, K.V. et al. "Next-generation sequencing: from basic research to diagnostics" Clin Chem (2009) 55:641-658.
Warton, K. et al. "Methylated circulating tumor DNA in blood: power in cancer prognosis and response" Endocrine-Related Cancer (2016) 23(3):R157-R171.
Yamashita, R. et al. "DBTSS: DataBase of Human Transcription Start Sites, progress report 2006" Nucleic Acids Res. (2006) 34(Database issue): D86-D89.
Yu, M. et al. "Base-Resolution Analysis of 5-Hydroxymethylcytosine in the Mammalian Genome" Cell (2012) 149 (6):1368-1380.

\* cited by examiner

METHODS AND SYSTEMS FOR IMPROVING PATIENT MONITORING AFTER SURGERY

CROSS-REFERENCE TO RELATED APPLICATIONS

This application claims the benefit of priority to U.S. Provisional Patent Application No. 62/855,736, filed May 31, 2019, which is incorporated by reference herein for all purposes.

BACKGROUND

Current methods of cancer diagnostic assays of cell-free nucleic acids (e.g., cell-free DNA or cell-free RNA) may focus on the detection of tumor-related somatic variants, including single nucleotide variants (SNVs), copy number variations (CNVs), fusions, and indels (i.e., insertions or deletions), which are all mainstream targets for liquid biopsy. There is growing evidence that non-sequence modifications like methylation status and fragment termini distribution patterns in cell-free DNA can provide information on the source of cell-free DNA and disease level. The non-sequence modifications of the cell-free DNA, when combined with somatic mutation calling, can yield a more comprehensive assessment of tumor status than that available from either approach alone.

SUMMARY

The present disclosure provides methods and systems for detecting a presence or absence of cancer in a subject based on analysis of genomic regions for epigenetic features from sequencing reads of samples. In some embodiments, the samples are obtained from a subject from at least two different time points.

In an aspect, the present disclosure provides a method for detecting a presence or absence of cancer in a subject, comprising: a) obtaining at least one sample from the subject from at least two different time points to provide at least two samples, wherein a first sample of the at least two samples is obtained at a first time point of the at least two different time points and a second sample of the at least two samples is obtained at a second time point of the at least two different time points; b) processing polynucleotides from each of the at least two samples, wherein the processing comprises: i. tagging at least a portion of the polynucleotides, thereby generating tagged parent polynucleotides; ii. amplifying at least a portion of the tagged parent polynucleotides to generate progeny polynucleotides; iii. enriching at least a portion of the progeny polynucleotides for target genomic regions, thereby generating enriched polynucleotides; and iv. sequencing at least a portion of the enriched polynucleotides to generate a set of sequencing reads; and c) analyzing a plurality of genomic regions for at least one epigenetic feature from the set of sequencing reads of the at least two samples, to detect the presence or absence of the cancer in the subject at the second time point.

In some embodiments, the processing further comprises, prior to the tagging, partitioning at least a portion of the polynucleotides into at least two partitions based on at least one epigenetic feature, thereby generating partitioned polynucleotides.

In another aspect, the present disclosure provides a method for detecting a presence or absence of cancer in a subject, comprising: a) obtaining at least one sample from the subject from at least two different time points to provide at least two samples, wherein a first sample of the at least two samples is obtained at a first time point of the at least two different time points and a second sample of the at least two samples is obtained at a second time point of the at least two different time points; b) processing polynucleotides from each of the at least two samples, wherein the processing comprises: i. partitioning at least a portion of the polynucleotides into at least two partitions based on at least one epigenetic feature, thereby generating partitioned polynucleotides; ii. tagging at least a portion of the partitioned polynucleotides, thereby generating tagged parent polynucleotides; amplifying at least a portion of the tagged parent polynucleotides to generate progeny polynucleotides; and iv. sequencing at least a portion of the progeny polynucleotides to generate a set of sequencing reads; and c) analyzing a plurality of genomic regions for at least one epigenetic feature from the set of sequencing reads of the at least two samples, to detect the presence or absence of the cancer in the subject at the second time point.

In some embodiments, the first sample is a polynucleotide sample extracted from a tumor tissue specimen, and wherein the second sample is a cell-free polynucleotide sample extracted from a blood sample. In some embodiments, the first sample of the at least two samples obtained at the first time point of the at least two different time points is a cell-free polynucleotide sample extracted from a blood sample, and wherein the second sample of the at least two samples obtained at the second time point of the at least two different time points is a cell-free polynucleotide sample extracted from a blood sample.

In some embodiments, the analyzing comprises: i. mapping the set of sequencing reads to a reference sequence; ii. determining a plurality of epigenetic rates for the plurality of genomic regions of the at least two samples; iii. adjusting an epigenetic rate threshold based on an epigenetic rate of at least one of the plurality of genomic regions of the first sample; and iv. comparing the epigenetic rate for the plurality of genomic regions of the second sample with the adjusted epigenetic rate threshold.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold, or (b) as negative for ctDNA, if the epigenetic rates of the plurality of genomic regions of the second sample are all less than the adjusted epigenetic rate threshold. In some embodiments, the method further comprises analyzing the plurality of genomic regions from the set of sequencing reads of the at least two samples to detect a presence or absence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold or the presence of the at least one somatic variation is detected in the second sample, or (b) as negative for ctDNA, if the epigenetic rates of the plurality of genomic regions of the second sample are all less than the adjusted epigenetic rate threshold and the presence of the at least one somatic variation is not detected in the second sample.

In some embodiments, the analyzing comprises: i. mapping the set of sequencing reads to a reference sequence; ii. determining a plurality of epigenetic rates for the plurality of genomic regions of the first sample; iii. determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample; iv. combining the plurality of likelihoods for one of more the plurality of genomic regions to determine an overall posterior probability for the presence of the cancer in the subject; and v. comparing the overall posterior probability for the presence of the cancer in the subject with a predetermined threshold.

In some embodiments, the method further comprises vi. classifying the subject (a) as positive for circulating tumor DNA (ctDNA), if the overall posterior probability for the presence of the cancer in the subject is greater than or equal to the predetermined threshold, or (b) as negative for ctDNA, if the overall posterior probability for the presence of the cancer in the subject is less than the predetermined threshold.

In some embodiments, the method further comprises analyzing the plurality of genomic regions from the set of sequencing reads of the at least two samples to detect the presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises vi. classifying the subject (a) as positive for circulating tumor DNA (ctDNA), if the overall posterior probability for the presence of the cancer in the subject is greater than or equal to the predetermined threshold or the presence of the at least one somatic variation is detected in the second sample, or (b) as negative for ctDNA, if the overall posterior probability for the presence of the cancer in the subject is less than the predetermined threshold and the presence of the at least one somatic variation is not detected in the second sample.

In another aspect, the present disclosure provides a method for detecting a presence or absence of cancer in a subject, comprising: a) obtaining at least one set of sequencing reads from at least one sample collected from the subject from at least two different time points to provide at least two sets of sequencing reads, wherein a first set of sequencing reads of the at least two sets of sequencing reads is obtained from a first sample of the at least two samples collected at a first time point of the at least two different time points, and a second set of sequencing reads of the at least two sets of sequencing reads is obtained from a second sample of the at least two samples collected at a second time point of the at least two different time points; and b) analyzing a plurality of genomic regions for at least one epigenetic feature from the at least two sets of sequencing reads to detect the presence of the cancer in the subject at the second time point.

In some embodiments, the analyzing comprises: i. mapping the at least two sets of sequencing reads to a reference sequence; ii. determining a plurality of epigenetic rates for the plurality of genomic regions of the at least two samples; iii. adjusting an epigenetic rate threshold based on an epigenetic rate of at least one of the plurality of genomic regions of the first sample; and iv. comparing the epigenetic rate for the plurality of genomic regions of the second sample with the adjusted epigenetic rate threshold.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold, or (b) as negative for ctDNA, if the epigenetic rates of the plurality of genomic regions of the second sample are all less than the adjusted epigenetic rate threshold. In some embodiments, the method further comprises analyzing the plurality of genomic regions from the set of sequencing reads of the at least two samples to detect a presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold or the presence of the at least one somatic variation is detected in the second sample, or (b) as negative for ctDNA, if the epigenetic rates of the plurality of genomic regions of the second sample are all less than the adjusted epigenetic rate threshold and the presence of the at least one somatic variation is not detected in the second sample.

In some embodiments, the analyzing comprises: i. mapping the at least two sets of sequencing reads to a reference sequence; ii. determining a plurality of epigenetic rates for the plurality of genomic regions of the first sample; iii. determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample; iv. combining the plurality of likelihoods for the plurality of genomic regions to determine an overall posterior probability for the presence of the cancer in the subject; and v. comparing the overall posterior probability for the presence of the cancer in the subject with a predetermined threshold.

In some embodiments, the method further comprises vi. classifying the subject (a) as positive for circulating tumor DNA (ctDNA), if the overall posterior probability for the presence of the cancer in the subject is greater than the predetermined threshold, or (b) as negative for ctDNA, if the overall posterior probability for the presence of the cancer in the subject is less than the predetermined threshold. In some embodiments, the method further comprises analyzing the plurality of genomic regions from the set of sequencing reads of the at least two samples to detect the presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises vi. classifying the subject (a) as positive for circulating tumor DNA (ctDNA), if the overall posterior probability for the presence of the cancer in the subject is greater than or equal to the predetermined threshold or the presence of the at least one somatic variation is detected in the second sample, or (b) as negative for ctDNA, if the overall posterior probability for the presence of the cancer in the subject is less than the predetermined threshold and the presence of the at least one somatic variation is not detected in the second sample.

In some embodiments, the at least one epigenetic feature comprises a methylation status, a nucleosomal position, a position of DNA binding proteins, and/or a fragmentomic signal of at least one of the plurality of genomic regions. In some embodiments, the at least one epigenetic feature comprises the methylation status. In some embodiments, the at least one epigenetic rate comprises a methylation rate. In some embodiments, the at least one epigenetic feature comprises the position of DNA binding proteins. In some embodiments, the DNA binding proteins comprise histones, transcription factors, or CCCTC-binding factor (CTCF) proteins. In some embodiments, the at least one epigenetic feature comprises the fragmentomic signal. In some embodiments, the fragmentomic signal comprises a length of the polynucleotides and/or a start position and an end position of the polynucleotides. In some embodiments, the fragmentomic signal comprises a length of the polynucleotides for a blood sample and a nucleosomal position for the polynucleotides of a tissue sample. In some embodiments, the nucleosomal position is determined by chromatin immunoprecipitation sequencing (ChIP-Seq).

In some embodiments, the tagging comprises attaching a set of tags to at least the portion of the partitioned polynucleotides to generate the tagged parent polynucleotides, wherein each of the tagged parent polynucleotides comprises one or more tags from among the set of tags.

In some embodiments, each tag from among the set of tags comprises at least one barcode from among a plurality of barcodes. In some embodiments, the plurality of barcodes comprises 5 to 150 barcodes. In some embodiments, a given barcode of the plurality of barcodes has a length of at least 5 base pairs (bp).

In some embodiments, the method further comprises, prior to the sequencing, amplifying at least a portion of the enriched polynucleotides. In some embodiments, the amplifying, performed prior to the enriching or prior to the sequencing, comprises using primers comprising a sample index to enable multiplex sequencing.

In some embodiments, the sequencing comprises next-generation sequencing. In some embodiments, the sequencing comprises bisulfite sequencing. In some embodiments, the sequencing comprises bisulfite-free methylation sequencing. In some embodiments, the bisulfite-free methylation sequencing comprises TET-assisted pyridine borane sequencing (TAPS), APOBEC-coupled epigenetic sequencing (ACE-seq), TET-assisted bisulfite sequencing (TAB-seq), or selective chemical labeling and enrichment of hydroxymethyl cytosine (hmC-Seal).

In some embodiments, each of the plurality of genomic regions comprises at least 1 base pair (bp), at least 2 bp, at least 5 bp, at least 10 bp, at least 20 bp, at least 50 bp, at least 100 bp, at least 200 bp, at least 500 bp, at least 1000 bp, at least 2000 bp, at least 5000 bp, at least 10,000 bp, at least 20,000 bp, at least 50,000 bp, at least 100,000 bp, at least 200,000 bp, at least 500,000 bp, or at least 1,000,000 bp.

In another aspect, the present disclosure provides a system comprising a controller comprising, or capable of accessing, computer readable media comprising non-transitory computer-executable instructions which, when executed by at least one electronic processor, perform a method for detecting a presence or absence of cancer in a subject, the method comprising: a) directing the obtaining of at least one sample from the subject from at least two different time points to provide at least two samples, wherein a first sample of the at least two samples is obtained at a first time point of the at least two different time points and a second sample of the at least two samples is obtained at a second time point of the at least two different time points; b) directing the processing of polynucleotides from each of the at least two samples, wherein the processing comprises: i. tagging at least a portion of the polynucleotides, thereby generating tagged parent polynucleotides; ii. amplifying at least a portion of the tagged parent polynucleotides to generate progeny polynucleotides; enriching at least a portion of the progeny polynucleotides for target genomic regions, thereby generating enriched polynucleotides; and iv. sequencing at least a portion of the enriched polynucleotides to generate a set of sequencing reads; and c) analyzing a plurality of genomic regions for at least one epigenetic feature from the set of sequencing reads of the at least two samples, to detect the presence or absence of the cancer in the subject at the second time point.

In some embodiments, the processing further comprises, prior to the tagging, partitioning at least a portion of the polynucleotides into at least two partitions based on at least one epigenetic feature, thereby generating partitioned polynucleotides.

In another aspect, the present disclosure provides a system comprising a controller comprising, or capable of accessing, computer readable media comprising non-transitory computer-executable instructions which, when executed by at least one electronic processor, perform a method for detecting a presence or absence of cancer in a subject, the method comprising: a) directing the obtaining of at least one sample from the subject from at least two different time points to provide at least two samples, wherein a first sample of the at least two samples is obtained at a first time point of the at least two different time points and a second sample of the at least two samples is obtained at a second time point of the at least two different time points; b) directing the processing of polynucleotides from each of the at least two samples, wherein the processing comprises: i. partitioning at least a portion of the polynucleotides into at least two partitions based on at least one epigenetic feature, thereby generating partitioned polynucleotides; ii. tagging at least a portion of the partitioned polynucleotides, thereby generating tagged parent polynucleotides; iii. amplifying at least a portion of the tagged parent polynucleotides to generate progeny polynucleotides; and iv. sequencing at least a portion of the progeny polynucleotides to generate a set of sequencing reads; and c) analyzing a plurality of genomic regions for at least one epigenetic feature from the set of sequencing reads of the at least two samples, to detect the presence or absence of the cancer in the subject at the second time point.

In some embodiments, the first sample is a polynucleotide sample extracted from a tumor tissue specimen, and wherein the second sample is a cell-free polynucleotide sample extracted from a blood sample. In some embodiments, the first sample is a cell-free polynucleotide sample extracted from a blood sample, and wherein the second sample is a cell-free polynucleotide sample extracted from a blood sample.

In some embodiments, the analyzing comprises: i. mapping the set of sequencing reads to a reference sequence; ii. determining a plurality of epigenetic rates for the plurality of genomic regions of the at least two samples; iii. adjusting an epigenetic rate threshold based on an epigenetic rate of at least one of the plurality of genomic regions of the first sample; and iv. comparing the epigenetic rate for the plurality of genomic regions of the second sample with the adjusted epigenetic rate threshold.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold, or (b) as negative for ctDNA, if the epigenetic rates of the plurality of genomic regions of the second sample are all less than the adjusted epigenetic rate threshold. In some embodiments, the method further comprises analyzing the plurality of genomic regions from the set of sequencing reads of the at least two samples to detect a presence or absence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises v. classifying the subject (a) as positive for circulating tumor DNA (ctDNA), if the epigenetic rate of at least one of the plurality of genomic regions of the second sample is greater than or equal to the epigenetic rate threshold or the presence of the at least one somatic variation is detected in the second sample, or (b) as negative for ctDNA, if the epigenetic rates of the plurality of genomic regions of the second sample are all less than the epigenetic rate threshold and the presence of the at least one somatic variation is not detected in the second sample.

In some embodiments, the analyzing comprises: i. mapping the set of sequencing reads to a reference sequence; ii. determining a plurality of epigenetic rates for the plurality of genomic regions of the first sample; iii. determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample; iv. combining the plurality of likelihoods for the plurality of genomic regions to determine an overall posterior probability for the presence of the cancer in the subject; and v. comparing the overall posterior probability for the presence of the cancer in the subject with a predetermined threshold.

In some embodiments, the method further comprises vi. classifying the subject (a) as positive for circulating tumor DNA (ctDNA), if the overall posterior probability for the presence of the cancer in the subject is greater than or equal to the predetermined threshold, or (b) as negative for ctDNA, if the overall posterior probability for the presence of the cancer in the subject is less than the predetermined threshold. In some embodiments, the method further comprises analyzing the plurality of genomic regions from the set of sequencing reads of the at least two samples to detect the presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises vi. classifying the subject (a) as positive for circulating tumor (ctDNA), if the overall posterior probability for the presence of the cancer in the subject is greater than or equal to the predetermined threshold or the presence of the at least one somatic variation is detected in the second sample, or (b) as negative for ctDNA, if the overall posterior probability for the presence of the cancer in the subject is less than the predetermined threshold and the presence of the at least one somatic variation is not detected in the second sample.

In another aspect, the present disclosure provides a system comprising a controller comprising, or capable of accessing, computer readable media comprising non-transitory computer-executable instructions which, when executed by at least one electronic processor, perform a method for detecting a presence or absence of cancer in a subject, the method comprising: a) directing the obtaining of at least one set of sequencing reads from at least one sample collected from the subject from at least two different time points to provide at least two sets of sequencing reads, wherein a first set of sequencing reads of the at least two sets of sequencing reads is obtained from a first sample of the at least two samples collected at a first time point of the at least two different time points, and a second set of sequencing reads of the at least two sets of sequencing reads is obtained from a second sample of the at least two samples collected at a second time point of the at least two different time points; and b) analyzing a plurality of genomic regions for at least one epigenetic feature from the at least two sets of sequencing reads of the at least two samples to detect the presence of the cancer in the subject at the second time point.

In some embodiments, the analyzing comprises: i. mapping the at least two sets of sequencing reads to a reference sequence; ii. determining a plurality of epigenetic rates for the plurality of genomic regions of the at least two samples; iii. adjusting an epigenetic rate threshold based on an epigenetic rate of at least one of the plurality of genomic regions of the first sample; and iv. comparing the epigenetic rate for the plurality of genomic regions of the second sample with the adjusted epigenetic rate threshold.

In some embodiments, the method further comprises v. classifying the subject (a) as positive for circulating tumor DNA (ctDNA), if the epigenetic rate of at least one of the plurality of genomic regions is greater than or equal to the adjusted epigenetic rate threshold, or (b) as negative for ctDNA, if the epigenetic rates of the plurality of genomic regions are all less than the adjusted epigenetic rate threshold.

In some embodiments, the method further comprises analyzing the plurality of genomic regions from the set of sequencing reads of the at least two samples to detect a presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises v. classifying the subject (a) as positive for circulating tumor DNA (ctDNA), if the epigenetic rate of at least one of the plurality of genomic regions of the second sample is greater than or equal to the adjusted epigenetic rate threshold or the presence of the at least one somatic variation is detected in the second sample, or (b) as negative for ctDNA, if the epigenetic rates of the plurality of genomic regions of the second sample are all less than the adjusted epigenetic rate threshold and the presence of the at least one somatic variation is not detected in the second sample.

In some embodiments, the analyzing comprises: i. mapping the at least two sets of sequencing reads to a reference sequence; ii. determining a plurality of epigenetic rates for the plurality of genomic regions of the first sample; iii. determining a likelihood of a tumor fraction for each of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample; iv. combining the plurality of likelihoods for the plurality of genomic regions to determine an overall posterior probability for the presence of the cancer in the subject; and v. comparing the overall posterior probability for the presence of the cancer in the subject with a predetermined threshold.

In some embodiments, the method further comprises vi. classifying the subject (i) as positive for circulating tumor DNA (ctDNA), if the overall posterior probability for the presence of the cancer in the subject is greater than or equal to the predetermined threshold, or (ii) as negative for ctDNA, if the overall posterior probability for the presence of the cancer in the subject is less than the predetermined threshold. In some embodiments, the method further comprises, analyzing the plurality of genomic regions from the set of sequencing reads of the at least two samples to detect the presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method further comprises vi. classifying the subject (a) as positive for circulating tumor DNA (ctDNA), if the overall posterior probability for the presence of the cancer in the subject is greater than or equal to the predetermined threshold or the presence of the at least one somatic variation is detected in the second sample, or (b) as negative for ctDNA, if the overall posterior probability for the presence of the cancer in the subject is less than the predetermined threshold and the presence of the at least one somatic variation is not detected in the second sample.

In some embodiments, the at least one epigenetic feature comprises a methylation status, a nucleosomal position, a position of DNA binding proteins, and/or a fragmentomic signal of at least one of the plurality of genomic regions. In some embodiments, the at least one epigenetic feature comprises the methylation status. In some embodiments, the at least one epigenetic rate comprises a methylation rate. In some embodiments, the at least one epigenetic feature comprises the position of DNA binding proteins. In some embodiments, the DNA binding proteins comprise histones, transcription factors, or CCCTC-binding factor (CTCF) proteins. In some embodiments, the at least one epigenetic feature comprises the fragmentomic signal. In some embodiments, the fragmentomic signal comprises a length of the polynucleotides and/or a start position and an end position of the polynucleotides. In some embodiments, the fragmentomic signal comprises a length of the polynucleotides for a blood sample and a nucleosomal position for the polynucleotides of a tissue sample. In some embodiments, the nucleosomal position is determined by chromatin immunoprecipitation sequencing (ChIP-Seq).

In some embodiments, the tagging comprises attaching a set of tags to at least the portion of the partitioned polynucleotides to generate the tagged parent polynucleotides, wherein each of the tagged parent polynucleotides comprises one or more tags from among the set of tags. In some embodiments, each tag from among the set of tags comprises at least one barcode from among a plurality of barcodes. In some embodiments, the plurality of barcodes comprises 5 to 150 barcodes. In some embodiments, a given barcode of the plurality of barcodes has a length of at least 5 base pairs (bp).

In some embodiments, the method further comprises, prior to the sequencing, amplifying at least a portion of the enriched polynucleotides. In some embodiments, the amplifying, performed prior to the enriching or prior to the sequencing, comprises using primers comprising a sample index to enable multiplex sequencing.

In some embodiments, the sequencing comprises next-generation sequencing. In some embodiments, the sequencing comprises bisulfite sequencing. In some embodiments, the sequencing comprises bisulfite-free methylation sequencing. In some embodiments, the bisulfite-free methylation sequencing comprises TET-assisted pyridine borane sequencing (TAPS), APOBEC-coupled epigenetic sequencing (ACE-seq), TET-assisted bisulfite sequencing (TAB-seq), or selective chemical labeling and enrichment of hydroxymethyl cytosine (hmC-Seal).

In some embodiments, each of the plurality of genomic regions comprises at least 1 base pair (bp), at least 2 bp, at least 5 bp, at least 10 bp, at least 20 bp, at least 50 bp, at least 100 bp, at least 200 bp, at least 500 bp, at least 1000 bp, at least 2000 bp, at least 5000 bp, at least 10,000 bp, at least 20,000 bp, at least 50,000 bp, at least 100,000 bp, at least 200,000 bp, at least 500,000 bp, or at least 1,000,000 bp.

In some embodiments, the analyzing comprises: i. mapping the set of sequencing reads to a reference sequence; ii. determining a plurality of epigenetic rates for the plurality of genomic regions of the first sample; iii. determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample; iv. combining the plurality of likelihoods for the plurality of genomic regions to determine an overall posterior probability for the presence of the cancer in the subject; v. determining a most likely estimate of tumor fraction of the second sample from the overall posterior probability for the presence of cancer; and vi. comparing the most likely estimate of tumor fraction of the second sample with a predetermined threshold.

In some embodiments, the method or system further comprises vii. classifying the subject (a) as positive for circulating tumor DNA (ctDNA), if the most likely estimate of tumor of the second sample is greater than or equal to the predetermined threshold, or (b) as negative for ctDNA, if the most likely estimate of tumor of the second sample is less than the predetermined threshold.

In some embodiments, the method or system further comprises analyzing the plurality of genomic regions from the set of sequencing reads of the at least two samples to detect the presence of at least one somatic variation in the second sample. In some embodiments, the at least one somatic variation comprises a single nucleotide variation (SNV), insertion or deletion (indel), copy number variation (CNV), gene fusion, or combination thereof.

In some embodiments, the method or system further comprises: vii. classifying the subject (a) as positive for circulating tumor (ctDNA), if the most likely estimate of tumor of the second sample is greater than or equal to the predetermined threshold or the presence of the at least one somatic variation is detected in the second sample, or (b) as negative for ctDNA, if the most likely estimate of tumor of the second sample is less than the predetermined threshold and the presence of the at least one somatic variation is not detected in the second sample.

In some embodiments, the method or system further comprises generating a report which optionally includes information relating to the presence or absence of cancer in the subject. In some embodiments, the method for system further comprises communicating the report to a third party, such as the subject or a health care practitioner.

In another aspect, the present disclosure provides a non-transitory computer-readable medium comprising machine executable code that, upon execution by one or more computer processors, implements a method for In another aspect, the present disclosure provides a non-transitory computer-readable medium comprising machine-executable code that, upon execution by one or more computer processors, implements any of the methods above or elsewhere herein.

In another aspect, the present disclosure provides a system comprising one or more computer processors and computer memory coupled thereto. The computer memory comprises machine executable code that, upon execution by the one or more computer processors, implements any of the methods above or elsewhere herein.

In another aspect the present disclosure provides a system or method for obtaining information of one or more epigenetic features at one or more genomic locations in a first sample (e.g., polynucleotide extracted from cancer tissue specimen) obtained at a first time point (e.g. during a surgery), then using the information of the one or more epigenetic features in the first sample to analyze the one or more epigenetic features from the corresponding genomic locations in a second sample (e.g., cfDNA) obtained at a second time point (e.g. typically after surgery), wherein the information of the one or more epigenetic features obtained in the first sample is used to modify the criteria of/analyze the one or more epigenetic features in the second sample for classifying the subject for presence or absence of tumor.

In some embodiments of each and every aspect of the invention, the results of the systems and/or methods disclosed herein are used as an input to generate a report. The report may be in a paper or electronic format. For example, information on the presence or absence of cancer, as determined by the methods or systems disclosed herein, can be displayed in such a report. Alternatively or additionally, the report may comprise information relating to the epigenetic rates of the epigenetic features, for example whether they are above or below the adjusted epigenetic rate threshold. The methods or systems disclosed herein may further comprise a step of communicating the report to a third party, such as the subject from whom the sample derived or a health care practitioner.

The various steps of the methods disclosed herein, or the steps carried out by the systems disclosed herein, may be carried out at the same time or different times, and/or in the same geographical location or different geographical locations, e.g. countries. The various steps of the methods disclosed herein can be performed by the same person or different people.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1:
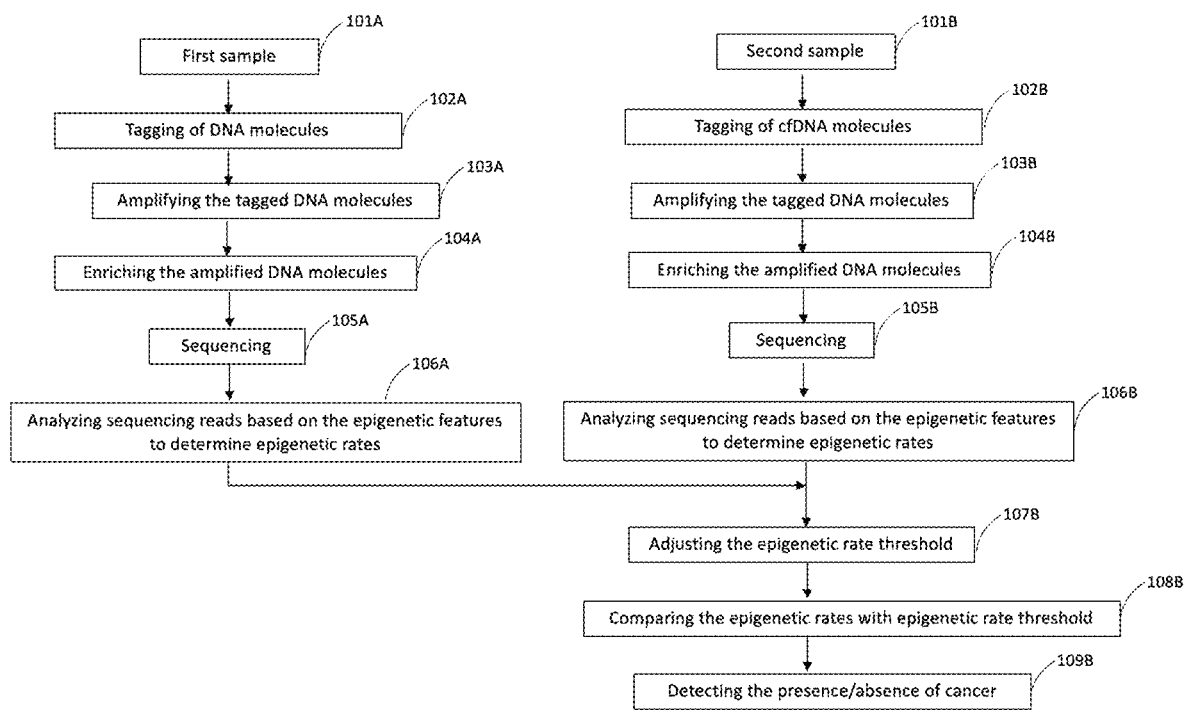
FIG. 1 is a flow chart representation of a method for detecting the presence or absence of cancer in a subject according to an embodiment of the disclosure.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adapter: As used herein, "adapter" refers to a short nucleic acid (e.g., less than about 500 nucleotides, less than about 100 nucleotides, or less than about 50 nucleotides in length) that is typically at least partially double-stranded and is attached to either one end or both ends (i.e., two adapters are attached to both ends of the nucleic acid—one adapter at end of the nucleic acid) of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequence reads of a given nucleic acid molecule. Adapters of the same or different sequences can be linked to the respective ends of a nucleic acid molecule. In some embodiments, the adapters of the same sequence is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides and the other end of the Y-shaped adapter comprises a non-complementary sequence which does not hybridize to form a double-strand. In still other example embodiments, an adapter is a bell-shaped adapter that includes a blunt or tailed end for joining to a nucleic acid molecule to be analyzed. Other examples of adapters include T-tailed and C-tailed adapters.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. Amplification includes but is not limited to polymerase chain reaction (PCR).

Barcode: As used herein, "barcode" or "molecular barcode" in the context of nucleic acids refers to a nucleic acid molecule comprising a sequence that can serve as a molecular identifier. For example, individual "barcode" sequences are typically added to each DNA fragment during next-generation sequencing (NGS) library preparation so that each read can be identified and sorted before the final data analysis.

Cancer Type: As used herein, "cancer type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as, but not limited to, Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Captured set: As used herein, a "captured set" of nucleic acids refers to nucleic acids that have undergone capture.

Capturing: As used herein, "capturing" or "enriching" one or more target nucleic acids refers to preferentially isolating or separating the one or more target nucleic acids from non-target nucleic acids.

Cell-Free Nucleic Acid: As used herein, "cell-free nucleic acid" refers to nucleic acids not contained within or otherwise bound to a cell or, in some embodiments, nucleic acids remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. A cell-free nucleic acid can have one or more epigenetic modifications, for example, a cell-free nucleic acid can be acetylated, 5-methylated, and/or hydroxy methylated.

Cellular Nucleic Acids: As used herein, "cellular nucleic acids" means nucleic acids that are disposed within one or more cells from which the nucleic acids have originated, at least at the point a sample is taken or collected from a subject, even if those nucleic acids are subsequently removed (e.g., via cell lysis) as part of a given analytical process.

Corresponding to a target region set: As used herein, "corresponding to a target region set means that a nucleic acid, such as cfDNA, originated from a locus in the target region set or specifically binds one or more probes for the target-region set.

Coverage: As used herein, the terms "coverage", "total molecule count", or "total allele count" are used interchangeably. They refer to the total number of DNA molecules at a particular genomic position in a given sample.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA typically includes a chain of nucleotides comprising four types of nucleotide bases; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotide bases; A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "sequencing data," "nucleic acid sequencing information," "sequence information," "nucleic acid sequence," "nucleotide sequence", "genomic sequence," "sequence read" or "sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

DNA sequence: As used herein, "DNA sequence" or "sequence" refers to "raw sequence reads" and/or "consensus sequences." Raw sequence reads are the output of a DNA sequencer, and typically include redundant sequences of the same parent molecule, for example after amplification. "Consensus sequences" are sequences derived from redundant sequences of a parent molecule intended to represent the sequence of the original parent molecule. Consensus sequences includes the base identity at a single position. In some embodiments, consensus sequence can represent a single nucleotide base at a particular genomic position. In some embodiments, consensus sequence can represent a string of nucleotide bases at a plurality of genomic positions. Consensus sequences can be produced by voting (wherein each majority nucleotide, e.g., the most commonly observed nucleotide at a given base position, among the sequences is the consensus nucleotide) or other approaches such as comparing to a reference genome. Consensus sequences can be produced by tagging original parent molecules with unique or non-unique molecular tags, which allow tracking of the progeny sequences (e.g., after amplification) by tracking of the tag and/or use of sequence read internal information. Examples of tagging or barcoding, and uses of tags or barcodes, are provided in, for example, U.S. Patent Pub. Nos. 2015/0368708, 2015/0299812, 2016/0040229, and 2016/0046986, each of which is entirely incorporated herein by reference.

Enriched sample: As used herein, "enriched sample" refers to a sample that has been enriched for specific regions of interest. The sample can be enriched by amplifying regions of interest or by using single-stranded DNA/RNA probes or double stranded DNA probes that can hybridize to nucleic acid molecules of interest (e.g., SureSelect®; probes, Agilent Technol). In some embodiments, an enriched sample refers to a subset or portion of the processed sample that is enriched, where the subset or portion of the processed sample being enriched contains nucleic acid molecules from a sample of cell-free polynucleotides or polynucleotides.

Epigenetic characteristic: As used herein, "epigenetic characteristic" refers to any directly observable measure of the DNA molecule that can be used in the analysis of the epigenetic feature of that DNA molecule. For example, if the epigenetic feature is methylation, then the epigenetic characteristic of the DNA molecule can refer to, but not limited to, the partitioning of the DNA molecule, number of CpG residues in the DNA molecule and the location (or offset) of the DNA molecule. For example, if the epigenetic feature is fragmentomic signal, then the epigenetic characteristics can be, but not limited to, length of the cfDNA molecules, the location (or offset) of the cfDNA molecule—start and/or end positions of the cfDNA molecules.

Epigenetic feature: As used herein, "epigenetic feature" refers to any parameter that may manifest a non-sequence modification of nucleic acids and also includes chromatin modifications. These modifications do not change the sequence of the DNA. The epigenetic features can include, but not limited to, methylation state; fragmentomic signal; position/distribution of nucleosome, CTCF proteins, transcription start sites, regulatory proteins and any other proteins that may bind to the DNA.

Epigenetic rate: As used herein, "epigenetic rate" refers to the probability, likelihood, or percentage of a given epigenetic feature in a DNA molecule. For example, if the epigenetic feature is methylation, then the epigenetic rate refers to the probability, likelihood, or percentage that a given base (for example: cytosine residue in a CpG) is methylated on a DNA molecule. In some embodiments, the epigenetic rate refers to the percentage of residues (for example: CpG residues) with a given epigenetic feature in a DNA molecule. In some embodiments, the epigenetic rate refers to the percentage of residues (for example: CpG residues) with a given epigenetic feature in molecules aligned to particular genomic position or genomic region.

Epigenetic rate threshold: As used herein, "epigenetic rate threshold" refers to a predetermined threshold of the epigenetic rate, which is used to determine the presence of tumor DNA in a sample. For example, if a particular genomic region is hypermethylated in tumor, then if the epigenetic rate at a particular genomic region is greater than the epigenetic rate threshold, then the patient is classified as having cancer. In another example, if a particular genomic region is hypomethylated in tumor, then if the epigenetic rate at a particular genomic region is lower than the epigenetic rate threshold, then the patient is classified as having cancer. The epigenetic rate threshold can be set so as to accommodate embodiments that comprise hypomethylated genomic regions in tumor and hypermethylated genomic regions in tumor. The epigenetic rate threshold can be determined based on a set of training samples (healthy donors and cancer patients or contrived samples) with known tumor fraction. In some embodiments, the epigenetic rate threshold is applied to epigenetic rates of one or more of the plurality of genomic regions.

Epigenetic target region set: As used herein, "epigenetic target region set" refers to a set of target regions that may manifest non-sequence modifications in neoplastic cells (e.g., tumor cells and cancer cells) and non-tumor cells (e.g., immune cells, cells from tumor microenvironment). These modifications do not change the sequence of the DNA. Examples of non-sequence modifications changes include, but not limited to, changes in methylation (increases or decreases), nucleosome distribution, CTCF binding, transcription start sites, regulatory protein binding regions and any other proteins that may bind to the DNA. For present purposes, loci susceptible to neoplasia-, tumor-, or cancer-associated focal amplifications and/or gene fusions may also be included in an epigenetic target region set because detection of a change in copy number by sequencing or a fused sequence that maps to more than one locus in a reference genome tends to be more similar to detection of exemplary epigenetic changes discussed above than detection of nucleotide substitutions, insertions, or deletions, e.g., in that the focal amplifications and/or gene fusions can be detected at a relatively shallow depth of sequencing because their detection does not depend on the accuracy of base calls at one or a few individual positions. For example, the epigenetic target region set can comprise a set of target regions for analyzing the fragment length or fragment end point location distribution. The terms "epigenetic" and "epigenomic" are used interchangeably herein.

Fragmentomic signal: As used herein, "fragmentomic signal" refers to the distribution of the cfDNA fragment sizes and cfDNA fragment positions at a particular genomic region. Fragmentomic signal can include, but not limited to, cfDNA fragment lengths, start and/or end positions of the cfDNA molecule (fragments' size coverage). Fragmentomic signal can also include the frequency at which a DNA molecule endpoint occurs at genomic location (at a specific position or region of interest surrounding the specific position). Fragmentomic signal can also include the nucleosomal positioning of DNA molecules. In some embodiments, the fragmentomic signal includes DNA molecule's endpoint information, but does not necessarily include a length parameter of the DNA molecule).

Genomic region: As used herein, "genomic region" refers to any region (e.g., range of base pair locations) of a genome, e.g., a chromosome, a chromosome arm, a gene, or an exon. A genomic region may be a contiguous or a non-contiguous region. A "genetic locus" (or "locus") can be a portion or entirety of a genomic region (e.g., a gene, a portion of a gene, or a single nucleotide of a gene). In some embodiments, the size of the genomic region comprises up to a length of a chromosome/chromosome arm or a topologically associated domain (TAD). In some embodiments, the size of the genomic region can be limited to the biological activity of the region (e.g., transcriptional unit or regulatory unit).

Hypermethylation: As used herein, "hypermethylation" refers to an increased level or degree of methylation of nucleic acid molecule(s) relative to the other nucleic acid molecules within a population (e.g., sample) of nucleic acid molecules. In some embodiments, hypermethylation refers to an increased level or degree of methylation of nucleic acid molecule(s) from a particular genomic region in tumor samples relative to the degree of methylation of nucleic acid molecules form the same genomic region in non-tumor samples. In some embodiments, hypermethylated DNA can include DNA molecules comprising at least 1 methylated residue, at least 2 methylated residues, at least 3 methylated residues, at least 5 methylated residues, at least 10 methylated residues, at least 20 methylated residues, at least 25 methylated residues, or at least 30 methylated residues.

Hypomethylation: As used herein, "hypomethylation" refers to a decreased level or degree of methylation of nucleic acid molecule(s) relative to the other nucleic acid molecules within a population (e.g., sample) of nucleic acid molecules. In some embodiments, hypomethylated DNA includes unmethylated DNA molecules. In some embodiments, hypomethylation refers to an decreased level or degree of methylation of nucleic acid molecule(s) from a particular genomic region in tumor samples relative to the degree of methylation of nucleic acid molecules form the same genomic region in non-tumor samples. In some embodiments, hypomethylated DNA can include DNA molecules comprising 0 methylated residues, at most 1 methylated residue, at most 2 methylated residues, at most 3 methylated residues, at most 4 methylated residues, or at most 5 methylated residues.

Methylation: As used herein, "methylation" or "DNA methylation" can refer to the presence of a methyl group to the cytosine at a CpG site (cytosine-phosphate-guanine site—i.e., a cytosine followed by a guanine in a 5'→3' direction of the nucleic acid sequence). In some embodiments, DNA methylation comprises addition of a methyl group to adenine, such as in $N^6$-methyladenine. In some embodiments, DNA methylation is 5-methylation (modification of the 5th carbon of the 6-carbon ring of cytosine). In some embodiments, 5-methylation comprises addition of a methyl group to the 5C position of the cytosine to create 5-methylcytosine (m5c). In some embodiments, methylation comprises a derivative of m5c. Derivatives of m5c include, but are not limited to, 5-hydroxymethylcytosine (5-hmC), 5-formylcytosine (5-fC), and 5-caryboxylcytosine (5-caC). In some embodiments, DNA methylation is 3C methylation (modification of the 3rd carbon of the 6-carbon ring of cytosine). In some embodiments, 3C methylation comprises addition of a methyl group to the 3C position of the cytosine to generate 3-methylcytosine (3mC). Methylation can also occur at non CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Methylation rate: As used herein, "methylation rate" refers to the probability, likelihood, or percentage that a given base (for example: cytosine residue in a CpG) is methylated on a DNA molecule at a particular genomic region analyzed in the sample. In some embodiments, the methylation rate may be applied to a defined region that comprises one or more potentially methylated bases. In some embodiments, the methylation rate refers to the percentage of CpG residues methylated in a DNA molecule. In some embodiments, the methylation rate refers to the percentage of CpG residues methylated in molecules aligned to particular genomic position or genomic region. Methylation rate can be measured by a variety of methods including, but not limited to, either using bisulfite sequencing (single base resolution) or using partitioning (DNA molecule resolution). Methylation rate can be estimated in different ways. One estimation can be by counting how many DNA fragments end up in each methylation dependent partition or by counting the number of converted CpGs per fragment in the case of bisulfite sequencing. In addition, in the case of methylation dependent partitioning, the rate estimation can be normalized using a set of predefined regions with known methylation state or spiked-in contrived DNA with known methylation state, deriving rate-parametrized partition distributions and estimating the rate using a maximum likelihood approach.

Mutation: As used herein, "mutation" refers to a variation from a known reference sequence and includes mutations such as, for example, single nucleotide variants (SNVs), and insertions or deletions (indels). A mutation can be a germline or somatic mutation. In some embodiments, a reference sequence for purposes of comparison is a wildtype genomic sequence of the species of the subject providing a test sample, typically the human genome.

Neoplasm: As used herein, the terms "neoplasm" and "tumor" are used interchangeably. They refer to abnormal growth of cells in a subject. A neoplasm or tumor can be benign, potentially malignant, or malignant. A malignant tumor is a referred to as a cancer or a cancerous tumor.

Next-Generation Sequencing: As used herein, "next-generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next-generation sequencing techniques include, but are not limited to, sequencing by synthesis, sequencing by ligation, and sequencing by hybridization. In some embodiments, next-generation sequencing includes the use of instruments capable of sequencing single molecules. Example of commercially available instruments for performing next-generation sequencing include, but are not limited to, NextSeq, HiSeq, NovaSeq, MiSeq, Ion PGM and Ion GeneStudio S5.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), distinguish nucleic acids from different partitions (e.g., representing a partition tag) or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same molecular barcode.

Overall posterior probability for cancer presence: As used herein, the term "overall posterior probability for cancer presence" refers to the probability for cancer presence in the second sample, which is determined by combining the likelihoods of tumor fraction at one or more of the plurality of genomic regions determined using the epigenetic rates of the first and second samples and the epigenetic characteristics of the second sample. In some embodiments, "overall posterior probability for cancer presence" refers to the probability for cancer presence in the third sample, which is determined by combining the likelihoods of tumor fraction at one or more of the plurality of genomic regions determined using the epigenetic rates of the first, second and third samples and the epigenetic characteristics of the third sample.

Partitioning: As used herein, "partitioning" refers to physically separating or fractionating the nucleic acid molecules in a sample based on a characteristic of the nucleic acid molecules. The partitioning can be physical partitioning of molecules. Partitioning can involve separating the nucleic acid molecules into groups or sets based on the level of epigenetic feature (for e.g., methylation). For example, the nucleic acid molecules can be partitioned based on the level of methylation of the nucleic acid molecules. In some embodiments, the methods and systems used for partitioning may be found in PCT Patent Application No. PCT/US2017/068329, which is hereby incorporated by reference in its entirety.

Partitioned set: As used herein, "partitioned set" or "partition" refers to a set of nucleic acid molecules partitioned into a set or group based on the differential binding affinity of the nucleic acid molecules or proteins associated with the nucleic acid molecules to a binding agent. The binding agent binds preferentially to the nucleic acid molecules comprising nucleotides with epigenetic modification. For example, if the epigenetic modification is methylation, the binding agent can be a methyl binding domain (MBD) protein. In some embodiments, a partitioned set can comprise nucleic acid molecules belonging to a particular level or degree of epigenetic feature (for e.g., methylation). For example, the nucleic acid molecules can be partitioned into three sets— one set for highly methylated nucleic acid molecules, a second set for low methylated nucleic acid molecules, and a third set for intermediate methylated nucleic acid molecules. In another example, the nucleic acid molecules can be partitioned based on the number of nucleotides with epigenetic modification—one partitioned set can have nucleic acid molecules with nine methylated nucleotides, and another partitioned set can have unmethylated nucleic acid molecules (zero methylated nucleotides).

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g., 3-4, to hundreds of monomeric units. Whenever a polynucleotide is represented by a sequence of letters, such as "ATGCCTG", the nucleotides are in 5' 3' order from left to right, and in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases.

Processing: As used herein, "processing" refers to a set of steps used to generate a library of nucleic acids that is suitable for sequencing. The set of steps can include, but are not limited to, partitioning, end repairing, addition of sequencing adapters, tagging, and/or PCR amplification of nucleic acids.

Quantitative measure: As used herein, "quantitative measure" refers to an absolute or relative measure. A quantitative measure can be, without limitation, a number, a statistical measurement (e.g., frequency, mean, median, standard deviation, or quantile), or a degree or a relative quantity (e.g., high, medium, and low). A quantitative measure can be a ratio of two quantitative measures. A quantitative measure can be a linear combination of quantitative measures. A quantitative measure may be a normalized measure.

Reference Sequence: As used herein, "reference sequence" refers to a known sequence used for purposes of comparison with experimentally determined sequences. For example, a known sequence can be an entire genome, a chromosome, or any segment thereof. A reference sequence can align with a single contiguous sequence of a genome or chromosome or chromosome arm or can include non-contiguous segments that align with different regions of a genome or chromosome. Examples of reference sequences include, for example, human genomes, such as, hG19 and hG38.

Sample: As used herein, "sample" means anything capable of being analyzed by the methods and/or systems disclosed herein.

Sequencing: As used herein, "sequencing" refers to any of a number of technologies used to determine the sequence (e.g., the identity and order of monomer units) of a biomolecule, e.g., a nucleic acid such as DNA or RNA. Examples of sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Sequence-variable target region set: As used herein "sequence-variable target region set" refers to a set of target regions that may exhibit changes in sequence such as nucleotide substitutions, insertions, deletions, or gene fusions or transpositions in neoplastic cells (e.g., tumor cells and cancer cells).

Somatic Mutation: As used herein, the terms "somatic mutation" or "somatic variation" are used interchangeably. They refer to a mutation in the genome that occurs after conception. Somatic mutations can occur in any cell of the body except germ cells and accordingly, are not passed on to progeny.

Specifically binds: As used herein, "specifically binds" in the context of an probe or other oligonucleotide and a target sequence means that under appropriate hybridization conditions, the oligonucleotide or probe hybridizes to its target sequence, or replicates thereof, to form a stable probe:target hybrid, while at the same time formation of stable probe:non-target hybrids is minimized. Thus, a probe hybridizes to a target sequence or replicate thereof to a sufficiently greater extent than to a non-target sequence, to enable capture or detection of the target sequence. Appropriate hybridization conditions are well-known in the art, may be predicted based on sequence composition, or can be determined by using routine testing methods (see, e.g., Sambrook et al., Molecular Cloning, A Laboratory Manual, 2nd ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual in need of therapy or suspected of needing therapy. The terms "individual" or "patient" are intended to be interchangeable with "subject". For example, a subject can be an individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an autoimmune disease.

Target-region set: As used herein, "target-region set" or "set of target regions" or "target regions" or "target regions of interest" refers to a plurality of genomic loci or a plurality of genomic regions targeted for capture and/or targeted by a set of probes (e.g., through sequence complementarity).

Tumor fraction: As used herein, "tumor fraction" refers to the proportion of cfDNA molecules that originated from tumor cells for a given sample, or sample-region pair.

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

DETAILED DESCRIPTION

I. Overview

Cancer formation and progression may arise from both genetic modification and epigenetic features of deoxyribonucleic acid (DNA). The present disclosure provides methods of analysis of epigenetic features of DNA, such as cell-free DNA (cfDNA). Such epigenetic analysis includes methylation status and DNA fragment patterns discernable from measuring changes in fragment length distribution or the frequency fragment endpoints mapping to genomic locations. Such "fragmentomic signal" analysis can be used alone or in combination with existing technologies to determine the presence or absence of a disease or condition, prognosis of a diagnosed disease or condition, therapeutic treatment of a diagnosed disease or condition, or predicted treatment outcome for a disease or condition.

Circulating cell-free DNA (cfDNA) may be predominantly short DNA fragments (e.g., having lengths from about 100 to 400 base pairs, with a mode of about 165 bp) shed from dying tissue cells into bodily fluids such as peripheral blood (plasma or serum). Analysis of cfDNA may reveal, in addition to cancer-associated genetic variants, epigenetic footprints and signatures of phagocytic removal of dying cells, which may result in an aggregate nucleosomal occupancy profile of present malignancies (e.g., tumors) as well as their microenvironment components.

Cell-free DNA in the form of histone-protected complexes can be released by various host cells including neutrophils, macrophages, eosinophils, as well as tumor cells. Circulating DNA typically has a short half-life (e.g., about 10 to 15 minutes), and the liver is typically the major organ where circulating DNA fragments are removed from blood circulation. The accumulation of cfDNA in the circulation may result from increased cell death and/or activation, impaired clearance of cfDNA, and/or decreases in levels of endogenous DNase enzymes. Cell-free DNA circulating in a subject's bloodstream may typically be packed into membrane-coated structures (e.g., apoptotic bodies) or complexes with biopolymers (e.g., histones or DNA-binding plasma proteins). The process of DNA fragmentation and subsequent trafficking may be analyzed for their effects on the characteristics of cell-free DNA signals as detected by fragmentomic signal analysis.

In a cell nucleus (e.g., of a human), DNA typically exists in nucleosomes, which are organized into structures comprising about 145 base pairs (bp) of DNA wrapped around a core histone octamer. Electrostatic and hydrogen-bonding interactions of DNA and histone dimers may result in energetically unfavorable bending of DNA over the protein surface. Such bending may be sterically prohibitive to other DNA-binding proteins and hence may serve to regulate access to DNA in a cell nucleus. Nucleosome positioning in a cell may fluctuate dynamically (e.g., over time and across various cell states and conditions), e.g., partially unwrap and rewrap spontaneously. Since a fragmentomic signal may reflect histone-protected DNA fragments that originated from a configuration influenced by nucleosomal units, nucleosome stability and dynamics may influence such a fragmentomic signal. These nucleosome dynamics may stem from a variety of factors, such as: (i) ATP-dependent remodeling complexes, which may use the energy of ATP hydrolysis to slide the nucleosomes and exchange or evict histones from the chromatin fiber, (ii) histone variants, which may possess properties distinct from those of canonical histones and create localized specific domains within the chromatin fiber, (iii) histone chaperones, which may control the supply of free histones and cooperate with chromatin remodelers in histone deposition and eviction, and (iv) post-translational modifications (PTMs) of histones (e.g., acetylation, methylation, phosphorylation, and ubiquitination), which may directly or indirectly influence chromatin structure.

Hence, fragmentomic signal of cfDNA may be indicative of an aggregate cfDNA signal, stemming from multiple events related to heterogeneity in chromatin organization across the genome. Such chromatin organization may differ depending on factors such as global cellular identity, metabolic state, regional regulatory state, local gene activity in dying cells, and mechanisms of DNA clearance. Moreover, cell-free DNA fragmentomic signal may be only partially attributed to underlying chromatin architecture of contributing cells. Such cfDNA fragmentomic signal may be indicative of a more complex footprint of chromatin compaction during cell death and DNA protection from enzymatic digestion. Hence, chromatin maps specific to a given cell type or cell lineage type may only partially contribute to the inherent heterogeneity of DNA accessibility due to changes in nucleosome stability, conformation, and composition at various stages of cell death or debris trafficking. As a result, some nucleosomes may become preferentially present or not present in cell-free DNA (e.g., there may be a filtering mechanism which influences cfDNA clearance and releases into the blood circulation), which may depend on factors such as the mode and mechanism of death and cell corpse clearance.

A fragmentomic signal may be generated in a cell and released as cfDNA into blood circulation as a result of nuclear DNA fragmentation during cell processes such as apoptosis and necrosis. Such fragmentation may be produced as a result of different nuclease enzymes acting on DNA in different stages of cells, resulting in sequence-specific DNA cleavage patterns which may be analyzed in cfDNA fragmentomic signal. Classifying such clearance patterns may be a clinically relevant marker of cell environments (e.g., tumor microenvironments, inflammation, disease states, tumorigenesis, etc.). In some embodiments, fragmentomic signal are analyzed in only selected genomic target regions of interest.

Cancer can be indicated by other non-sequence modifications, such as methylation. Examples of methylation changes in cancer include local gains of DNA methylation in the CpG islands at the TSS of genes involved in normal growth control, DNA repair, cell cycle regulation, and/or cell differentiation. This hypermethylation can be associated with an aberrant loss of transcriptional capacity of involved genes and occurs at least as frequently as point mutations and deletions as a cause of altered gene expression. DNA methylation profiling can be used to detect regions with different extents of methylation ("differentially methylated regions" or "DMRs") of the genome that are altered during development or that are perturbed by disease, for example, cancer or any cancer-associated disease.

In some embodiments, DNA methylation comprises addition of a methyl group to a cytosine residue at a CpG site (cytosine-phosphate-guanine site (i.e., a cytosine followed by a guanine in a 5'→3' direction of the nucleic acid sequence). In some embodiments, DNA methylation comprises addition of a methyl group to an adenine residue, such as in $N^6$-methyladenine. In some embodiments, DNA methylation is 5-methylation (modification of the 5th carbon of the 6-carbon ring of cytosine). In some embodiments, 5-methylation comprises addition of a methyl group to the 5C position of the cytosine residue to create 5-methylcytosine (m5c or 5-mC). In some embodiments, methylation comprises a derivative of m5c. Derivatives of m5c include, but are not limited to, 5-hydroxymethylcytosine (5-hmC), 5-formylcytosine (5-fC), and 5-caryboxylcytosine (5-caC). In some embodiments, DNA methylation is 3C methylation (modification of the 3rd carbon of the 6-carbon ring of the cytosine residue). In some embodiments, 3C methylation comprises addition of a methyl group to the 3C position of the cytosine residue to generate 3-methylcytosine (3mC). Methylation can also occur at non-CpG sites, for example, methylation can occur at a CpA, CpT, or CpC site. DNA methylation can change the activity of methylated DNA region. For example, when DNA in a promoter region is methylated, transcription of the gene may be repressed. DNA methylation is critical for normal development and abnormality in methylation may disrupt epigenetic regulation. The disruption, e.g., repression, in epigenetic regulation may cause diseases, such as cancer. Promoter methylation in DNA may be indicative of cancer.

Methylation profiling can involve determining methylation patterns across different regions of the genome. For example, after partitioning molecules based on extent of methylation (e.g., relative number of methylated nucleotides per molecule) and sequencing, the sequences of molecules in the different partitions can be mapped to a reference genome. This can show regions of the genome that, compared with other regions, are more highly methylated or are less highly methylated. In this way, genomic regions, in contrast to individual molecules, may differ in their extent of methylation.

Combining the signals obtained from the epigenetic features (e.g., methylation profiling and fragmentomic signal analysis) of the patient with the signals obtained from somatic variations (e.g., SNV, indel, CNV, and gene fusions) facilitate the detection of cancer.

The present disclosure provides methods and systems for improving sensitivity of detecting cancer presence or absence in the patients by monitoring the epigenetic features in a cell-free DNA sample, e.g., after curative intent surgery of early stage cancer patients. The epigenetic features may vary from patient to patient depending on the type of cancer, the stage of cancer, and the extent of cancer metastasis. By analyzing the epigenetic features of the tissue sample (collected during surgery), the sensitivity of detecting cancer (recurrence or relapse) can be improved by analyzing the cell-free polynucleotides (e.g., obtained post-surgery) via utilizing the information obtained from the tissue sample analysis. These methods can be used in various applications, such as predicting prognosis, diagnosis, monitoring, recurrence, and/or relapse of cancer.

Accordingly, in one aspect, the present disclosure provides a method for detecting the presence or absence of cancer from a subject comprising: (a) obtaining at least one sample from the subject from at least two different time points to provide at least two samples, wherein a first sample of the at least two samples is obtained at a first time point of the at least two different time points and a second sample of the at least two samples is obtained at a second time point of the at least two different time points; (b) processing the polynucleotides from each of the at least two samples, comprising: i) tagging at least a portion of the polynucleotides, thereby generating tagged parent polynucleotides; ii) amplifying at least a portion of the tagged parent polynucleotides to generate progeny polynucleotides; iii) enriching at least a portion of the progeny polynucleotides for target genomic regions; thereby generating enriched polynucleotides; and iv) sequencing at least a portion of the enriched polynucleotides to generate a set of sequencing reads; and (c) analyzing a plurality of genomic regions for at least one epigenetic feature from the set of sequencing reads of the at least two samples, to detect the presence or absence of cancer in the subject at the second time point.

In some embodiments, the analyzing comprises i) mapping the set of sequencing reads to a reference sequence; ii) determining a plurality of epigenetic rates for the plurality of genomic regions of the at least two samples; iii) adjusting an epigenetic rate threshold based on the epigenetic rate of at least one of the plurality of genomic regions of the first sample; and iv) comparing the epigenetic rate for the plurality of genomic regions in the second sample with the adjusted epigenetic rate threshold. In some embodiments, the analyzing further comprises v) classifying the subject (a) as positive for ctDNA, if the epigenetic rate of at least one genomic region is greater than or equal to the adjusted epigenetic rate threshold, or (b) as negative for ctDNA, if the epigenetic rates of the plurality of genomic regions is less than the adjusted epigenetic rate threshold.

FIG. 1 illustrates an example embodiment of a method 100 for detecting the presence or absence of cancer in a subject. In step 101A, a first sample from the subject is obtained at a first time point. In some embodiments, the first sample is a polynucleotide sample, extracted from a tumor tissue specimen (e.g., during surgery). In some embodiments, the tumor tissue specimen from which the first sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample. In some embodiments, the polynucleotides sample obtained from the tissue specimen is treated with fragmentase to fragment the polynucleotides into a fragments of size 100-200 bp in average. In some embodiments, the first sample is a cell-free polynucleotide sample, extracted from the blood sample (e.g., collected prior to the surgery). The first sample is then subjected to a series of processing steps (102A to 105A).

In step 102A, a subset of the first sample is attached with tags to generate tagged parent polynucleotides. In some embodiments, the tag comprises one or more barcodes from a set of barcodes. In some embodiments, the set of barcodes comprises about 5-150 barcodes. In some embodiments, the barcode is at least 5 bp in length. In some embodiments, the amount of polynucleotides subjected to tagging can be no more than 50 ng, no more than 100 ng, no more than 150 ng, no more than 200 ng, no more than 300 ng, no more than 350 ng, no more than 400 ng, no more than 450 ng, or no more than 500 ng.

In step 103A, a subset of the tagged polynucleotides is amplified to generate progeny polynucleotides. In step 104A, a subset of the progeny polynucleotides that belong to a set of genomic regions of interest is enriched to generate enriched molecules. In some embodiments, the genomic region comprises at least 1 bp, at least 2 bp, at least 5 bp, at least 10 bp, at least 20 bp, at least 50 bp, at least 100 bp, at least 200 bp, at least 500 bp, at least 1000 bp, at least 2000 bp, at least 5000 bp, at least 10,000 bp, at least 20,000 bp, at least 50,000 bp, at least 100,000 bp, at least 200,000 bp, at least 500,000 bp, or at least 1,000,000 bp. In some embodiments, the size of the genomic region comprises up to a length of a chromosome or a topologically associated domain (TAD). In some embodiments, the size of the genomic region can be limited to the biological activity of the region (e.g., transcriptional unit or regulatory unit). In 105A, a subset of the enriched molecules is sequenced to generate a plurality of sequencing reads. The sequencing information obtained from the sequencing reads comprises sequences of the DNA molecules and the tags attached to the nucleic acid molecules. In some embodiments, the sequencing of enriched molecules comprises next-generation sequencing. In some embodiments, the sequencing comprises bisulfite sequencing. In such embodiments, the tagged DNA molecules, prior to the amplification step, are treated with bisulfite before sequencing to analyze the methylation pattern of DNA molecules. In some embodiments, the sequencing comprises bisulfite-free methylation detection sequencing. In some embodiments, the bisulfite-free methylation detection sequencing comprises TAPS (e.g., as described by Liu et al., Nature Biotechnology (2019); 37(4): 424-429; which is hereby incorporated by reference in its entirety), ACE-seq (e.g., as described by Schutsky et al., Nature Biotechnology (2018); 36:1083-1090; which is hereby incorporated by reference in its entirety), TAB-seq (e.g., as described by Yu et al., Cell (2012); 149(6):1368-1380; which is hereby incorporated by reference in its entirety) or hmC-Seal (e.g., as described by Song et al., Nature Biotechnology (2011); 29:68-72; which is hereby incorporated by reference in its entirety). In such embodiments, the tagged DNA molecules, prior to the amplification step, are treated with appropriate reagents that converts 5-methyl cytosine (5mC), cytosine (C) or hydroxymethyl cytosine (hmC) based on the type of bisulfite-free methylation detection sequencing prior to the sequencing to analyze the methylation pattern of DNA molecules. For example, if the bisulfite-free methylation detection sequencing is ACE-seq, then the tagged molecules are treated with APOBEC3A (A3A) enzyme that deaminates 5mC and C but not hmC.

In step 106A, the sequencing reads mapped to a plurality of genomic regions are analyzed based on one or more epigenetic features, and the epigenetic rates for the plurality of genomic regions are determined. The epigenetic feature can refer to any parameter that may manifest a non-sequence modification of nucleic acids. These modifications may not change the sequence of the DNA. In some embodiments, the epigenetic features can include, but not limited to, methylation status; fragmentomic signal; position/distribution of nucleosome, CTCF proteins, transcription start sites, regulatory proteins and any other proteins that may bind to the DNA. In some embodiments, the epigenetic feature comprises methylation status, nucleosomal position, position of DNA binding proteins, and/or fragmentomic signal of at least one genomic region. In some embodiments, the epigenetic feature comprises the methylation status. In some embodiments, the epigenetic feature comprises position of DNA binding proteins. In some embodiments, the DNA binding proteins comprise histones, transcription factors, and CTCF proteins. In some embodiments, the epigenetic feature comprises fragmentomic signal. In some embodiments, the fragmentomic signal comprises nucleosomal position, cell-free polynucleotides length, and/or start and end positions of the cell-free polynucleotides. In some embodiments, the fragmentomic signal comprises cell-free polynucleotides length for the second sample and nucleosomal position for the first sample. In some embodiments, the nucleosomal positions are determined by ChIP-Seq. In these embodiments, prior to tagging, further comprises, binding of antibodies to the first sample. In some embodiments, nucleosomal positions can be determined by RNA-Seq (for example, in cases of tumor specific gene expression pattern). The epigenetic rate refers to the probability, likelihood, or percentage of a given epigenetic feature in a DNA molecule. In some embodiments, if the epigenetic feature is methylation, then the epigenetic rate refers to the probability, likelihood, or percentage that a given base (for example: cytosine residue in a CpG) is methylated on a DNA molecule. Methylation rate can be estimated in different ways. One estimation can be by counting how many DNA fragments end up in each methylation dependent partition or by counting the number of converted CpGs per fragment in the case of bisulfate sequencing. In addition, in the case of methylation dependent partition, the rate estimation can be normalized using a set of predefined regions with known methylation state or spiked-in contrived DNA with known methylation state, deriving rate-parametrized partition distributions and estimating the rate using a maximum likelihood approach. In some embodiments, where the nucleosomal positions are determined by ChIP-Seq, the epigenetic rate refers to the probability or likelihood of the DNA molecule to be bound to the nucleosome. The epigenetic rates of the first sample are then utilized in analyzing the second sample obtained from the subject at a later time point (e.g., after the surgery).

In step 101B, the second sample from the subject is obtained at a second time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides. The second sample is then subjected to a series of processing steps (102B to 105B). The processing steps of the second sample are similar to that of the first sample. All the embodiments and features of processing steps described under the first sample analysis can be applied to the second sample as well. In step 102B, a subset of the second sample is attached with tags to generate tagged parent polynucleotides. In step 103B, a subset of the tagged parent polynucleotides is amplified to generate progeny polynucleotides. In step 104B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 105B, a subset of the enriched molecules is sequenced to generate a plurality of sequencing reads. The sequencing information obtained from the sequencing reads comprises sequences of the cfDNA molecules and the tags attached to the nucleic acid molecules. In some embodiments, the sequencing of enriched molecules comprises next-generation sequencing. In some embodiments, the sequencing comprises bisulfite sequencing. In such embodiments, the tagged DNA molecules, prior to the amplification step, are treated with bisulfite before sequencing to analyze the methylation pattern of DNA molecules. In some embodiments, the sequencing comprises bisulfite-free methylation detection sequencing. In some embodiments, the sequencing comprises bisulfite-free methylation detection sequencing TAPS, ACE-seq, TAB-seq, or hmC-Seal. In such embodiments, the tagged DNA molecules, prior to the amplification step, are treated with appropriate reagents that converts 5-methyl cytosine (5mC), cytosine (C) or hydroxymethyl cytosine (hmC) based on the type of bisulfite-free methylation detection sequencing prior to the sequencing to analyze the methylation pattern of DNA molecules. For example, if the bisulfite-free methylation detection sequencing is ACE-seq, then the tagged molecules are treated with APOBEC3A (A3A) enzyme that deaminates 5mC and C but not hmC.

In step 106B, the sequencing reads mapped to a plurality of genomic regions are analyzed based on one or more epigenetic features and the epigenetic rates for the plurality of genomic regions are determined. All the embodiments and features of epigenetic features and epigenetic rate described in the analysis of first sample can be applied to the second sample as well. In step 107B, the epigenetic rate threshold at a particular genomic region is adjusted based on the epigenetic rate of the first sample. Epigenetic rate threshold refers to a predetermined threshold of the epigenetic rate, which is used to determine the presence of tumor DNA in a sample. For example, in the first sample if a particular genomic region of interest has a methylation rate of 100%, then the epigenetic rate threshold for the second sample need not be adjusted for that particular genomic region. But for another genomic region if the methylation rate of the first sample is 50%, then the epigenetic rate threshold for the second sample can be lowered. In some embodiments, the epigenetic rate threshold can be any value between 0 and 1. In some embodiments, the epigenetic rate threshold can be any value between 0 and 100. In some embodiments, the adjusted epigenetic rate threshold can be lower or greater than the previously determined epigenetic rate threshold. The epigenetic rate threshold can be determined based on a set of training samples (healthy donors and cancer patients/contrived samples) with known tumor fraction. In step 108B, the epigenetic rate of the second sample for the plurality of genomic regions is then compared with the adjusted epigenetic rate threshold. In step 109B, the presence or absence of cancer is detected based on whether the subject is positive or negative for ctDNA. For example, if particular genomic region is hypermethylated in tumor, then if the epigenetic rate of the second sample at a particular genomic region is greater than the epigenetic rate threshold, then the subject is classified as being positive for ctDNA. In another example, if a particular genomic region is hypomethylated in tumor, then if the epigenetic rate of the second sample at a particular genomic region is lower than the epigenetic rate threshold, then the subject is classified as being positive for ctDNA. The epigenetic rate threshold can be set so as to accommodate embodiments that comprise hypomethylated genomic regions in tumor and hypermethylation genomic regions in tumor. In some embodiments, the subject is classified (i) as positive for ctDNA, if the epigenetic rate of the second sample in at least one genomic region of the second sample is greater than or equal to the adjusted epigenetic rate threshold; or (ii) as negative for ctDNA, if the epigenetic rates for the plurality of genomic regions of the second sample is less than the adjusted epigenetic rate threshold.

In some embodiments, prior to the tagging, the processing of the first sample and the second sample comprises partitioning at least a subset of the polynucleotides into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). Examples of binding agents include, but are not limited to, methyl binding domain (MBDs) and methyl binding proteins (MBPs). Examples of MBPs contemplated herein include, but are not limited to:

(a) MeCP2, which is a protein preferentially binding to 5-methyl-cytosine over unmodified cytosine;
(b) RPL26, PRP8, and the DNA mismatch repair protein MHS6, which preferentially bind to 5-hydroxymethyl-cytosine over unmodified cytosine;
(c) FOXK1, FOXK2, FOXP1, FOXP4, AND FOXI3, which preferably bind to 5-formylcytosine over unmodified cytosine (e.g., as described by Iurlaro et al., Genome Biol. 14, R119 (2013), which is hereby incorporated by reference in its entirety); and
(d) Antibodies specific to one or more methylated nucleotide bases.

Partitioning can refer to physically separating or fractionating the nucleic acid molecules based on a characteristic of the nucleic acid molecules. The partitioning can be physical partitioning of molecules. Partitioning can involve separating the nucleic acid molecules into groups or sets based on the level of non-sequence modification. For example, the nucleic acid molecules can be partitioned based on the level of methylation of the nucleic acid molecules. In some embodiments, the methods and systems used for partitioning may be performed as described by PCT Patent Application No. PCT/US2017/068329, which is hereby incorporated by reference in its entirety. In those embodiments, the nucleic acids are partitioned based on the different levels of methylation (e.g., different number or frequency of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). Over representation and under representation can be defined by the number of modifications present in a DNA molecule (e.g., cfDNA molecule) relative to the median number of modifications per strand in a population. For example, if the median number of 5-methylcytosine nucleotides in nucleic acid molecules in a sample is 2, a nucleic acid molecule including more than two 5-methylcytosine residues is over-represented and a nucleic acid with 1 or zero 5-methylcytosine residues is under-represented. The effect of the affinity separation is to enrich for nucleic acids that are over-represented in a modification in a bound phase and for nucleic acids that are under-represented in a modification in an unbound phase (i.e., in solution). The nucleic acids in the bound phase can be eluted before subsequent processing. In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. But if different from one another, the tags can have part of their sequence in common so as to identify the molecules to which they are attached as being of a particular partitioned set. For example, if the molecules of the sample are partitioned into two partitioned sets—P1 and P2, then the molecules in P1 can be tagged with A1, A2, A3, and so forth, and the molecules in P2 can be tagged with B1, B2, B3, and so forth. Such a tagging system allows distinguishing the partitioned sets and between the molecules within a partitioned set.

In some embodiments, processing can include steps such as, but not limited to, partitioning, end repairing, addition of sequencing adapters, tagging, and/or amplification of polynucleotides.

In some embodiments, in addition to analyzing the sequencing reads based on at least one epigenetic feature, the sequencing reads are analyzed for detecting the presence of at least one somatic variation in the second sample. In those embodiments, the subject is classified (a) as positive for ctDNA, if the epigenetic rate of at least one genomic region of the second sample is greater than or equal to the adjusted epigenetic rate threshold or at least one somatic variation is detected in the second sample, or (b) as negative for ctDNA, if the epigenetic rate for all the genomic regions of the second sample is less than the adjusted epigenetic rate threshold and the presence of the somatic variation is not detected in the second sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags is attached to the nucleic acids by ligation of adapters to the nucleic acids, wherein the adapters comprise one or more tags.

In another aspect, the present disclosure provides a method for detecting the presence or absence of cancer from a subject comprising: (a) obtaining at least one sample from the subject from at least two different time points to provide at least two samples, wherein a first sample of the at least two samples is obtained at a first time point of the at least two different time points and a second sample of the at least two samples is obtained at a second time point of the at least two different time points; (b) processing the polynucleotides from each of the at least two samples, comprising: i) tagging at least a subset of the polynucleotides, thereby generating tagged parent polynucleotides; ii) amplifying at least a portion of the tagged parent polynucleotides to generate progeny polynucleotides; iii) enriching at least a portion of the progeny polynucleotides for target genomic regions; thereby generating enriched polynucleotides; and iv) sequencing at least a portion of the enriched polynucleotides to generate a set of sequencing reads; and (c) analyzing a plurality of genomic regions for at least one epigenetic feature from the set of sequencing reads of the at least two samples, to detect the presence or absence of cancer in the subject.

In some embodiments, the analyzing comprises, (i) mapping the set of sequencing reads to a reference sequence, (ii) determining a plurality of epigenetic rates for the plurality of genomic regions of the first sample; (iii) determining a likelihood for a tumor fraction for one or more of the plurality of genomic regions in the second sample based on a predetermined set of epigenetic rates of the plurality of genomic regions for the second sample, a set of epigenetic characteristics for a set of cell-free polynucleotides in the second sample aligned to the plurality of genomic regions, and the epigenetic rate of the plurality of genomic regions of the first sample; (iv) combining the plurality of likelihoods for the one or more of the plurality of genomic regions to determine an overall posterior probability for cancer presence; and (v) comparing the overall posterior probability for cancer presence with a predetermined threshold. In some embodiments, the method further comprises, (vi) classifying the subject (a) as positive for ctDNA, if the overall posterior probability for cancer presence is greater than or equal to the predetermined threshold, or (b) as negative for ctDNA, if the overall posterior probability for cancer presence is less than the predetermined threshold. The overall posterior probability for cancer presence can refer to the probability for cancer presence in the sample, which is determined by combining the likelihoods of tumor fraction at one or more of the plurality of genomic regions determined using the epigenetic rates of the first and second samples and the epigenetic characteristics for a set of cell-free polynucleotides in the second sample aligned to the genomic region.

Figure 2:
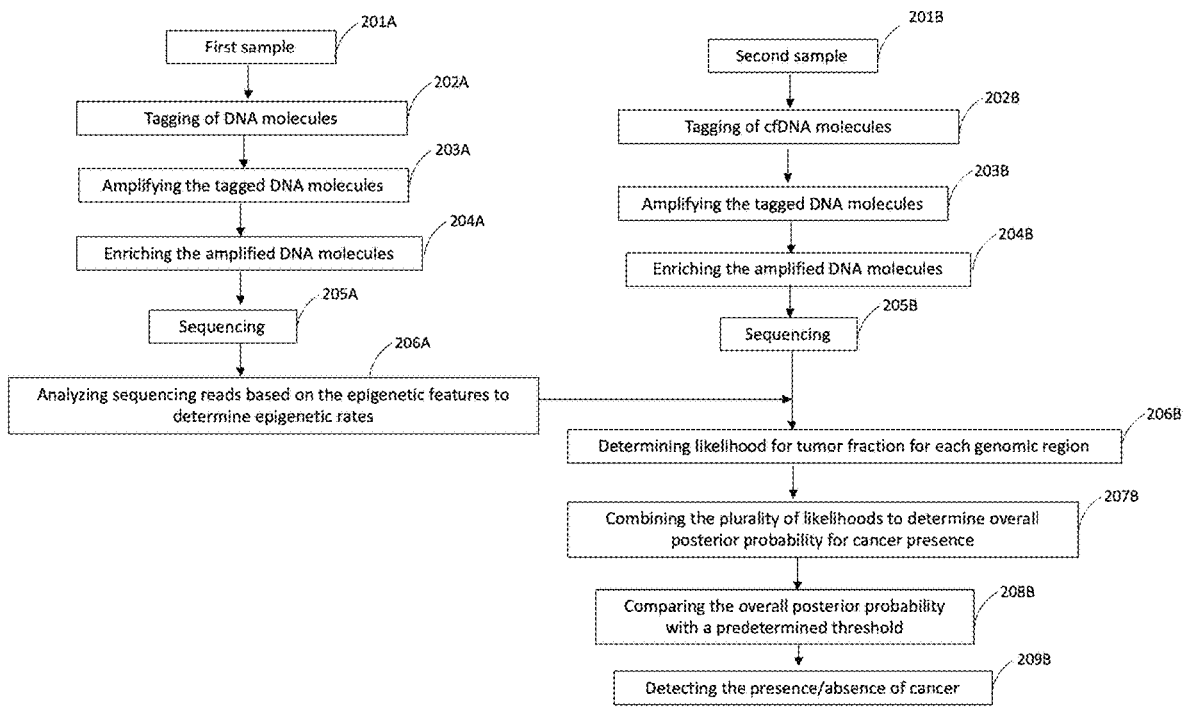
FIG. 2 is a flow chart representation of a method for detecting the presence or absence of cancer in a subject according to an embodiment of the disclosure.

FIG. 2 illustrates an example embodiment of a method 200 for detecting the presence or absence of cancer in a subject. In step 201A, a first sample from the subject is obtained at a first time point. In some embodiments, the first sample is a polynucleotide sample, extracted from a tumor tissue specimen (e.g., during surgery). In some embodiments, the tumor tissue specimen from which the first sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample and undergoes processing steps similar to the first sample. In some embodiments, the polynucleotides sample obtained from the tissue specimen is treated with fragmentase to fragment the polynucleotides into a fragments of size 100-200 bp in average. In some embodiments, the first sample is a cell-free polynucleotide sample, extracted from the blood sample (collected prior to the surgery).

The first sample is then subjected to a series of processing steps (202A to 205A). The processing steps described here are similar to the processing steps described in FIG. 1. All the embodiments and features of processing steps described in FIG. 1 can be applied here as well. In step 202A, a subset of the first sample is attached with tags to generate tagged parent polynucleotides. In step 203A, a subset of the tagged parent polynucleotides is amplified to generate progeny polynucleotides. In 204A, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 205A, a subset of the enriched molecules is sequenced to generate a plurality of sequencing reads. The sequencing information obtained from the sequencing reads comprises sequence of the polynucleotide and the tags attached to the polynucleotide. In some embodiments, the sequencing of enriched molecules comprises next-generation sequencing. In some embodiments, the sequencing comprises bisulfite sequencing. In such embodiments, the tagged DNA molecules, prior to the amplification step, are treated with bisulfite before sequencing to analyze the methylation pattern of DNA molecules. In some embodiments, the sequencing comprises bisulfite-free methylation detection sequencing. In some embodiments, the sequencing comprises bisulfite-free methylation detection sequencing TAPS, ACE-seq, TAB-seq, or hmC-Seal. In such embodiments, the tagged DNA molecules, prior to the amplification step, are treated with appropriate reagents that converts 5-methyl cytosine (5mC), cytosine (C) or hydroxymethyl cytosine (hmC) based on the type of bisulfite-free methylation detection sequencing prior to the sequencing to analyze the methylation pattern of DNA molecules. For example, if the bisulfite-free methylation detection sequencing is ACE-seq, then the tagged molecules are treated with APOBEC3A (A3A) enzyme that deaminates 5mC and C but not hmC.

In step 206A, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 can be applied here as well. These epigenetic rates are then utilized in analyzing the second sample obtained from the subject at a later time point (e.g., after the surgery).

In step 201B, the second sample from the subject is obtained at a second time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides. The second sample is then subjected to a series of processing steps (202B to 205B). The processing steps of the second sample may be similar to that of the first sample. All the embodiments and features of processing steps described in FIG. 1 can be applied here as well. In step 202B, a subset of the second sample is attached with tags to generate tagged parent polynucleotides. In 203B, a subset of the tagged parent polynucleotides is amplified to generate progeny polynucleotides. In step 204B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 205B, a subset of the enriched molecules is sequenced to generate a plurality of sequencing reads. In some embodiments, the sequencing of enriched molecules comprises next-generation sequencing. In some embodiments, the sequencing comprises bisulfite sequencing. In such embodiments, the tagged DNA molecules, prior to the amplification step, are treated with bisulfite before sequencing to analyze the methylation pattern of DNA molecules. In some embodiments, the sequencing comprises bisulfite-free methylation detection sequencing. In some embodiments, the sequencing comprises bisulfite-free methylation detection sequencing TAPS, ACE-seq, TAB-seq, or hmC-Seal. In such embodiments, the tagged DNA molecules, prior to the amplification step, are treated with appropriate reagents that converts 5-methyl cytosine (5mC), cytosine (C) or hydroxymethyl cytosine (hmC) based on the type of bisulfite-free methylation detection sequencing prior to the sequencing to analyze the methylation pattern of DNA molecules. For example, if the bisulfite-free methylation detection sequencing is ACE-seq, then the tagged molecules are treated with APOBEC3A (A3A) enzyme that deaminates 5mC and C but not hmC.

In step 206B, the sequencing reads mapped to a plurality of genomic regions are analyzed to determine a likelihood for tumor fraction for one or more of the plurality of genomic regions based on a predetermined set of epigenetic rates of the plurality of genomic regions for the second sample, a set of epigenetic characteristics for a set of cell-free polynucleotides in the second sample aligned to the plurality of genomic regions and the epigenetic rates of the plurality of genomic regions for the first sample. In some embodiments, the predetermined set of epigenetic rates of the plurality of genomic regions of the second sample can be a set of at least 1, at least 5, at least 10, at least 50, at least 100, at least 200, at least 500 or at least 1000 epigenetic rates between 0 and 1. In some embodiments, if the epigenetic feature is methylation, the epigenetic characteristics comprises partitioning of the cfDNA molecule, number of CpG residues in the cfDNA molecule and the location (or offset) of the cfDNA molecule. In some embodiments, if the epigenetic feature is fragmentomic signal, then the epigenetic characteristics comprise length of the cfDNA molecules, the location (or offset) of the cfDNA molecule—start and/or end positions of the cfDNA molecules.

In step 207B, the plurality of likelihoods for tumor fraction of the plurality of genomic regions of the second sample is combined to determine an overall posterior probability for cancer presence. In some embodiments, the plurality of likelihoods for tumor fraction of a subset of the plurality of the genomic regions of the second sample is combined to determine the overall posterior probability for cancer presence. In some embodiments, the subset of the plurality of genomic regions in the second sample is selected based on the epigenetic rates of the first sample. In some embodiments, the subset of the plurality of genomic regions in the second sample comprise a genomic region with one highest epigenetic rate in the first sample, genomic regions with 2 highest epigenetic rates in the first sample, genomic regions with 5 highest epigenetic rates in the first sample, genomic regions with 10 highest epigenetic rates in the first sample, genomic regions with 20 highest epigenetic rates in the first sample, genomic regions with 30 highest epigenetic rates in the first sample, genomic regions with 40 highest epigenetic rates in the first sample, genomic regions with 50 highest epigenetic rates in the first sample, genomic regions with 60 highest epigenetic rates in the first sample, genomic regions with 70 highest epigenetic rates in the first sample, genomic regions with 80 highest epigenetic rates in the first sample, genomic regions with 90 highest epigenetic rates in the first sample, genomic regions with 100 highest epigenetic rates in the first sample, genomic regions with 150 highest epigenetic rates in the first sample, genomic regions with 200 highest epigenetic rates in the first sample, genomic regions with at least 250 highest epigenetic rates in the first sample, genomic regions with at least 300 highest epigenetic rates in the first sample, genomic regions with at least 400 highest epigenetic rates in the first sample, genomic regions with at least 500 highest epigenetic rates in the first sample, genomic regions with at least 600 highest epigenetic rates in the first sample, genomic regions with at least 700 highest epigenetic rates in the first sample, genomic regions with at least 800 highest epigenetic rates in the first sample, genomic regions with at least 900 highest epigenetic rates in the first sample, genomic regions with at least 1000 highest epigenetic rates in the first sample, genomic regions with at least 5000 highest epigenetic rates in the first sample or genomic regions with at least 10,000 highest epigenetic rates in the first sample. In some embodiments, the subset of the plurality of genomic regions in the second sample comprise genomic regions with 5 highest epigenetic rates in the first sample. In some embodiments, the subset of the plurality of genomic regions in the second sample comprise genomic regions with 10 highest epigenetic rates in the first sample. In some embodiments, the subset of the plurality of genomic regions in the second sample comprise genomic regions with 25 highest epigenetic rates in the first sample. In some embodiments, the subset of the plurality of genomic regions in the second sample comprise genomic regions with 50 highest epigenetic rates in the first sample. In some embodiments, the subset of the plurality of genomic regions in the second sample comprise genomic regions with 100 highest epigenetic rates in the first sample. In some embodiments, the subset of the plurality of genomic regions in the second sample comprise genomic regions with 200 highest epigenetic rates in the first sample. In some embodiments, the subset of the plurality of genomic regions in the second sample comprise genomic regions with 250 highest epigenetic rates in the first sample. In some embodiments, the subset of the plurality of genomic regions in the second sample comprise genomic regions with 500 highest epigenetic rates in the first sample. In some embodiments, the subset of the plurality of genomic regions in the second sample comprise genomic regions with 1000 highest epigenetic rates in the first sample. In some embodiments, the subset of the plurality of genomic regions in the second sample comprise genomic regions with 5000 highest epigenetic rates in the first sample. In some embodiments, the subset of the plurality of genomic regions in the second sample comprise genomic regions with 10,000 highest epigenetic rates in the first sample. In some embodiments, the subset of the plurality of genomic regions in the second sample comprise genomic regions with at least 5 highest epigenetic rates in the first sample. In some embodiments, the subset of the plurality of genomic regions in the second sample comprise genomic regions with at least 10 highest epigenetic rates in the first sample. In some embodiments, the subset of the plurality of genomic regions in the second sample comprise genomic regions with at least 25 highest epigenetic rates in the first sample. In some embodiments, the subset of the plurality of genomic regions in the second sample comprise genomic regions with at least 50 highest epigenetic rates in the first sample. In some embodiments, the subset of the plurality of genomic regions in the second sample comprise genomic regions with at least 100 highest epigenetic rates in the first sample. In some embodiments, the subset of the plurality of genomic regions in the second sample comprise genomic regions with at least 200 highest epigenetic rates in the first sample. In step 208B, the overall posterior probability is compared with a predetermined threshold. In step 209B, the presence or absence of cancer is detected based on whether the subject is positive or negative for ctDNA. The subject is classified (i) as positive for ctDNA, if the overall posterior probability is greater than or equal to the predetermined threshold; or (ii) as negative for ctDNA, if the overall posterior probability is less than the predetermined threshold. In some embodiments, the predetermined threshold can be any value between 0 and 1. In some embodiments, the overall posterior probability for a range of tumor fractions in compared with a predetermined threshold. In some embodiments, the predetermined threshold can be less than 0.5, 0.5, 0.6, 0.7, 0.75, 0.8, 0.9, 0.91, 0.92, 0.93, 0.94, 0.95, 0.96, 0.97, 0.98, or 0.99. In some embodiments, the predetermined threshold can be 0.1. In some embodiments, the predetermined threshold can be 0.2. In some embodiments, the predetermined threshold can be 0.3. In some embodiments, the predetermined threshold can be 0.4. In some embodiments, the predetermined threshold can be 0.5. In some embodiments, the predetermined threshold can be 0.6. In some embodiments, the predetermined threshold can be 0.7. In some embodiments, the predetermined threshold can be 0.8. In some embodiments, the predetermined threshold can be 0.9. In some embodiments, the predetermined threshold can be 0.95. In some embodiments, the predetermined threshold can be 0.99.

In some embodiments, the overall posterior probability for cancer presence is used to determine the most likely estimate of tumor fraction of the second sample, which in turn can be used to classify a patient for presence or absence of cancer. The most likely estimate of tumor fraction is compared with a predetermined threshold. The subject is classified (i) as positive for ctDNA, if the most likely estimate of tumor fraction is greater than or equal to the predetermined threshold; or (ii) as negative for ctDNA, if the most likely estimate of tumor fraction is less than the predetermined threshold. In some embodiments, the predetermined threshold can be any value between 0 and 1. In some embodiments, the predetermined threshold can be less than 0.5, 0.5, 0.6, 0.7, 0.75, 0.8, 0.9, 0.91, 0.92, 0.93, 0.94, 0.95, 0.96, 0.97, 0.98, or 0.99. In some embodiments, the predetermined threshold can be any value between $10^{-5}$ to $10^{-2}$. In some embodiments, the predetermined threshold can be any value between $10^{-7}$ to $10^{-2}$. In some embodiments, the predetermined threshold can be any value between $10^{-6}$ to $10^{-2}$. In some embodiments, the predetermined threshold can be any value between $10^{-5}$ to 0.1. In some embodiments, the predetermined threshold can be any value between $10^{-4}$ to $10^{-3}$. In some embodiments, the predetermined threshold can be $2\times10^{-4}$. In some embodiments, the predetermined threshold can be $3\times10^{-4}$. In some embodiments, the predetermined threshold can be $4\times10^{-4}$. In some embodiments, the predetermined threshold can be $5\times10^{-4}$. In some embodiments, the predetermined threshold can be $6\times10'$. In some embodiments, the predetermined threshold can be $7\times10^{-4}$. In some embodiments, the predetermined threshold can be $8\times10^{-4}$. In some embodiments, the predetermined threshold can be $9\times10'$. In some embodiments, the predetermined threshold can be $2\times10^{-3}$. In some embodiments, the predetermined threshold can be $5\times10^{-3}$. In some embodiments, the predetermined threshold can be $9\times10^{-3}$. In some embodiments, the predetermined threshold can be $2\times10^{-5}$. In some embodiments, the predetermined threshold can be $5\times10^{-5}$. In some embodiments, the predetermined threshold can be $9\times10^{-5}$. In some embodiments, the predetermined threshold can be $2\times10^{-6}$. In some embodiments, the predetermined threshold can be $5\times10'$.

In some embodiments, prior to the tagging, the processing of the first sample and the second sample comprises partitioning at least a subset of the polynucleotides into at least two partitioned sets based on an epigenetic feature, thereby generating partitioned polynucleotides. In some embodiments, the partitioning comprises partitioning the nucleic acid molecules based on a differential binding affinity of the polynucleotides or the proteins associated with the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets may receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

In some embodiments, in addition to analyzing the sequencing reads based on at least one epigenetic feature, the sequencing reads are analyzed for detecting the presence of at least one somatic variation in the second sample. In those embodiments, the subject is classified (a) as positive for ctDNA, if the overall posterior probability for cancer presence is greater than or equal to the predetermined threshold or at least one somatic variation is detected in the second sample, or (b) as negative for ctDNA, if the overall posterior probability for cancer presence is less than the predetermined threshold and the somatic variation is not detected in the second sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags are attached to the nucleic acids by ligation of adapters to the nucleic acids, wherein the adapters comprise one or more tags.

Figure 3:
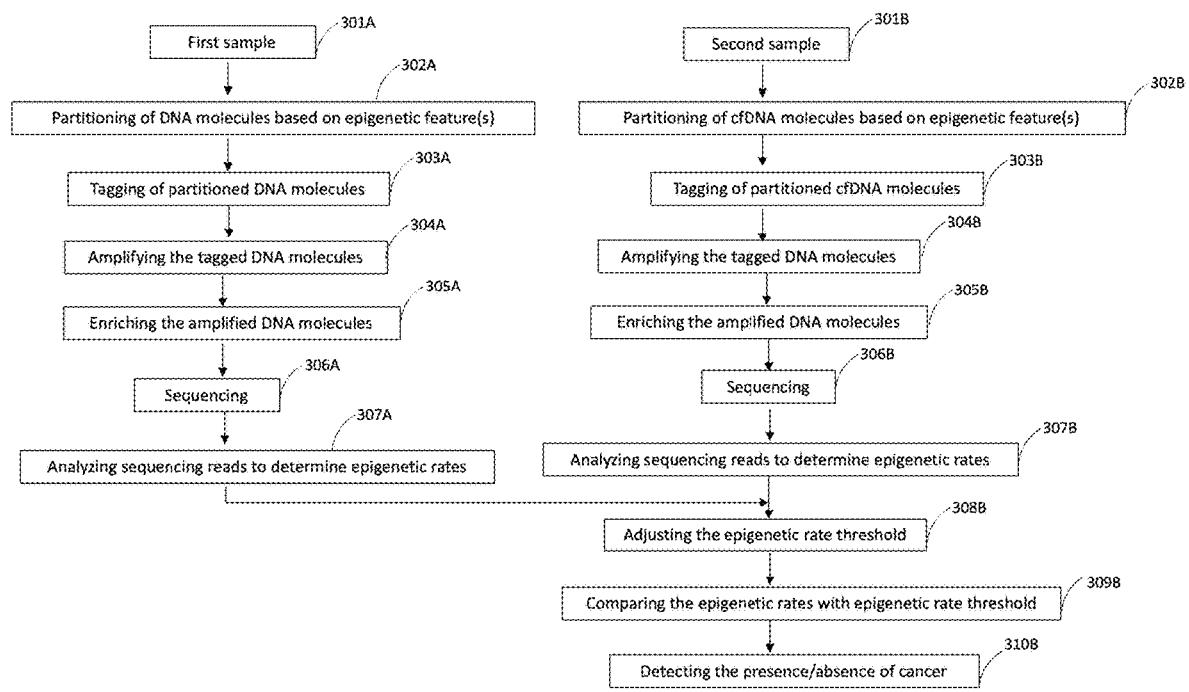
FIG. 3 is a flow chart representation of a method for detecting the presence or absence of cancer in a subject according to an embodiment of the disclosure.

FIG. 3 illustrates an example embodiment of a method 300 for detecting the presence or absence of cancer in a subject. In step 301A, a first sample from the subject is obtained at a first time point. In some embodiments, the first sample is a polynucleotide sample, extracted from a tumor tissue specimen (e.g., during surgery). In some embodiments, the tumor tissue specimen from which the first sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample and undergoes processing steps similar to the first sample. In some embodiments, the polynucleotides sample obtained from the tissue specimen is treated with fragmentase to fragment the polynucleotides into a fragments of size 100-200 bp in average. In some embodiments, the first sample is a cell-free polynucleotide sample, extracted from the blood sample (e.g., collected prior to the surgery).

In step 302A, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The first sample is then subjected to a series of processing steps (303A to 306A). The processing steps described here may be similar to the processing steps described in FIG. 1. All the embodiments and features of processing steps described in FIG. 1 can be applied here as well. In step 303A, a subset of the first sample is attached with tags to generate tagged parent polynucleotides. In step 304A, a subset of the tagged parent polynucleotides is amplified to generate progeny polynucleotides. In step 305A, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 306A, a subset of the enriched molecules is sequenced to generate a plurality of sequencing reads. The sequencing information obtained from the sequencing reads comprises sequences of the polynucleotide and the tags attached to the polynucleotide. In some embodiments, the sequencing of enriched molecules comprises next-generation sequencing. In some embodiments, the sequencing comprises bisulfate sequencing. In some embodiments, the sequencing comprises bisulfate-free methylation detection sequencing. In some embodiments, the sequencing comprises bisulfate-free methylation detection sequencing TAPS, ACE-seq, TAB-seq, or hmC-Seal.

In step 307A, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 can be applied here as well. These epigenetic rates are then utilized in analyzing the second sample obtained from the subject at a later time point (e.g., after the surgery).

In step 301B, the second sample from the subject is obtained at a second time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides. In step 302B, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The second sample is then subjected to a series of processing steps (303B to 306B). The processing steps of the second sample may be similar to that of the first sample. All the embodiments and features of processing steps described in FIG. 1 can be applied here as well. In step 303B, a subset of the second sample is attached with tags to generate tagged parent polynucleotides. In step 304B, a subset of the tagged parent polynucleotides is amplified to generate progeny polynucleotides. In step 305B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 306B, a subset of the enriched molecules is sequenced to generate a plurality of sequencing reads.

In step 307B, the sequencing reads mapped to a plurality of genomic regions are analyzed to determine the epigenetic rates for the plurality of genomic regions. All the embodiments and features of epigenetic features and epigenetic rate described in FIG. 1 can be applied here as well. In step 308B, the epigenetic rate threshold at a particular genomic region is adjusted based on the epigenetic rate of the first sample. Epigenetic rate threshold refers to a predetermined threshold of the epigenetic rate, which is used to determine the presence of tumor DNA (e.g., ctDNA) in a sample. For example, in the first sample if a particular genomic region of interest has a methylation rate of 100%, then the epigenetic rate threshold for the second sample need not be adjusted for that particular genomic region. But for another genomic region if the methylation rate of the first sample is 50%, then the epigenetic rate threshold for the second sample can be lowered. In some embodiments, the epigenetic rate threshold can be any value between 0 and 1. In some embodiments, the epigenetic rate threshold can be any value between 0 and 100. In some embodiments, the adjusted epigenetic rate threshold can be lower or greater than the previously determined epigenetic rate threshold. The epigenetic rate threshold can be determined based on a set of training samples (healthy donors and cancer patients/contrived samples) with known tumor fraction. The epigenetic rate threshold can be determined based on a set of training samples (healthy donors and cancer patients/contrived samples) with known tumor fraction. In step 309B, the epigenetic rate of the second sample for the plurality of genomic regions is then compared with the adjusted epigenetic rate threshold. In step 310B, the presence or absence of cancer is detected based on whether the subject is positive or negative for ctDNA. For example, if particular genomic region is hypermethylated in tumor, then if the epigenetic rate of the second sample at a particular genomic region is greater than the epigenetic rate threshold, then the subject is classified as being positive for ctDNA. In another example, if a particular genomic region is hypomethylated in tumor, then if the epigenetic rate of the second sample at a particular genomic region is lower than the epigenetic rate threshold, then the subject is classified as being positive for ctDNA. The epigenetic rate threshold can be set so as to accommodate embodiments that comprise hypomethylated genomic regions in tumor and hypermethylation genomic regions in tumor. In some embodiments, the subject is classified (i) as positive for ctDNA, if the epigenetic rate of the second sample in at least one genomic region is greater than or equal to the adjusted epigenetic rate threshold; or (ii) as negative for ctDNA, if the epigenetic rates for the plurality of genomic regions of the second sample is less than the adjusted epigenetic rate threshold.

In some embodiments, in addition to analyzing the sequencing reads based on at least one epigenetic feature, the sequencing reads are analyzed for detecting the presence of at least one somatic variation in the second sample. In those embodiments, the subject is classified (a) as positive for ctDNA, if the epigenetic rate of at least one genomic region of the second sample is greater than or equal to the adjusted epigenetic rate threshold or at least one somatic variation is detected in the second sample, or (b) as negative for ctDNA, if the epigenetic rate for all the genomic regions is less than the adjusted epigenetic rate threshold and the somatic variation is not detected in the second sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags are attached to the nucleic acids by ligation of adapters to the nucleic acids, wherein the adapters comprise one or more tags.

Figure 4:
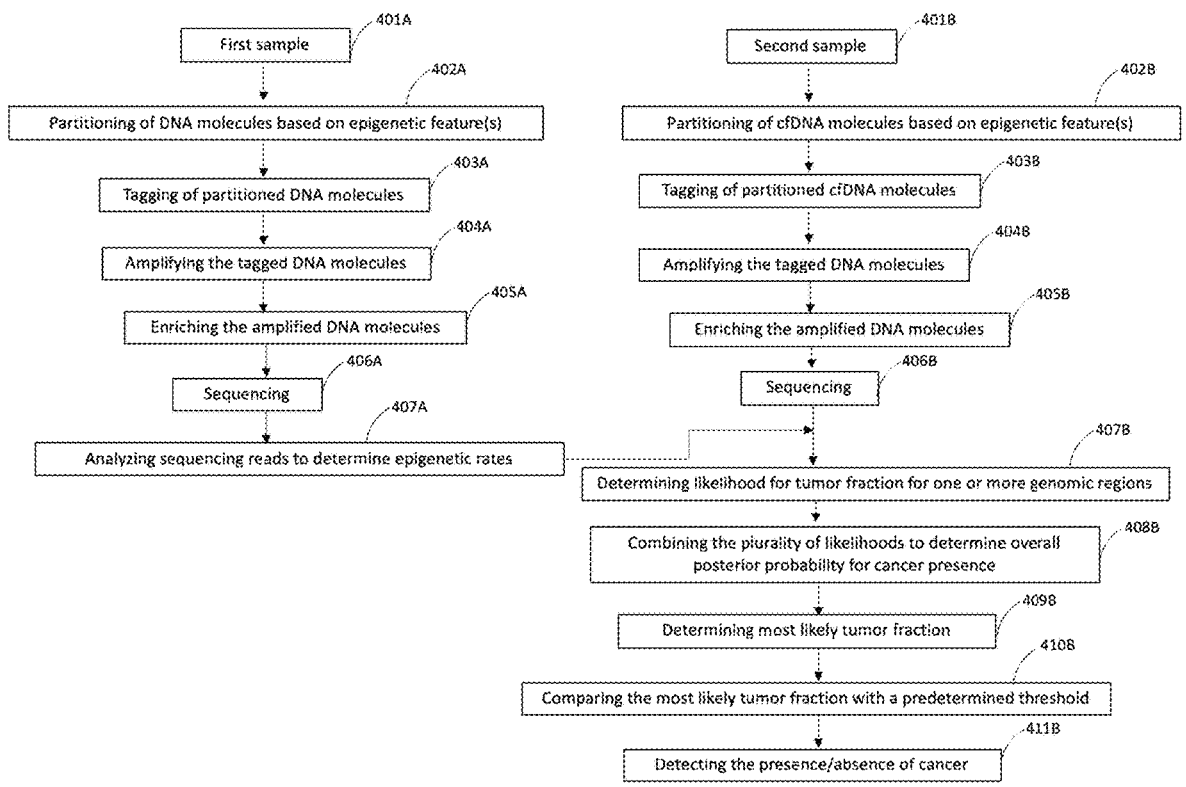
FIG. 4 is a flow chart representation of a method for detecting the presence or absence of cancer in a subject according to an embodiment of the disclosure.

FIG. 4 illustrates an example embodiment of a method 400 for detecting the presence or absence of cancer in a subject. In step 401A, a first sample from the subject is obtained at a first time point. In some embodiments, the first sample is a polynucleotide sample, extracted from a tumor tissue specimen (e.g., during surgery). In some embodiments, the tumor tissue specimen from which the first sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample. In some embodiments, the polynucleotides sample obtained from the tissue specimen is treated with fragmentase to fragment the polynucleotides into a fragments of size 100-200 bp in average. In some embodiments, the first sample is a cell-free polynucleotide sample, extracted from the blood sample (e.g., collected prior to the surgery).

In step 402A, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The first sample is then subjected to a series of processing steps (403A to 406A). The processing steps described here may be similar to the processing steps described in FIG. 1. All the embodiments and features of processing steps described in FIG. 1 and FIG. 2 can be applied here as well. In step 403A, a subset of the first sample is attached with tags to generate tagged parent polynucleotides. In step 404A, a subset of the tagged parent polynucleotides is amplified to generate progeny polynucleotides. In step 405A, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 406A, a subset of the enriched molecules is sequenced to generate a plurality of sequencing reads. The sequencing information obtained from the sequencing reads comprises sequence of the polynucleotide and the tags attached to the polynucleotide. In some embodiments, the sequencing of enriched molecules comprises next-generation sequencing. In some embodiments, the sequencing comprises bisulfate sequencing. In some embodiments, the sequencing comprises bisulfate-free methylation detection sequencing. In some embodiments, the sequencing comprises bisulfate-free methylation detection sequencing TAPS, ACE-seq, TAB-seq, or hmC-Seal.

In step 407A, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 can be applied here as well. These epigenetic rates are then utilized in analyzing the second sample obtained from the subject at a later time point (e.g., after the surgery).

In step 401B, the second sample from the subject is obtained at a second time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides. In step 402B, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The second sample is then subjected to a series of processing steps (403B to 406B). The processing steps of the second sample may be similar to that of the first sample. All the embodiments and features of processing steps described in FIG. 1 and FIG. 2 can be applied here as well. In step 403B, a subset of the second sample is attached with tags to generate tagged parent polynucleotides. In step 404B, a subset of the tagged parent polynucleotides is amplified to generate progeny polynucleotides. In step 405B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 406B, a subset of the enriched molecules is sequenced to generate a plurality of sequencing reads.

In step 407B, the sequencing reads mapped to a plurality of genomic regions are analyzed to determine a likelihood for tumor fraction for one or more of the plurality of genomic regions based on a predetermined set of epigenetic rates of the plurality of genomic regions for the second sample, a set of epigenetic characteristics for a group of cell-free polynucleotides in the second sample aligned to the plurality of genomic regions, and the epigenetic rate of the plurality of genomic regions for the first sample. In some embodiments, the predetermined set of epigenetic rates of the plurality of genomic regions of the second sample can be a set of at least 10, at least 50, at least 100, at least 200, at least 500 or at least 1000 epigenetic rates between 0 and 1. In some embodiments, if the epigenetic characteristic is methylation, the epigenetic characteristics comprises partitioning of the cfDNA molecule, number of CpG residues in the cfDNA molecule and the location (or offset) of the cfDNA molecule. In some embodiments, if the epigenetic feature is fragmentomic signal, then the epigenetic characteristics comprise length of the cfDNA molecules, the location (or offset) of the cfDNA molecule—start and/or end positions of the cfDNA molecules.

In step 408B, the plurality of likelihoods for tumor fraction of one or more of the plurality of genomic regions of the second sample is combined to determine an overall posterior probability for cancer presence. In some embodiments, the plurality of likelihoods for tumor fraction of a subset of the plurality of the genomic regions of the second sample is combined to determine the overall posterior probability for cancer presence. In some embodiments, the subset of the plurality of genomic regions in the second sample is selected based on the epigenetic rates of the first sample. In some embodiments, the subset of the plurality of genomic regions in the second sample comprise a genomic region with one highest epigenetic rate in the first sample, genomic regions with 2 highest epigenetic rates in the first sample, genomic regions with 5 highest epigenetic rates in the first sample, genomic regions with 10 highest epigenetic rates in the first sample, genomic regions with 20 highest epigenetic rates in the first sample, genomic regions with 30 highest epigenetic rates in the first sample, genomic regions with 40 highest epigenetic rates in the first sample, genomic regions with 50 highest epigenetic rates in the first sample, genomic regions with 60 highest epigenetic rates in the first sample, genomic regions with 70 highest epigenetic rates in the first sample, genomic regions with 80 highest epigenetic rates in the first sample, genomic regions with 90 highest epigenetic rates in the first sample, genomic regions with 100 highest epigenetic rates in the first sample, genomic regions with 150 highest epigenetic rates in the first sample, genomic regions with 200 highest epigenetic rates in the first sample, genomic regions with at least 200 highest epigenetic rates in the first sample, genomic regions with at least 300 highest epigenetic rates in the first sample, genomic regions with at least 400 highest epigenetic rates in the first sample, genomic regions with at least 500 highest epigenetic rates in the first sample, genomic regions with at least 600 highest epigenetic rates in the first sample, genomic regions with at least 700 highest epigenetic rates in the first sample, genomic regions with at least 800 highest epigenetic rates in the first sample, genomic regions with at least 900 highest epigenetic rates in the first sample, genomic regions with at least 1000 highest epigenetic rates in the first sample, genomic regions with at least 5000 highest epigenetic rates in the first sample or genomic regions with at least 10,000 highest epigenetic rates in the first sample. In some embodiments, the subset of the plurality of genomic regions in the second sample comprise genomic regions with 5 highest epigenetic rates in the first sample. In some embodiments, the subset of the plurality of genomic regions in the second sample comprise genomic regions with 10 highest epigenetic rates in the first sample. In some embodiments, the subset of the plurality of genomic regions in the second sample comprise genomic regions with 25 highest epigenetic rates in the first sample. In some embodiments, the subset of the plurality of genomic regions in the second sample comprise genomic regions with 50 highest epigenetic rates in the first sample. In some embodiments, the subset of the plurality of genomic regions in the second sample comprise genomic regions with 100 highest epigenetic rates in the first sample. In some embodiments, the subset of the plurality of genomic regions in the second sample comprise genomic regions with 200 highest epigenetic rates in the first sample. In some embodiments, the subset of the plurality of genomic regions in the second sample comprise genomic regions with 250 highest epigenetic rates in the first sample. In some embodiments, the subset of the plurality of genomic regions in the second sample comprise genomic regions with 500 highest epigenetic rates in the first sample. In some embodiments, the subset of the plurality of genomic regions in the second sample comprise genomic regions with 1000 highest epigenetic rates in the first sample. In some embodiments, the subset of the plurality of genomic regions in the second sample comprise genomic regions with 5000 highest epigenetic rates in the first sample. In some embodiments, the subset of the plurality of genomic regions in the second sample comprise genomic regions with 10,000 highest epigenetic rates in the first sample. In some embodiments, the subset of the plurality of genomic regions in the second sample comprise genomic regions with at least 5 highest epigenetic rates in the first sample. In some embodiments, the subset of the plurality of genomic regions in the second sample comprise genomic regions with at least 10 highest epigenetic rates in the first sample. In some embodiments, the subset of the plurality of genomic regions in the second sample comprise genomic regions with at least 25 highest epigenetic rates in the first sample. In some embodiments, the subset of the plurality of genomic regions in the second sample comprise genomic regions with at least 50 highest epigenetic rates in the first sample. In some embodiments, the subset of the plurality of genomic regions in the second sample comprise genomic regions with at least 100 highest epigenetic rates in the first sample. In some embodiments, the subset of the plurality of genomic regions in the second sample comprise genomic regions with at least 200 highest epigenetic rates in the first sample. In step 409B, the overall posterior probability is used to determine the most likely estimate of tumor fraction. In step 410B, the most likely estimate of tumor fraction is compared with a predetermined threshold. In step 411B, the presence or absence of cancer is detected based on whether the subject is positive or negative for ctDNA. The subject is classified (i) as positive for ctDNA, if the most likely estimate of tumor fraction is greater than or equal to the predetermined threshold; or (ii) as negative for ctDNA, if the most likely estimate of tumor fraction is less than the predetermined threshold. In some embodiments, the predetermined threshold can be any value between 0 and 1. In some embodiments, the predetermined threshold can be less than 0.5, 0.5, 0.6, 0.7, 0.75, 0.8, 0.9, 0.91, 0.92, 0.93, 0.94, 0.95, 0.96, 0.97, 0.98, or 0.99. In some embodiments, the predetermined threshold can be 0.1. In some embodiments, the predetermined threshold can be 0.2. In some embodiments, the predetermined threshold can be 0.3. In some embodiments, the predetermined threshold can be 0.4. In some embodiments, the predetermined threshold can be 0.5. In some embodiments, the predetermined threshold can be 0.6. In some embodiments, the predetermined threshold can be 0.7. In some embodiments, the predetermined threshold can be 0.8. In some embodiments, the predetermined threshold can be 0.9. In some embodiments, the predetermined threshold can be 0.95. In some embodiments, the predetermined threshold can be 0.99. In some embodiments, the predetermined threshold can be any value between 0 and 1. In some embodiments, the predetermined threshold can be less than 0.5, 0.5, 0.6, 0.7, 0.75, 0.8, 0.9, 0.91, 0.92, 0.93, 0.94, 0.95, 0.96, 0.97, 0.98, or 0.99. In some embodiments, the predetermined threshold can be any value between $10^{-5}$ to 10'. In some embodiments, the predetermined threshold can be any value between $10^{-7}$ to $10^{-2}$. In some embodiments, the predetermined threshold can be any value between $10^{-6}$ to $10^{-2}$. In some embodiments, the predetermined threshold can be any value between $10^{-5}$ to 0.1. In some embodiments, the predetermined threshold can be any value between $10^{-4}$ to $10^{-3}$. In some embodiments, the predetermined threshold can be $2 \times 10^{-4}$. In some embodiments, the predetermined threshold can be $3 \times 10^{-4}$. In some embodiments, the predetermined threshold can be $4 \times 10^{-4}$. In some embodiments, the predetermined threshold can be $5 \times 10^{-4}$. In some embodiments, the predetermined threshold can be $6 \times 10^{-4}$. In some embodiments, the predetermined threshold can be $7 \times 10^{-4}$. In some embodiments, the predetermined threshold can be $8 \times 10^{-4}$. In some embodiments, the predetermined threshold can be $9 \times 10^{-3}$. In some embodiments, the predetermined threshold can be $2 \times 10^{-3}$. In some embodiments, the predetermined threshold can be $5 \times 10^{-3}$. In some embodiments, the predetermined threshold can be $9 \times 10^{-3}$. In some embodiments, the predetermined threshold can be $2 \times 10^{-5}$. In some embodiments, the predetermined threshold can be $5 \times 10^{-5}$. In some embodiments, the predetermined threshold can be $9 \times 10^{-5}$. In some embodiments, the predetermined threshold can be $2 \times 10^{-6}$. In some embodiments, the predetermined threshold can be $5 \times 10^{-6}$.

In some embodiments, in addition to analyzing the sequencing reads based on at least one epigenetic feature, the sequencing reads are analyzed for detecting the presence of at least one somatic variation in the second sample. In those embodiments, the subject is classified (a) as positive for ctDNA, if the most likely tumor fraction is greater than or equal to the predetermined threshold or at least one somatic variation is detected in the second sample, or (b) as negative for ctDNA, if the most likely tumor fraction is less than the predetermined threshold and the somatic variation is not detected in the second sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags are attached to the nucleic acids by ligation of adapters to the nucleic acids, wherein the adapters comprise one or more tags.

Figure 5:
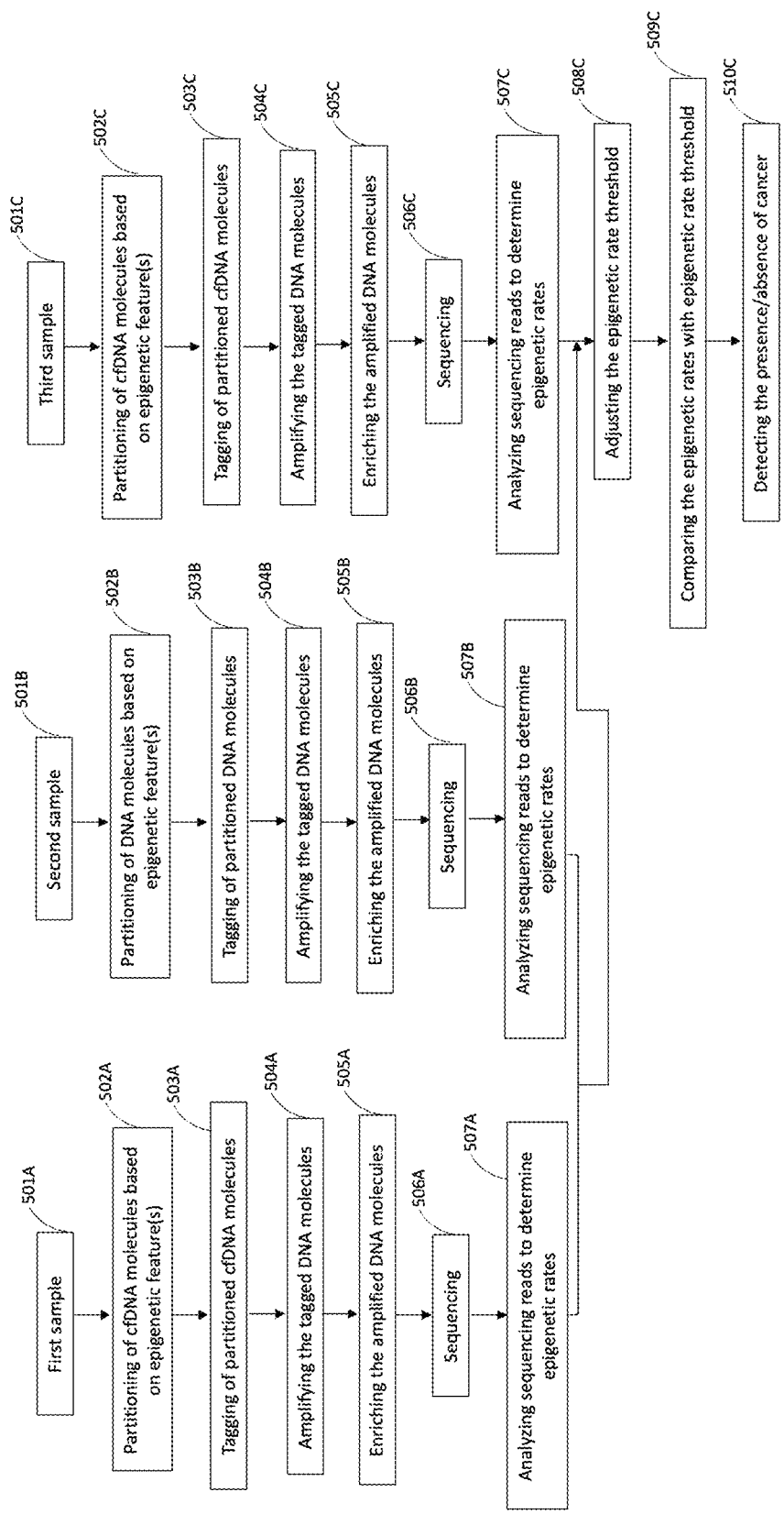
FIG. 5 is a flow chart representation of a method for detecting the presence or absence of cancer in a subject according to an embodiment of the disclosure.

FIG. 5 illustrates an example embodiment of a method 500 for detecting the presence or absence of cancer in a subject. In step 501A, a first sample from the subject is obtained at a first time point. In some embodiments, the first sample is a cell-free polynucleotide sample, extracted from the blood sample (e.g., collected prior to the surgery).

In step 502A, at least a subset of the cell-free polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The first sample is then subjected to a series of processing steps (503A to 506A). The processing steps described here may be similar to the processing steps described in FIG. 1. All the embodiments and features of processing steps described in FIG. 1 can be applied here as well. In step 503A, a subset of the first sample is attached with tags to generate tagged parent polynucleotides. In step 504A, a subset of the tagged parent polynucleotides is amplified to generate progeny polynucleotides. In step 505A, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 506A, a subset of the enriched molecules is sequenced to generate a plurality of sequencing reads. The sequencing information obtained from the sequencing reads comprises sequences of the polynucleotide and the tags attached to the polynucleotide. In some embodiments, the sequencing of enriched molecules comprises next-generation sequencing. In some embodiments, the sequencing comprises bisulfite sequencing. In some embodiments, the sequencing comprises bisulfite-free methylation detection sequencing. In some embodiments, the sequencing comprises bisulfite-free methylation detection sequencing TAPS, ACE-seq, TAB-seq, or hmC-Seal.

In step 507A, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 can be applied here as well. These epigenetic rates are then utilized in analyzing the third sample obtained from the subject at a later time point (e.g., after the surgery).

In step 501B, a second sample from the subject is obtained at a second time point. In some embodiments, the second sample is a polynucleotide sample, extracted from a tumor tissue specimen (e.g., during surgery). In some embodiments, the tumor tissue specimen from which the second sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample. In some embodiments, the polynucleotides sample obtained from the tissue specimen is treated with fragmentase to fragment the polynucleotides into a fragments of size 100-200 bp in average.

In step 502B, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The second sample is then subjected to a series of processing steps (503B to 506B). The processing steps described here may be similar to the processing steps described in FIG. 1. All the embodiments and features of processing steps described in FIG. 1 can be applied here as well. In step 503B, a subset of the second sample is attached with tags to generate tagged parent polynucleotides. In step 504B, a subset of the tagged parent polynucleotides is amplified to generate progeny polynucleotides. In step 505B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 506B, a subset of the enriched molecules is sequenced to generate a plurality of sequencing reads. The sequencing information obtained from the sequencing reads comprises sequences of the polynucleotide and the tags attached to the polynucleotide. In some embodiments, the sequencing of enriched molecules comprises next-generation sequencing. In some embodiments, the sequencing comprises bisulfate sequencing. In some embodiments, the sequencing comprises bisulfate-free methylation detection sequencing. In some embodiments, the sequencing comprises bisulfate-free methylation detection sequencing TAPS, ACE-seq, TAB-seq, or hmC-Seal.

In step 507B, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 can be applied here as well. These epigenetic rates are then utilized in analyzing the third sample obtained from the subject at a later time point (e.g., after the surgery).

In step 501C, the third sample from the subject is obtained at a third time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides. In step 502C, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The third sample is then subjected to a series of processing steps (503C to 506C). The processing steps of the third sample may be similar to that of the first sample. All the embodiments and features of processing steps described in FIG. 1 can be applied here as well. In step 503C, a subset of the third sample is attached with tags to generate tagged parent polynucleotides. In step 504C, a subset of the tagged parent polynucleotides is amplified to generate progeny polynucleotides. In step 505C, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 506C, a subset of the enriched molecules is sequenced to generate a plurality of sequencing reads.

In step 507C, the sequencing reads are analyzed to determine the epigenetic rates for the plurality of genomic regions. All the embodiments and features of epigenetic features and epigenetic rate described in FIG. 1 can be applied here as well. In step 508C, the epigenetic rate threshold at a particular genomic region is adjusted based on the epigenetic rate of the first sample and the epigenetic rate of the second sample. Epigenetic rate threshold refers to a predetermined threshold of the epigenetic rate, which is used to determine the presence of tumor DNA in a sample. For example, if a particular genomic region of interest has a methylation rate of 100% in both the first sample and second sample, then the epigenetic rate threshold for the third sample need not be adjusted for that particular genomic region. But for another genomic region if the methylation rate of the first sample is 50% and the methylation rate of the second person is 45%, then the epigenetic rate threshold for the third sample can be lowered. In some embodiments, the epigenetic rate threshold can be any value between 0 and 1. In some embodiments, the epigenetic rate threshold can be any value between 0 and 100. In some embodiments, the adjusted epigenetic rate threshold can be lower or greater than the previously determined epigenetic rate threshold. The epigenetic rate threshold can be determined based on a set of training samples (healthy donors and cancer patients/contrived samples) with known tumor fraction. In step 509C, the epigenetic rate of the third sample for the plurality of genomic regions is then compared with the adjusted epigenetic rate threshold. In step 510C, the presence or absence of cancer is detected based on whether the subject is positive or negative for ctDNA. For example, if particular genomic region is hypermethylated in tumor, then if the epigenetic rate of the third sample at a particular genomic region is greater than the epigenetic rate threshold, then the subject is classified as being positive for ctDNA. In another example, if a particular genomic region is hypomethylated in tumor, then if the epigenetic rate of the third sample at a particular genomic region is lower than the epigenetic rate threshold, then the subject is classified as being positive for ctDNA. The epigenetic rate threshold can be set so as to accommodate embodiments that comprise hypomethylated genomic regions in tumor and hypermethylation genomic regions in tumor. In some embodiments, the subject is classified (i) as positive for ctDNA, if the epigenetic rate in at least one genomic region of the third sample is greater than or equal to the adjusted epigenetic rate threshold; or (ii) as negative for ctDNA, if the epigenetic rates for the plurality of genomic regions of the third sample is less than the adjusted epigenetic rate threshold.

In some embodiments, in addition to analyzing the sequencing reads based on at least one epigenetic feature, the sequencing reads are analyzed for detecting the presence of at least one somatic variation in the third sample. In those embodiments, the subject is classified (a) as positive for ctDNA, if the epigenetic rate of at least one genomic region of the third sample is greater than or equal to the adjusted epigenetic rate threshold or at least one somatic variation is detected in the third sample, or (b) as negative for ctDNA, if the epigenetic rate for all the genomic regions of the third sample is less than the adjusted epigenetic rate threshold and the somatic variation is not detected in the third sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags are attached to the nucleic acids by ligation of adapters to the nucleic acids, wherein the adapters comprise one or more tags.

Figure 6:
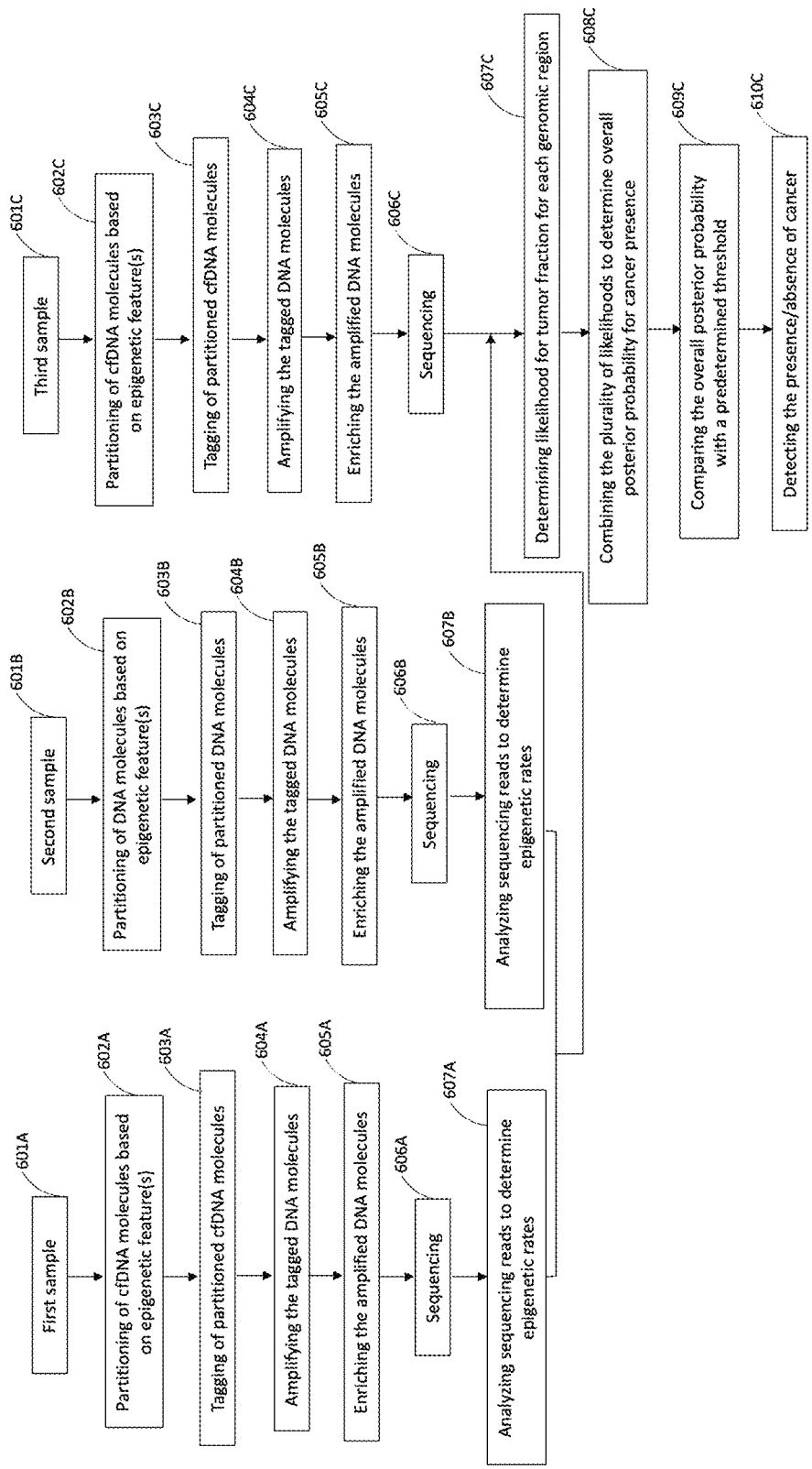
FIG. 6 is a flow chart representation of a method for detecting the presence or absence of cancer in a subject according to an embodiment of the disclosure.

FIG. 6 illustrates an example embodiment of a method 600 for detecting the presence or absence of cancer in a subject. In step 601A, a first sample from the subject is obtained at a first time point. In some embodiments, the first sample is a cell-free polynucleotide sample, extracted from the blood sample (e.g., collected prior to the surgery).

In step 602A, at least a subset of the cell-free polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The first sample is then subjected to a series of processing steps (603A to 606A). The processing steps described here may be similar to the processing steps described in FIG. 1. All the embodiments and features of processing steps described in FIG. 1 and FIG. 2 can be applied here as well. In step 603A, a subset of the first sample is attached with tags to generate tagged parent polynucleotides. In step 604A, a subset of the tagged parent polynucleotides is amplified to generate progeny polynucleotides. In step 605A, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 606A, a subset of the enriched molecules is sequenced to generate a plurality of sequencing reads. The sequencing information obtained from the sequencing reads comprises sequences of the polynucleotide and the tags attached to the polynucleotide. In some embodiments, the sequencing of enriched molecules comprises next-generation sequencing. In some embodiments, the sequencing comprises bisulfite sequencing. In some embodiments, the sequencing comprises bisulfite-free methylation detection sequencing. In some embodiments, the sequencing comprises bisulfite-free methylation detection sequencing TAPS, ACE-seq, TAB-seq, or hmC-Seal.

In step 607A, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 and FIG. 2 can be applied here as well. These epigenetic rates are then utilized in analyzing the third sample obtained from the subject at a later time point (e.g., after the surgery).

In step 601B, a second sample from the subject is obtained at a second time point. In some embodiments, the second sample is a polynucleotide sample, extracted from a tumor tissue specimen (e.g., during surgery). In some embodiments, the tumor tissue specimen from which the second sample is extracted can be a frozen tissue sample or a formalin-fixed paraffin-embedded (FFPE) sample. In some embodiments, a polynucleotide sample, extracted from an adjacent normal tissue specimen at the first time point along with the first sample (i.e., polynucleotide sample extracted from a tumor tissue specimen). In these embodiments, the adjacent normal tissue specimen is collected to identify changes in the epigenetic features (e.g. changes in methylation pattern or changes in fragmentomic signal) that are tumor tissue specific in the first sample. In some embodiments, the polynucleotides sample obtained from the tissue specimen is treated with fragmentase to fragment the polynucleotides into a fragments of size 100-200 bp in average. In step 602B, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over representative or under representative of modifications). In some embodiments, each of the plurality of partitioned sets is differentially tagged. The tagged partitioned sets are then pooled together for collective sample preparation, enrichment, and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The second sample is then subjected to a series of processing steps (603B to 606B). The processing steps described here may be similar to the processing steps described in FIG. 1. All the embodiments and features of processing steps described in FIG. 1 and FIG. 2 can be applied here as well. In step 603B, a subset of the second sample is attached with tags to generate tagged parent polynucleotides. In step 604B, a subset of the tagged parent polynucleotides is amplified to generate progeny polynucleotides. In step 605B, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 606B, a subset of the enriched molecules is sequenced to generate a plurality of sequencing reads. The sequencing information obtained from the sequencing reads comprises sequences of the polynucleotide and the tags attached to the polynucleotide. In some embodiments, the sequencing of enriched molecules comprises next-generation sequencing. In some embodiments, the sequencing comprises bisulfate sequencing. In some embodiments, the sequencing comprises bisulfate-free methylation detection sequencing. In some embodiments, the sequencing comprises bisulfate-free methylation detection sequencing TAPS, ACE-seq, TAB-seq, or hmC-Seal.

In step 607B, the sequencing reads mapped to a plurality of genomic regions are analyzed based on one or more epigenetic features, and the epigenetic rates for the plurality of genomic regions are determined. All the embodiments and features of epigenetic features and epigenetic rate described in FIG. 1 and FIG. 2 can be applied here as well. These epigenetic rates are then utilized in analyzing the third sample obtained from the subject at a later time point (e.g., after the surgery).

In step 601C, the third sample from the subject is obtained at a third time point. In some embodiments, the second sample is a cell-free polynucleotide sample, extracted from the blood sample (e.g., collected post-surgery). In some embodiments, peripheral blood mononuclear cell (PBMC) sample is also obtained along the cell-free polynucleotide sample at the second time point. In some embodiments, the PBMC sample is processed and analyzed similar to the second sample and is used to normalize the contribution of blood cells in the epigenetic rate of the cell-free polynucleotides.

In step 602C, at least a subset of the polynucleotides is partitioned into at least two partitioned sets based on an epigenetic feature, thereby generating partitioned polynucleotides. In some embodiments, the partitioning comprises partitioning the nucleic acid molecules based on a differential binding affinity of the polynucleotides to a binding agent that preferentially binds to polynucleotides comprising nucleotides with chemical modification (e.g., methylation). In some embodiments, the binding agent comprises methyl binding domain (MBDs) and methyl binding proteins (MBPs). In those embodiments, the nucleic acids are partitioned based on the different levels of methylation (e.g., different number of methylated nucleotides). In some embodiments, the nucleic acids can be partitioned into two or more partitioned sets (e.g., at least 3, 4, 5, 6, or 7 partitioned sets). In some embodiments, the partitioned sets are representatives of nucleic acids having different extents of modifications (over-representative or under-representative of modifications). In some embodiments, each of the plurality of partitioned sets is differentially tagged. The tagged partitioned sets are then pooled together for collective sample preparation, enrichment and/or sequencing. Differential tagging of the partitioned sets helps in keeping track of the nucleic acid molecules belonging to a particular partitioned set. The tags may be provided as components of adapters. The nucleic acid molecules in different partitioned sets receive different tags that can distinguish members of one partitioned set from another. The tags linked to nucleic acid molecules of the same partition set can be the same or different from one another. For example, if the tags linked to nucleic acid molecules of the same partition set are different from one another, the tags can have part of their sequence in common so as to identify the molecules to which they are attached as being of a particular partitioned set.

The third sample is then subjected to a series of processing steps (603C to 606C). The processing steps of the third sample may be similar to that of the first sample. All the embodiments and features of processing steps described in FIG. 1 and FIG. 2 can be applied here as well. In step 603C, a subset of the third sample is attached with tags to generate tagged parent polynucleotides. In step 604C, a subset of the tagged parent polynucleotides is amplified to generate progeny polynucleotides. In step 605C, a subset of the progeny polynucleotides that belong to a set of genomic regions of interest is enriched to generate enriched molecules. In some embodiments, an amplification step is performed to amplify the enriched polynucleotides prior to sequencing. In some embodiments, the primers used in the amplification step prior to enrichment or the amplification step prior to sequencing, comprise at least one sample index to enable multiplex sequencing. In step 606C, a subset of the enriched molecules is sequenced to generate a plurality of sequencing reads.

In step 607C, the sequencing reads are analyzed to determine a likelihood for tumor fraction for one or more of the plurality of genomic regions based on a predetermined set of epigenetic rates of the plurality of genomic regions for the third sample, a set of epigenetic characteristics for a group of cell-free polynucleotides in the third sample aligned to the plurality of genomic regions, the epigenetic rate of the plurality of genomic regions of the first sample and the epigenetic rate of the plurality of the genomic regions of the second sample. In some embodiments, the predetermined set of epigenetic rates of the plurality of genomic regions of the third sample can be a set of at least 10, at least 50, at least 100, at least 200, at least 500 or at least 1000 epigenetic rates between 0 and 1. In some embodiments, if the epigenetic characteristic is methylation, the epigenetic characteristics comprises partitioning of the cfDNA molecule, number of CpG residues in the cfDNA molecule and the location (or offset) of the cfDNA molecule. In some embodiments, if the epigenetic feature is fragmentomic signal, then the epigenetic characteristics comprise length of the cfDNA molecules, the location (or offset) of the cfDNA molecule—start and/or end positions of the cfDNA molecules.

In step 608C, the plurality of likelihoods for tumor fraction of one or more of the plurality of genomic regions of the third sample is combined to determine an overall posterior probability for cancer presence. In some embodiments, the plurality of likelihoods for tumor fraction of a subset of the plurality of the genomic regions of the third sample is combined to determine the overall posterior probability for cancer presence. In some embodiments, the subset of the plurality of genomic regions in the third sample is selected based on the epigenetic rates of the first sample and/or second sample. In some embodiments, the subset of the plurality of genomic regions in the third sample comprise a genomic region with one highest epigenetic rate in the first sample and/or second sample, genomic regions with 2 highest epigenetic rates in the first sample and/or second sample, genomic regions with 5 highest epigenetic rates in the first sample and/or second sample, genomic regions with 10 highest epigenetic rates in the first sample and/or second sample, genomic regions with 20 highest epigenetic rates in the first sample and/or second sample, genomic regions with 30 highest epigenetic rates in the first sample and/or second sample, genomic regions with 40 highest epigenetic rates in the first sample and/or second sample, genomic regions with 50 highest epigenetic rates in the first sample and/or second sample, genomic regions with 60 highest epigenetic rates in the first sample and/or second sample, genomic regions with 70 highest epigenetic rates in the first sample and/or second sample, genomic regions with 80 highest epigenetic rates in the first sample and/or second sample, genomic regions with 90 highest epigenetic rates in the first sample and/or second sample, genomic regions with 100 highest epigenetic rates in the first sample and/or second sample, genomic regions with 150 highest epigenetic rates in the first sample and/or second sample, genomic regions with 200 highest epigenetic rates in the first sample and/or second sample, genomic regions with at least 250 highest epigenetic rates in the first sample and/or second sample, genomic regions with at least 300 highest epigenetic rates in the first sample and/or second sample, genomic regions with at least 400 highest epigenetic rates in the first sample and/or second sample, genomic regions with at least 500 highest epigenetic rates in the first sample and/or second sample, genomic regions with at least 600 highest epigenetic rates in the first sample and/or second sample, genomic regions with at least 700 highest epigenetic rates in the first sample and/or second sample, genomic regions with at least 800 highest epigenetic rates in the first sample and/or second sample, genomic regions with at least 900 highest epigenetic rates in the first sample and/or second sample, genomic regions with at least 1000 highest epigenetic rates in the first sample and/or second sample, genomic regions with at least 5000 highest epigenetic rates in the first sample and/or second sample or genomic regions with at least 10,000 highest epigenetic rates in the first sample and/or second sample. In some embodiments, the subset of the plurality of genomic regions in the third sample comprise genomic regions with 5 highest epigenetic rates in the first sample and/or second sample. In some embodiments, the subset of the plurality of genomic regions in the third sample comprise genomic regions with 10 highest epigenetic rates in the first sample and/or second sample. In some embodiments, the subset of the plurality of genomic regions in the third sample comprise genomic regions with 25 highest epigenetic rates in the first sample and/or second sample. In some embodiments, the subset of the plurality of genomic regions in the third sample comprise genomic regions with 50 highest epigenetic rates in the first sample and/or second sample. In some embodiments, the subset of the plurality of genomic regions in the third sample comprise genomic regions with 100 highest epigenetic rates in the first sample and/or second sample. In some embodiments, the subset of the plurality of genomic regions in the third sample comprise genomic regions with 200 highest epigenetic rates in the first sample and/or second sample. In some embodiments, the subset of the plurality of genomic regions in the third sample comprise genomic regions with 250 highest epigenetic rates in the first sample and/or second sample. In some embodiments, the subset of the plurality of genomic regions in the third sample comprise genomic regions with 500 highest epigenetic rates in the first sample and/or second sample. In some embodiments, the subset of the plurality of genomic regions in the third sample comprise genomic regions with 1000 highest epigenetic rates in the first sample and/or second sample. In some embodiments, the subset of the plurality of genomic regions in the third sample comprise genomic regions with 5000 highest epigenetic rates in the first sample and/or second sample. In some embodiments, the subset of the plurality of genomic regions in the third sample comprise genomic regions with 10,000 highest epigenetic rates in the first sample and/or second sample. In some embodiments, the subset of the plurality of genomic regions in the third sample comprise genomic regions with at least 5 highest epigenetic rates in the first sample and/or second sample. In some embodiments, the subset of the plurality of genomic regions in the third sample comprise genomic regions with at least 10 highest epigenetic rates in the first sample and/or second sample. In some embodiments, the subset of the plurality of genomic regions in the third sample comprise genomic regions with at least 25 highest epigenetic rates in the first sample and/or second sample. In some embodiments, the subset of the plurality of genomic regions in the third sample comprise genomic regions with at least 50 highest epigenetic rates in the first sample and/or second sample. In some embodiments, the subset of the plurality of genomic regions in the third sample comprise genomic regions with at least 100 highest epigenetic rates in the first sample and/or second sample. In some embodiments, the subset of the plurality of genomic regions in the third sample comprise genomic regions with at least 200 highest epigenetic rates in the first sample and/or second sample. In step 609C, the overall posterior probability is compared with a predetermined threshold. In step 610C, the presence or absence of cancer is detected based on whether the subject is positive or negative for ctDNA. The subject is classified (i) as positive for ctDNA, if the overall posterior probability is greater than the predetermined threshold; or (ii) as negative for ctDNA, if the overall posterior probability is less than the predetermined threshold. In some embodiments, the predetermined threshold can be any value between 0 and 1. In some embodiments, the predetermined threshold can be less than 0.5, 0.5, 0.6, 0.7, 0.75, 0.8, 0.9, 0.91, 0.92, 0.93, 0.94, 0.95, 0.96, 0.97, 0.98, or 0.99. In some embodiments, the predetermined threshold can be 0.1. In some embodiments, the predetermined threshold can be 0.2. In some embodiments, the predetermined threshold can be 0.3. In some embodiments, the predetermined threshold can be 0.4. In some embodiments, the predetermined threshold can be 0.5. In some embodiments, the predetermined threshold can be 0.6. In some embodiments, the predetermined threshold can be 0.7. In some embodiments, the predetermined threshold can be 0.8. In some embodiments, the predetermined threshold can be 0.9. In some embodiments, the predetermined threshold can be 0.95. In some embodiments, the predetermined threshold can be 0.99.

In some embodiments, in addition to analyzing the sequencing reads based on at least one epigenetic feature, the sequencing reads are analyzed for detecting the presence of at least one somatic variation in the third sample. In those embodiments, the subject is classified (a) as positive for ctDNA, if the overall posterior probability for cancer presence is greater than or equal to the predetermined threshold or at least one somatic variation is detected in the third sample, or (b) as negative for ctDNA, if the overall posterior probability for cancer presence is less than the predetermined threshold and the somatic variation is not detected in the third sample. In some embodiments, the somatic variation comprises a single nucleotide variation (SNV), insertion or deletion (indel), copy number variation (CNV), gene fusion, or combination thereof.

In some embodiments, the tagging comprises attaching a set of tags (or barcodes) to the nucleic acids to produce a population of tagged nucleic acids, wherein the tagged nucleic acids comprise one or more tags. In some embodiments, the set of tags are attached to the nucleic acids by ligation of adapters to the nucleic acids, wherein the adapters comprise one or more tags.

II. General Features of the Methods

A. Samples

A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, and urine. Samples may be bodily fluids, such as blood and fractions thereof, and urine. Such samples can include nucleic acids shed from tumors. The nucleic acids can include DNA and RNA, and can be in double- and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a bodily fluid for analysis can be plasma or serum containing cell-free nucleic acids, e.g., cell-free DNA (cfDNA).

In some embodiments, the sample volume of bodily fluid taken from a subject depends on the desired read depth for sequenced regions. Examples of volumes are about 0.4-40 milliliters (mL), about 5-20 mL, about 10-20 mL. For example, the volume can be about 0.5 mL, about 1 mL, about 5 mL, about 10 mL, about 20 mL, about 30 mL, about 40 mL, or more milliliters. A volume of sampled plasma is typically between about 5 mL to about 20 mL.

The sample can comprise various amounts of nucleic acid. Typically, the amount of nucleic acid in a given sample is equates with multiple genome equivalents. For example, a sample of about 30 nanograms (ng) DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Example amounts of cell-free nucleic acids in a sample before amplification typically range from about 1 femtogram (fg) to about 1 microgram (μg), e.g., about 1 picogram (pg) to about 200 nanograms (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In some embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides length (in samples from human subjects) and a second minor peak in a range between about 240 nucleotides to about 440 nucleotides in length. In some embodiments, cell-free nucleic acids are from about 160 nucleotides to about 180 nucleotides in length, or from about 320 nucleotides to about 360 nucleotides in length, or from about 440 nucleotides to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some embodiments, partitioning includes techniques such as centrifugation or filtration. Alternatively, cells in bodily fluids may be lysed, and cell-free and cellular nucleic acids may be processed together. Generally, after addition of buffers and wash steps, cell-free nucleic acids may be precipitated with, for example, an alcohol. In some embodiments, additional clean-up steps are used, such as silica-based columns to remove contaminants or salts. Non-specific bulk carrier nucleic acids, for example, are optionally added throughout the reaction to optimize aspects of the example procedure, such as yield. After such processing, samples typically include various forms of nucleic acids including double-stranded DNA, single-stranded DNA and/or single-stranded RNA. Optionally, single-stranded DNA and/or single-stranded RNA are converted to double-stranded forms so that they are included in subsequent processing and analysis steps.

B. Partitioning and Tagging

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-unique molecular barcodes in combination with endogenous sequence information (e.g., the beginning (start) and/or end (stop) genomic location/position corresponding to the sequence of the original nucleic acid molecule in the sample, start and stop genomic positions corresponding to the sequence of the original nucleic acid molecule in the sample, the beginning (start) and/or end (stop) genomic location/position of the sequence read that is mapped to the reference sequence, start and stop genomic positions of the sequence read that is mapped to the reference sequence, sub-sequences of sequence reads at one or both ends, length of sequence reads, and/or length of the original nucleic acid molecule in the sample) typically allows for the assignment of a unique identity to a particular molecule. In some embodiments, beginning region comprises the first 1, first 2, the first 5, the first 10, the first 15, the first 20, the first 25, the first 30 or at least the first 30 base positions at the 5' end of the sequencing read that align to the reference sequence. In some embodiments, the end region comprises the last 1, last 2, the last 5, the last 10, the last 15, the last 20, the last 25, the last 30 or at least the last 30 base positions at the 3' end of the sequencing read that align to the reference sequence. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcode sequences, or from about 5 to about 150 different molecular barcode sequences, or from about 20 to about 50 different molecular barcode sequences, ligated to both ends of a target molecule. Alternatively, from about 25 to about 1,000,000 different molecular barcode sequences may be used. For example, 20-50× 20-50 molecular barcode sequences (i.e., one of the 20-50 different molecular barcode sequences can be attached to each end of the target molecule) can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

In certain embodiments described herein, a population of different forms of nucleic acids (e.g., hypermethylated and hypomethylated DNA in a sample) can be physically partitioned to analysis, e.g., sequencing, or tagging and sequencing. This approach can be used to determine, for example, whether hypermethylation variable epigenetic target regions show hypermethylation characteristic of tumor cells or hypomethylation variable epigenetic target regions show hypomethylation characteristic of tumor cells. Additionally, by partitioning a heterogeneous nucleic acid population, one may increase rare signals, e.g., by enriching rare nucleic acid molecules that are more prevalent in one fraction (or partition) of the population. For example, a genetic variation present in hyper-methylated DNA but less (or not) in hypomethylated DNA can be more easily detected by partitioning a sample into hyper-methylated and hypo-methylated nucleic acid molecules. By analyzing multiple fractions of a sample, a multi-dimensional analysis of a single locus of a genome or species of nucleic acid can be performed and hence, greater sensitivity can be achieved.

In some instances, a heterogeneous nucleic acid sample is partitioned into two or more partitions (e.g., at least 3, 4, 5, 6 or 7 partitions). In some embodiments, each partition is differentially tagged—i.e., each partition can have a different set of molecular barcodes. Tagged partitions can then be pooled together for collective sample prep and/or sequencing. The partitioning-tagging-pooling steps can occur more than once, with each round of partitioning occurring based on a different characteristics (examples provided herein) and tagged using differential tags that are distinguished from other partitions and partitioning means.

Examples of characteristics that can be used for partitioning include sequence length, methylation level, nucleosome binding, sequence mismatch, immunoprecipitation, and/or proteins that bind to DNA. Resulting partitions can include one or more of the following nucleic acid forms: single-stranded DNA (ssDNA), double-stranded DNA (dsDNA), shorter DNA fragments and longer DNA fragments. In some embodiments, a heterogeneous population of nucleic acids is partitioned into nucleic acids with one or more epigenetic modifications and without the one or more epigenetic modifications. Examples of epigenetic modifications include presence or absence of methylation; level of methylation; type of methylation (e.g., 5-methylcytosine versus other types of methylation, such as adenine methylation and/or cytosine hydroxymethylation); and association and level of association with one or more proteins, such as histones. Alternatively, or additionally, a heterogeneous population of nucleic acids can be partitioned into nucleic acid molecules associated with nucleosomes and nucleic acid molecules devoid of nucleosomes. Alternatively, or additionally, a heterogeneous population of nucleic acids may be partitioned into single-stranded DNA (ssDNA) and double-stranded DNA (dsDNA). Alternatively, or additionally, a heterogeneous population of nucleic acids may be partitioned based on nucleic acid length (e.g., molecules of up to 160 bp and molecules having a length of greater than 160 bp).

In some instances, each partition (representative of a different nucleic acid form) is differentially tagged with molecular barcodes, and the partitions are pooled together prior to sequencing. In other instances, the different forms are separately sequenced. In some embodiments, a single tag can be used to label a specific partition. In some embodiments, multiple different tags can be used to label a specific partition. In embodiments employing multiple different tags to label a specific partition, the set of tags used to label one partition can be readily differentiated from the set of tags used to label other partitions. In some embodiments, a tag can be multifunctional—i.e., it can simultaneously act as a molecular identifier (i.e., molecular barcode), partition identifier (i.e., partition tag) and sample identifier (i.e., sample index). For example, if there are four DNA samples and each DNA sample is partitioned into three partitions, then the DNA molecules in each of the twelve partitions (i.e., twelve partitions for the four DNA samples in total) can be tagged with a separate set of tags such that the tag sequence attached to the DNA molecule reveals the identity of the DNA molecule, the partition it belongs to and the sample from which it was originated. In some embodiments, a tag can be used both as a molecular barcode and as a partition tag. For example, if a DNA sample is partitioned into three partitions, then DNA molecule in each partition is tagged with a separated set of tags such that the tag sequence attached to a DNA molecule reveals the identity of the DNA molecule and the partition it belongs to. In some embodiments, a tag can be used both as a molecular barcode and as a sample index. For example, if there are four DNA samples, then DNA molecules in each sample with be tagged with a separate set of tags that can be distinguishable from each sample such that the tag sequence attached to the DNA molecule serves as a molecule identifier and as a sample identifier.

In one embodiment, partition tagging comprises tagging molecules in each partition with a partition tag. After re-combining partitions and sequencing molecules, the partition tags identify the source partition. In another embodiment, different partitions are tagged with different sets of molecular tags, e.g., comprised of a pair of barcodes. In this way, each molecular barcode indicates the source partition as well as being useful to distinguish molecules within a partition. For example, a first set of 35 barcodes can be used to tag molecules in a first partition, while a second set of 35 barcodes can be used tag molecules in a second partition.

In some embodiments, after partitioning and tagging with partition tags, the molecules may be pooled for sequencing in a single run. In some embodiments, a sample tag is added to the molecules, e.g., in a step subsequent to addition of partition tags and pooling. Sample tags can facilitate pooling material generated from multiple samples for sequencing in a single sequencing run.

Alternatively, in some embodiments, partition tags may be correlated to the sample as well as the partition. As a simple example, a first tag can indicate a first partition of a first sample; a second tag can indicate a second partition of the first sample; a third tag can indicate a first partition of a second sample; and a fourth tag can indicate a second partition of the second sample.

While tags may be attached to molecules already partitioned based on one or more epigenetic characteristics, the final tagged molecules in the library may no longer possess that epigenetic characteristic. For example, while single stranded DNA molecules may be partitioned and tagged, the final tagged molecules in the library are likely to be double stranded. Similarly, while DNA may be subject to partition based on different levels of methylation, in the final library, tagged molecules derived from these molecules are likely to be unmethylated. Accordingly, the tag attached to molecule in the library typically indicates the characteristic of the "parent molecule" from which the ultimate tagged molecule is derived, not necessarily to characteristic of the tagged molecule, itself.

As an example, barcodes 1, 2, 3, 4, etc. are used to tag and label molecules in the first partition; barcodes A, B, C, D, etc. are used to tag and label molecules in the second partition; and barcodes a, b, c, d, etc. are used to tag and label molecules in the third partition. Differentially tagged partitions can be pooled prior to sequencing. Differentially tagged partitions can be separately sequenced or sequenced together concurrently, e.g., in the same flow cell of an Illumina sequencer.

After sequencing, analysis of reads to detect genetic variants can be performed on a partition-by-partition level, as well as a whole nucleic acid population level. Tags are used to sort reads from different partitions. Analysis can include in silico analysis to determine genetic and epigenetic variation (one or more of methylation, chromatin structure, etc.) using sequence information, genomic coordinates length, coverage and/or copy number. In some embodiments, higher coverage can correlate with higher nucleosome occupancy in genomic region while lower coverage can correlate with lower nucleosome occupancy or a nucleosome depleted region (NDR).

C. Amplification

Sample nucleic acids may be flanked by adapters and amplified by PCR and other amplification methods using nucleic acid primers binding to primer binding sites in adapters flanking a DNA molecule to be amplified. In some embodiments, amplification methods involve cycles of extension, denaturation, and annealing resulting from thermocycling, or can be isothermal as, for example, in transcription mediated amplification. Other examples of amplification methods that may be optionally utilized include the ligase chain reaction, strand displacement amplification, nucleic acid sequence-based amplification, and self-sustained sequence-based replication.

Typically, the amplification reactions generate a plurality of non-uniquely or uniquely tagged nucleic acid amplicons with molecular barcodes and sample indexes at size ranging from about 150 nucleotides (nt), to about 700 nt, from 250 nt to about 350 nt, or from about 320 nt to about 550 nt. In some embodiments, the amplicons have a size of about 180 nt. In some embodiments, the amplicons have a size of about 200 nt.

D. Enrichment/Capturing

In some embodiments, sequences are enriched prior to sequencing the nucleic acids. Enrichment optionally performed for specific target regions or nonspecifically ("target sequences"). In some embodiments, targeted regions of interest may be enriched/captured with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In some embodiments, a probe set strategy involves tiling the probes across a region of interest. Such probes can be, for example, from about 60 to about 120 nucleotides in length. The set can have a depth (e.g., depth of coverage) of about 2×, 3×, 4×, 5×, 6×, 7×, 8×, 9×, 10×, 15×, 20×, 50×, or more than 50×. The effectiveness of sequence capture generally depends, in part, on the length of the sequence in the target molecule that is complementary (or nearly complementary) to the sequence of the probe.

In some embodiments, the enriched DNA molecules (or the captured set) may comprise DNA corresponding to a sequence-variable target region set and an epigenetic target region set. In some embodiments the quantity of captured sequence-variable target region DNA is greater than the quantity of the captured epigenetic target region DNA, when normalized for the difference in the size of the targeted regions (footprint size). In some embodiments, the compositions, methods and systems described in PCT Patent Application No. PCT/US2020/016120, which is hereby incorporated by reference in its entirety.

Alternatively, first and second captured sets may be provided, comprising, respectively, DNA corresponding to a sequence-variable target region set and DNA corresponding to an epigenetic target region set. The first and second captured sets may be combined to provide a combined captured set.

In a captured set comprising DNA corresponding to the sequence-variable target region set and the epigenetic target region set, including a combined captured set as discussed above, the DNA corresponding to the sequence-variable target region set may be present at a greater concentration than the DNA corresponding to the epigenetic target region set, e.g., a 1.1 to 1.2-fold greater concentration, a 1.2- to 1.4-fold greater concentration, a 1.4- to 1.6-fold greater concentration, a 1.6- to 1.8-fold greater concentration, a 1.8- to 2.0-fold greater concentration, a 2.0- to 2.2-fold greater concentration, a 2.2- to 2.4-fold greater concentration a 2.4- to 2.6-fold greater concentration, a 2.6- to 2.8-fold greater concentration, a 2.8- to 3.0-fold greater concentration, a 3.0- to 3.5-fold greater concentration, a 3.5- to 4.0, a 4.0- to 4.5-fold greater concentration, a 4.5- to 5.0-fold greater concentration, a 5.0- to 5.5-fold greater concentration, a 5.5- to 6.0-fold greater concentration, a 6.0- to 6.5-fold greater concentration, a 6.5- to 7.0-fold greater, a 7.0- to 7.5-fold greater concentration, a 7.5- to 8.0-fold greater concentration, an 8.0- to 8.5-fold greater concentration, an 8.5- to 9.0-fold greater concentration, a 9.0- to 9.5-fold greater concentration, 9.5- to 10.0-fold greater concentration, a 10- to 11-fold greater concentration, an 11- to 12-fold greater concentration a 12- to 13-fold greater concentration, a 13- to 14-fold greater concentration, a 14- to 15-fold greater concentration, a 15- to 16-fold greater concentration, a 16- to 17-fold greater concentration, a 17- to 18-fold greater concentration, an 18- to 19-fold greater concentration, or a 19- to 20-fold greater concentration. The degree of difference in concentrations accounts for normalization for the footprint sizes of the target regions, as discussed in the definition section.

a. Epigenetic Target Region Set

The epigenetic target region set may comprise one or more types of target regions likely to differentiate DNA from neoplastic (e.g., tumor or cancer) cells and from healthy cells, e.g., non-neoplastic circulating cells. Exemplary types of such regions are discussed in detail herein. In some embodiments, methods according to the disclosure comprise determining whether cfDNA molecules corresponding to the epigenetic target region set comprise or indicate cancer-associated epigenetic modifications (e.g., hypermethylation in one or more hypermethylation variable target regions; one or more perturbations of CTCF binding; and/or one or more perturbations of transcription start sites) and/or copy number variations (e.g., focal amplifications). The epigenetic target region set may also comprise one or more control regions, e.g., as described herein.

In some embodiments, the epigenetic target region set has a footprint of at least 100 kb, e.g., at least 200 kb, at least 300 kb, or at least 400 kb. In some embodiments, the epigenetic target region set has a footprint in the range of 100-1000 kb, e.g., 100-200 kb, 200-300 kb, 300-400 kb, 400-500 kb, 500-600 kb, 600-700 kb, 700-800 kb, 800-900 kb, and 900-1,000 kb.

i. Hypermethylation Variable Target Regions

In some embodiments, the epigenetic target region set comprises one or more hypermethylation variable target regions. In general, hypermethylation variable target regions refer to regions where an increase in the level of observed methylation indicates an increased likelihood that a sample (e.g., of cfDNA) contains DNA produced by neoplastic cells, such as tumor or cancer cells. For example, hypermethylation of promoters of tumor suppressor genes has been observed repeatedly. See, e.g., Kang et al., Genome Biol. 18:53 (2017) and references cited therein.

An extensive discussion of methylation variable target regions in colorectal cancer is provided in Lam et al., Biochim Biophys Acta. 1866:106-20 (2016). These include VIM, SEPT9, ITGA4, OSM4, GATA4 and NDRG4. An exemplary set of hypermethylation variable target regions comprising the genes or portions thereof based on the colorectal cancer (CRC) studies is provided in Table 1. Many of these genes likely have relevance to cancers beyond colorectal cancer; for example, TP53 is widely recognized as a critically important tumor suppressor and hypermethylation-based inactivation of this gene may be a common oncogenic mechanism.

TABLE 1

Exemplary hypermethylation target regions (genes or portions thereof) based on CRC studies.

| Gene Name | Additional Gene Name | Chromosome |
| --- | --- | --- |
| VIM | | chr10 |
| SEPT9 | | chr17 |
| CYCD2 | CCND2 | chr12 |
| TFPI2 | | chr7 |
| GATA4 | | chr8 |
| RARB2 | RARB | chr3 |
| p16INK4a | CDKN2A | chr9 |
| MGMT | MGMT | chr10 |
| APC | | chr5 |
| NDRG4 | | chr16 |
| HLTF | | chr3 |
| HPP1 | TMEFF2 | chr2 |
| hMLH1 | MLH1 | chr3 |
| RASSF1A | RASSF1 | chr3 |
| CDH13 | | chr16 |
| IGFBP3 | | chr7 |
| ITGA4 | | chr2 |

In some embodiments, the hypermethylation variable target regions comprise a plurality of genes or portions thereof listed in Table 1, e.g., at least 10%, 20%, 30%, 40%, 50%, 60%, 70%, 80%, 90%, or 100% of the genes or portions thereof listed in Table 1. For example, for each locus included as a target region, there may be one or more probes with a hybridization site that binds between the transcription start site and the stop codon (the last stop codon for genes that are alternatively spliced) of the gene. In some embodiments, the one or more probes bind within 300 bp upstream and/or downstream of the genes or portions thereof listed in Table 1, e.g., within 200 or 100 bp.

Methylation variable target regions in various types of lung cancer are discussed in detail, e.g., in Ooki et al., Clin. Cancer Res. 23:7141-52 (2017); Belinksy, Annu. Rev. Physiol. 77:453-74 (2015); Hulbert et al., Clin. Cancer Res. 23:1998-2005 (2017); Shi et al., BMC Genomics 18:901 (2017); Schneider et al., BMC Cancer. 11:102 (2011); Lissa et al., Transl Lung Cancer Res 5(5):492-504 (2016); Skvortsova et al., Br. J. Cancer. 94(10):1492-1495 (2006); Kim et al., Cancer Res. 61:3419-3424 (2001); Furonaka et al., Pathology International 55:303-309 (2005); Gomes et al., Rev. Port. Pneumol. 20:20-30 (2014); Kim et al., Oncogene. 20:1765-70 (2001); Hopkins-Donaldson et al., Cell Death Differ. 10:356-64 (2003); Kikuchi et al., Clin. Cancer Res. 11:2954-61 (2005); Heller et al., Oncogene 25:959-968 (2006); Licchesi et al., Carcinogenesis. 29:895-904 (2008); Guo et al., Clin. Cancer Res. 10:7917-24 (2004); Palmisano et al., Cancer Res. 63:4620-4625 (2003); and Toyooka et al., Cancer Res. 61:4556-4560, (2001).

An exemplary set of hypermethylation variable target regions comprising genes or portions thereof based on the lung cancer studies is provided in Table 2. Many of these genes likely have relevance to cancers beyond lung cancer; for example, Casp8 (Caspase 8) is a key enzyme in programmed cell death and hypermethylation-based inactivation of this gene may be a common oncogenic mechanism not limited to lung cancer. Additionally, a number of genes appear in both Tables 1 and 2, indicating generality.

TABLE 2

Exemplary hypermethylation target regions (genes or portions thereof) based on lung cancer studies

| Gene Name | Chromosome |
| --- | --- |
| MARCH11 | chr5 |
| TAC1 | chr7 |
| TCF21 | chr6 |
| SHOX2 | chr3 |
| p16 | chr3 |
| Casp8 | chr2 |
| CDH13 | chr16 |
| MGMT | chr10 |
| MLH1 | chr3 |
| MSH2 | chr2 |
| TSLC1 | chr11 |
| APC | chr5 |
| DKK1 | chr10 |
| DKK3 | chr11 |
| LKB1 | chr11 |
| WIF1 | chr12 |
| RUNX3 | chr1 |
| GATA4 | chr8 |
| GATA5 | chr20 |
| PAX5 | chr9 |
| E-Cadherin | chr16 |
| H-Cadherin | chr16 |

Any of the foregoing embodiments concerning target regions identified in Table 2 may be combined with any of the embodiments described above concerning target regions identified in Table 1. In some embodiments, the hypermethylation variable target regions comprise a plurality of genes or portions thereof listed in Table 1 or Table 2, e.g., at least 10%, 20%, 30%, 40%, 50%, 60%, 70%, 80%, 90%, or 100% of the genes or portions thereof listed in Table 1 or Table 2.

Additional hypermethylation target regions may be obtained, e.g., from the Cancer Genome Atlas. Kang et al., Genome Biology 18:53 (2017), describe construction of a probabilistic method called Cancer Locator using hypermethylation target regions from breast, colon, kidney, liver, and lung. In some embodiments, the hypermethylation target regions can be specific to one or more types of cancer. Accordingly, in some embodiments, the hypermethylation target regions include one, two, three, four, or five subsets of hypermethylation target regions that collectively show hypermethylation in one, two, three, four, or five of breast, colon, kidney, liver, and lung cancers.

ii. Hypomethylation Variable Target Regions

Global hypomethylation is a commonly observed phenomenon in various cancers. See, e.g., Hon et al., Genome Res. 22:246-258 (2012) (breast cancer); Ehrlich, Epigenomics 1:239-259 (2009) (review article noting observations of hypomethylation in colon, ovarian, prostate, leukemia, hepatocellular, and cervical cancers). For example, regions such as repeated elements, e.g., LINE1 elements, Alu elements, centromeric tandem repeats, pericentromeric tandem repeats, and satellite DNA, and intergenic regions that are ordinarily methylated in healthy cells may show reduced methylation in tumor cells. Accordingly, in some embodiments, the epigenetic target region set includes hypomethylation variable target regions, where a decrease in the level of observed methylation indicates an increased likelihood that a sample (e.g., of cfDNA) contains DNA produced by neoplastic cells, such as tumor or cancer cells.

In some embodiments, hypomethylation variable target regions include repeated elements and/or intergenic regions. In some embodiments, repeated elements include one, two, three, four, or five of LINE' elements, Alu elements, centromeric tandem repeats, pericentromeric tandem repeats, and/or satellite DNA.

Exemplary specific genomic regions that show cancer-associated hypomethylation include nucleotides 8403565-8953708 and 151104701-151106035 of human chromosome 1, e.g., according to the hg19 or hg38 human genome construct. In some embodiments, the hypomethylation variable target regions overlap or comprise one or both of these regions.

iii. CTCF Binding Regions

CTCF is a DNA-binding protein that contributes to chromatin organization and often colocalizes with cohesin. Perturbation of CTCF binding sites has been reported in a variety of different cancers. See, e.g., Katainen et al., Nature Genetics, doi:10.1038/ng.3335, published online 8 Jun. 2015; Guo et al., Nat. Commun. 9:1520 (2018). CTCF binding results in recognizable patterns in cfDNA that can be detected by sequencing, e.g., through fragment length analysis. For example, details regarding sequencing-based fragment length analysis are provided in Snyder et al., Cell 164:57-68 (2016); WO 2018/009723; and US20170211143A1, each of which are incorporated herein by reference.

Thus, perturbations of CTCF binding result in variation in the fragmentation patterns of cfDNA. As such, CTCF binding sites represent a type of fragmentation variable target regions.

There are many known CTCF binding sites. See, e.g., the CTCFBSDB (CTCF Binding Site Database), available on the Internet at insulatordb.uthsc.edu/; Cuddapah et al., Genome Res. 19:24-32 (2009); Martin et al., Nat. Struct. Mol. Biol. 18:708-14 (2011); Rhee et al., Cell. 147:1408-19 (2011), each of which are incorporated by reference. Exemplary CTCF binding sites are at nucleotides 56014955-56016161 on chromosome 8 and nucleotides 95359169-95360473 on chromosome 13, e.g., according to the hg19 or hg38 human genome construct.

Accordingly, in some embodiments, the epigenetic target region set includes CTCF binding regions. In some embodiments, the CTCF binding regions comprise at least 10, 20, 50, 100, 200, or 500 CTCF binding regions, or 10-20, 20-50, 50-100, 100-200, 200-500, or 500-1000 CTCF binding regions, e.g., such as CTCF binding regions described above or in one or more of CTCFBSDB or the Cuddapah et al., Martin et al., or Rhee et al. articles cited above.

In some embodiments, at least some of the CTCF sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the CTCF binding sites.

iv. Transcription Start Sites

Transcription start sites may also show perturbations in neoplastic cells. For example, nucleosome organization at various transcription start sites in healthy cells of the hematopoietic lineage—which contributes substantially to cfDNA in healthy individuals—may differ from nucleosome organization at those transcription start sites in neoplastic cells. This results in different cfDNA patterns that can be detected by sequencing, for example, as discussed generally in Snyder et al., Cell 164:57-68 (2016); WO 2018/009723; and US20170211143A1.

Thus, perturbations of transcription start sites also result in variation in the fragmentation patterns of cfDNA. As such, transcription start sites also represent a type of fragmentation variable target regions.

Human transcriptional start sites are available from DBTSS (DataBase of Human Transcription Start Sites), available on the Internet at dbtss.hgc.jp and described in Yamashita et al., Nucleic Acids Res. 34 (Database issue): D86-D89 (2006), which is incorporated herein by reference.

Accordingly, in some embodiments, the epigenetic target region set includes transcriptional start sites. In some embodiments, the transcriptional start sites comprise at least 10, 20, 50, 100, 200, or 500 transcriptional start sites, or 10-20, 20-50, 50-100, 100-200, 200-500, or 500-1000 transcriptional start sites, e.g., such as transcriptional start sites listed in DBTSS. In some embodiments, at least some of the transcription start sites can be methylated or unmethylated, wherein the methylation state is correlated with the whether or not the cell is a cancer cell. In some embodiments, the epigenetic target region set comprises at least 100 bp, at least 200 bp, at least 300 bp, at least 400 bp, at least 500 bp, at least 750 bp, at least 1000 bp upstream and/or downstream regions of the transcription start sites.

v. Copy Number Variations; Focal Amplifications

Although copy number variations such as focal amplifications are somatic mutations, they can be detected by sequencing based on read frequency in a manner analogous to approaches for detecting certain epigenetic changes such as changes in methylation. As such, regions that may show copy number variations such as focal amplifications in cancer can be included in the epigenetic target region set and may comprise one or more of AR, BRAF, CCND1, CCND2, CCNE1, CDK4, CDK6, EGFR, ERBB2, FGFR1, FGFR2, KIT, KRAS, MET, MYC, PDGFRA, PIK3CA, and RAF1. For example, in some embodiments, the epigenetic target region set comprises at least 2, 3, 4, 5, 6, 7, 8, 9, 10, 11, 12, 13, 14, 15, 16, 17, or 18 of the foregoing targets.

iv. Methylation Control Regions

It can be useful to include control regions to facilitate data validation. In some embodiments, the epigenetic target region set includes control regions that are expected to be methylated or unmethylated in essentially all samples, regardless of whether the DNA is derived from a cancer cell or a normal cell. In some embodiments, the epigenetic target region set includes control hypomethylated regions that are expected to be hypomethylated in essentially all samples. In some embodiments, the epigenetic target region set includes control hypermethylated regions that are expected to be hypermethylated in essentially all samples.

b. Sequence-Variable Target Region Set

In some embodiments, the sequence-variable target region set comprises a plurality of regions known to undergo somatic mutations in cancer (referred to herein as cancer-associated mutations). Accordingly, methods may comprise determining whether cfDNA molecules corresponding to the sequence-variable target region set comprise cancer-associated mutations.

In some embodiments, the sequence-variable target region set targets a plurality of different genes or genomic regions ("panel") selected such that a determined proportion of subjects having a cancer exhibits a genetic variant or tumor marker in one or more different genes or genomic regions in the panel. The panel may be selected to limit a region for sequencing to a fixed number of base pairs. The panel may be selected to sequence a desired amount of DNA, e.g., by adjusting the affinity and/or amount of the probes as described elsewhere herein. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models.

Examples of listings of genomic locations of interest may be found in Table 3 and Table 4. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, or 70 of the genes of Table 3. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, or 70 of the SNVs of Table 3. In some embodiments, a sequence-variable target region set used in the methods of the present disclosure comprises at least 1, at least 2, at least 3, at least 4, at least 5, or 6 of the fusions of Table 3. In some embodiments, a sequence-variable target region set used in the methods of the present disclosure comprise at least a portion of at least 1, at least 2, or 3 of the indels of Table 3. In some embodiments, a sequence-variable target region set used in the methods of the present disclosure comprises at least a portion of at least 5, at least 10, at least 15, at least 20, at least 25, at least 30, at least 35, at least 40, at least 45, at least 50, at least 55, at least 60, at least 65, at least 70, or 73 of the genes of Table 4. In some embodiments, a sequence-variable target region set used in the methods of the present disclosure comprises at least 5, at least 10, at least 15, at least 20, at least 25, at least 30, at least 35, at least 40, at least 45, at least 50, at least 55, at least 60, at least 65, at least 70, or 73 of the SNVs of Table 4. In some embodiments, a sequence-variable target region set used in the methods of the present disclosure comprises at least 1, at least 2, at least 3, at least 4, at least 5, or 6 of the fusions of Table 4. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 4. Each of these genomic locations of interest may be identified as a backbone region or hot-spot region for a given panel. An example of a listing of hot-spot genomic locations of interest may be found in Table 5. The coordinates in Table 5 are based on the hg19 assembly of the human genome, but one skilled in the art will be familiar with other assemblies and can identify coordinate sets corresponding to the indicated exons, introns, codons, etc. in an assembly of their choice. In some embodiments, a sequence-variable target region set used in the methods of the present disclosure comprises at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 5. Each hot-spot genomic region is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic region of interest may seek to capture.

TABLE 3

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | CDKN2B | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |

TABLE 3-continued

| Point Mutations (SNVs) and Indels | | | | | Fusions |
|---|---|---|---|---|---|
| RIT1 | ROS1 | SMAD4 | SMO | SRC | STK11 |
| TERT | TP53 | TSC1 | VHL | | |

TABLE 4

| Point Mutations (SNVs) and Indels | | | | | | Fusions |
|---|---|---|---|---|---|---|
| AKT1 | ALK | APC | AR | ARAF | ARID1A | ALK |
| ATM | BRAF | BRCA1 | BRCA2 | CCND1 | CCND2 | FGFR2 |
| CCNE1 | CDH1 | CDK4 | CDK6 | CDKN2A | DDR2 | FGFR3 |
| CTNNB1 | EGFR | ERBB2 | ESR1 | EZH2 | FBXW7 | NTRK1 |
| FGFR1 | FGFR2 | FGFR3 | GATA3 | GNA11 | GNAQ | RET |
| GNAS | HNF1A | HRAS | IDH1 | IDH2 | JAK2 | ROS1 |
| JAK3 | KIT | KRAS | MAP2K1 | MAP2K2 | MET | |
| MLH1 | MPL | MYC | NF1 | NFE2L2 | NOTCH1 | |
| NPM1 | NRAS | NTRK1 | PDGFRA | PIK3CA | PTEN | |
| PTPN11 | RAF1 | RB1 | RET | RHEB | RHOA | |
| RIT1 | ROS1 | SMAD4 | SMO | MAPK1 | STK11 | |
| TERT | TP53 | TSC1 | VHL | MAPK3 | MTOR | |
| NTRK3 | | | | | | |

TABLE 5

| Gene | Chromosome | Start Position | Stop Position | Length (bp) | Exons/Introns Covered | Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | exon 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | exon 19 | Fusion |
| ALK | chr2 | 29449366 | 29449777 | 411 | intron 18 | Fusion |
| ALK | chr2 | 29449778 | 29449950 | 172 | exon 18 | Fusion |
| BRAF | chr7 | 140453064 | 140453203 | 139 | exon 15 | BRAF V600 |
| CTNNB1 | chr3 | 41266007 | 41266254 | 247 | exon 3 | S37 |
| EGFR | chr7 | 55240528 | 55240827 | 299 | exons 18 and 19 | G719 and deletions |
| EGFR | chr7 | 55241603 | 55241746 | 143 | exon 20 | Insertions/T790M |
| EGFR | chr7 | 55242404 | 55242523 | 119 | exon 21 | L858R |
| ERBB2 | chr17 | 37880952 | 37881174 | 222 | exon 20 | Insertions |
| ESR1 | chr6 | 152419857 | 152420111 | 254 | exon 10 | V534, P535, L536, Y537, D538 |
| FGFR2 | chr10 | 123279482 | 123279693 | 211 | exon 6 | S252 |
| GATA3 | chr10 | 8111426 | 8111571 | 145 | exon 5 | SS/Indels |
| GATA3 | chr10 | 8115692 | 8116002 | 310 | exon 6 | SS/Indels |
| GNAS | chr20 | 57484395 | 57484488 | 93 | exon 8 | R844 |
| IDH1 | chr2 | 209113083 | 209113394 | 311 | exon 4 | R132 |
| IDH2 | chr15 | 90631809 | 90631989 | 180 | exon 4 | R140, R172 |
| KIT | chr4 | 55524171 | 55524258 | 87 | exon 1 | |
| KIT | chr4 | 55561667 | 55561957 | 290 | exon 2 | |
| KIT | chr4 | 55564439 | 55564741 | 302 | exon 3 | |
| KIT | chr4 | 55565785 | 55565942 | 157 | exon 4 | |
| KIT | chr4 | 55569879 | 55570068 | 189 | exon 5 | |
| KIT | chr4 | 55573253 | 55573463 | 210 | exon 6 | |
| KIT | chr4 | 55575579 | 55575719 | 140 | exon 7 | |
| KIT | chr4 | 55589739 | 55589874 | 135 | exon 8 | |
| KIT | chr4 | 55592012 | 55592226 | 214 | exon 9 | |
| KIT | chr4 | 55593373 | 55593718 | 345 | exons 10 and 11 | 557, 559, 560, 576 |
| KIT | chr4 | 55593978 | 55594297 | 319 | exons 12 and 13 | V654 |
| KIT | chr4 | 55595490 | 55595661 | 171 | exon 14 | T670, S709 |
| KIT | chr4 | 55597483 | 55597595 | 112 | exon 15 | D716 |
| KIT | chr4 | 55598026 | 55598174 | 148 | exon 16 | L783 |
| KIT | chr4 | 55599225 | 55599368 | 143 | exon 17 | C809, R815, D816, L818, D820, S821F, N822, Y823 |
| KIT | chr4 | 55602653 | 55602785 | 132 | exon 18 | A829P |
| KIT | chr4 | 55602876 | 55602996 | 120 | exon 19 | |

TABLE 5-continued

| Gene | Chromosome | Start Position | Stop Position | Length (bp) | Exons/Introns Covered | Feature |
|---|---|---|---|---|---|---|
| KIT | chr4 | 55603330 | 55603456 | 126 | exon 20 | |
| KIT | chr4 | 55604584 | 55604733 | 149 | exon 21 | |
| KRAS | chr12 | 25378537 | 25378717 | 180 | exon 4 | A146 |
| KRAS | chr12 | 25380157 | 25380356 | 199 | exon 3 | Q61 |
| KRAS | chr12 | 25398197 | 25398328 | 131 | exon 2 | G12/G13 |
| MET | chr7 | 116411535 | 116412255 | 720 | exon 13, exon 14, intron 13, intron 14 | MET exon 14 SS |
| NRAS | chr1 | 115256410 | 115256609 | 199 | exon 3 | Q61 |
| NRAS | chr1 | 115258660 | 115258791 | 131 | exon 2 | G12/G13 |
| PIK3CA | chr3 | 178935987 | 178936132 | 145 | exon 10 | E545K |
| PIK3CA | chr3 | 178951871 | 178952162 | 291 | exon 21 | H1047R |
| PTEN | chr10 | 89692759 | 89693018 | 259 | exon 5 | R130 |
| SMAD4 | chr18 | 48604616 | 48604849 | 233 | exon 12 | D537 |
| TERT | chr5 | 1294841 | 1295512 | 671 | promoter | chr5:1295228 |
| TP53 | chr17 | 7573916 | 7574043 | 127 | exon 11 | Q331, R337, R342 |
| TP53 | chr17 | 7577008 | 7577165 | 157 | exon 8 | R273 |
| TP53 | chr17 | 7577488 | 7577618 | 130 | exon 7 | R248 |
| TP53 | chr17 | 7578127 | 7578299 | 172 | exon 6 | R213/Y220 |
| TP53 | chr17 | 7578360 | 7578564 | 204 | exon 5 | R175/Deletions |
| TP53 | chr17 | 7579301 | 7579600 | 299 | exon 4 | |
| | | | | 12574 (total target region) | | |
| | | | | 16330 (total probe coverage) | | |

Additionally, or alternatively, suitable target region sets are available from the literature. For example, Gale et al., PLoS One 13: e0194630 (2018), which is incorporated herein by reference, describes a panel of 35 cancer-related gene targets that can be used as part or all of a sequence-variable target region set. These 35 targets are AKT1, ALK, BRAF, CCND1, CDK2A, CTNNB1, EGFR, ERBB2, ESR1, FGFR1, FGFR2, FGFR3, FOXL2, GATA3, GNA11, GNAQ, GNAS, HRAS, IDH1, IDH2, KIT, KRAS, MED12, MET, MYC, NFE2L2, NRAS, PDGFRA, PIK3CA, PPP2R1A, PTEN, RET, STK11, TP53, and U2AF1.

In some embodiments, the sequence-variable target region set comprises target regions from at least 10, 20, 30, or 35 cancer-related genes, such as the cancer-related genes listed above.

E. Sequencing

Sample nucleic acids, optionally flanked by adapters, with or without prior amplification are generally subjected to sequencing. Sequencing methods or commercially available formats that are optionally utilized include, for example, Sanger sequencing, high-throughput sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next-generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one or more nucleic acid fragment types or regions containing markers of cancer or of other diseases. The sequencing reactions can also be performed on any nucleic acid fragment present in the sample. The sequence reactions may be performed on at least about 5%, 10%, 15%, 20%, 25%, 30%, 40%, 50%, 60%, 70%, 80%, 90%, 95%, 99%, 99.9%, or 100% of the genome. In other cases, sequence reactions may be performed on less than about 5%, 10%, 15%, 20%, 25%, 30%, 40%, 50%, 60%, 70%, 80%, 90%, 95%, 99%, 99.9%, or 100% of the genome.

Simultaneous sequencing reactions may be performed using multiplex sequencing techniques. In some embodiments, cell-free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An example of a read depth is from about 1000 to about 50000 reads per locus (e.g., base position). Another example of a read depth has at least 50000 reads per locus (e.g., base position).

a. Differential Depth of Sequencing

In some embodiments, nucleic acids corresponding to the sequence-variable target region set are sequenced to a greater depth of sequencing than nucleic acids corresponding to the epigenetic target region set. For example, the depth of sequencing for nucleic acids corresponding to the sequence variant target region set may be at least 1.25-, 1.5-, 1.75-, 2-, 2.25-, 2.5-, 2.75-, 3-, 3.5-, 4-, 4.5-, 5-, 6-, 7-, 8-, 9-, 10-, 11-, 12-, 13-, 14-, or 15-fold greater, or 1.25- to 1.5-, 1.5- to 1.75-, 1.75- to 2-, 2- to 2.25-, 2.25- to 2.5-, 2.5- to 2.75-, 2.75- to 3-, 3- to 3.5-, 3.5- to 4-, 4- to 4.5-, 4.5- to 5-, 5- to 5.5-, 5.5- to 6-, 6- to 7-, 7- to 8-, 8- to 9-, 9- to 10-, 10- to 11-, 11- to 12-, 13- to 14-, 14- to 15-fold, or 15- to 100-fold greater, than the depth of sequencing for nucleic acids corresponding to the epigenetic target region set. In some embodiments, said depth of sequencing is at least 2-fold greater. In some embodiments, said depth of sequencing is at least 5-fold greater. In some embodiments, said depth of sequencing is at least 10-fold greater. In some embodiments, said depth of sequencing is 4- to 10-fold greater. In some embodiments, said depth of sequencing is 4- to 100-fold greater. Each of these embodiments refer to the extent to which nucleic acids corresponding to the sequence-variable target region set are sequenced to a greater depth of sequencing than nucleic acids corresponding to the epigenetic target region set.

In some embodiments, the captured DNA corresponding to the sequence-variable target region set and the captured DNA corresponding to the epigenetic target region set are sequenced concurrently, e.g., in the same sequencing cell (such as the flow cell of an Illumina sequencer) and/or in the same composition, which may be a pooled composition resulting from recombining separately captured sets or a composition obtained by capturing the cfDNA corresponding to the sequence-variable target region set and the captured DNA corresponding to the epigenetic target region set in the same vessel.

F. Analysis

Sequencing may generate a plurality of sequence reads or reads. Sequence reads or reads may include sequences of nucleotide data less than about 150 bases in length, or less than about 90 bases in length. In some embodiments, reads are between about 80 bases and about 90 bases, e.g., about 85 bases in length. In some embodiments, methods of the present disclosure are applied to very short reads, e.g., less than about 50 bases or about 30 bases in length. Sequence read data can include the sequence data as well as meta information. Sequence read data can be stored in any suitable file format including, for example, VCF files, FASTA files, or FASTQ files.

FASTA may refer to a computer program for searching sequence databases, and the name FASTA may also refer to a standard file format. FASTA is described by, for example, Pearson & Lipman, 1988, Improved tools for biological sequence comparison, PNAS 85:2444-2448, which is hereby incorporated by reference in its entirety. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There may be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer, as described by, for example, Cock et al. ("The Sanger FASTQ file format for sequences with quality scores, and the Solexa/Illumina FASTQ variants," Nucleic Acids Res 38(6):1767-1771, 2009), which is hereby incorporated by reference in its entirety.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In an embodiment, the sequence data may use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the present disclosure may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Examples of text editors include, without limitation, Microsoft Word, emacs, pico, vi, BBEdit, and TextWrangler. The text editor program may be capable of displaying the plain text files on a computer screen, showing the meta information and the sequence reads in a human-readable format (e.g., not binary encoded but instead using alphanumeric characters as they may be used in print or human writing).

While methods have been discussed with reference to FASTA or FASTQ files, methods and systems of the present disclosure may be used to compress any suitable sequence file format including, for example, files in the Variant Call Format (VCF) format. A typical VCF file may include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described by, for example, Danecek et al. ("The variant call format and VCF tools," Bioinformatics 27(15):2156-2158, 2011), which is hereby incorporated by reference in its entirety. The header section may be treated as the meta information to write to the compressed files and the data section may be treated as the lines, each of which can be stored in a master file only if unique.

Some embodiments provide for the assembly of sequence reads. In assembly by alignment, for example, the sequence reads are aligned to each other or aligned to a reference sequence. By aligning each read, in turn to a reference genome, all of the reads are positioned in relationship to each other to create the assembly. In addition, aligning or mapping the sequence read to a reference sequence can also be used to identify variant sequences within the sequence read. Identifying variant sequences can be used in combination with the methods and systems described herein to further aid in the diagnosis or prognosis of a disease or condition, or for guiding treatment decisions.

In some embodiments, any or all of the steps are automated. Alternatively, methods of the present disclosure may be embodied wholly or partially in one or more dedicated programs, for example, each optionally written in a compiled language such as C++, then compiled and distributed as a binary. Methods of the present disclosure may be implemented wholly or in part as modules within, or by invoking functionality within, existing sequence analysis platforms. In some embodiments, methods of the present disclosure include a number of steps that are all invoked automatically responsive to a single starting queue (e.g., one or a combination of triggering events sourced from human activity, another computer program, or a machine). Thus, the present disclosure provides methods in which any or the steps or any combination of the steps can occur automatically responsive to a queue. "Automatically" generally means without intervening human input, influence, or interaction (e.g., responsive only to original or pre-queue human activity).

The methods of the present disclosure may also encompass various forms of output, which includes an accurate and sensitive interpretation of a subject's nucleic acid sample. The output of retrieval can be provided in the format of a computer file. In some embodiments, the output is a FASTA file, a FASTQ file, or a VCF file. The output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings may include Simple UnGapped Alignment Report (SUGAR), Verbose Useful Labeled Gapped Alignment Report (VULGAR), and Compact Idiosyncratic Gapped Alignment Report (CIGAR) (as described by, for example, Ning et al., Genome Research 11(10):1725-9, 2001, which is hereby incorporated by reference in its entirety). These strings may be implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file-comprising a CIGAR string (the SAM format is described, e.g., by Li et al., "The Sequence Alignment/Map format and SAMtools," Bioinformatics, 25(16):2078-9, 2009, which is hereby incorporated by reference in its entirety). In some embodiments, CIGAR displays or includes gapped alignments one-per-line. CIGAR is a compressed pairwise alignment format reported as a CIGAR string. A CIGAR string may be useful for representing long (e.g., genomic) pairwise alignments. A CIGAR string may be used in SAM format to represent alignments of reads to a reference genome sequence.

A CIGAR string may follow an established motif. Each character is preceded by a number, giving the base counts of the event. Characters used can include M, I, D, N, and S (M=match; I=insertion; D=deletion; N=gap; S=substitution). The CIGAR string defines the sequence of matches and/or mismatches and deletions (or gaps). For example, the CIGAR string 2MD3M2D2M may indicate that the alignment contains 2 matches, 1 deletion (number 1 is omitted in order to save some space), 3 matches, 2 deletions, and 2 matches.

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G, and T or U).

Examples of enzymes or catalytic fragments thereof that may be optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt ends on double-stranded nucleic acids facilitates, for example, the attachment of adapters and subsequent amplification.

In some embodiments, nucleic acid populations are subjected to additional processing, such as the conversion of single-stranded nucleic acids to double-stranded nucleic acids and/or conversion of RNA to DNA (e.g., complementary DNA or cDNA). These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (e.g., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including barcodes, and the sequencing determines nucleic acid sequences as well as in-line barcodes introduced by the adapters. The blunt-end DNA molecules are optionally ligated to a blunt end of an at least partially double-stranded adapter (e.g., a Y-shaped or bell-shaped adapter). Alternatively, blunt ends of sample nucleic acids and adapters can be tailed with complementary nucleotides to facilitate ligation (for e.g., sticky-end ligation).

The nucleic acid sample is typically contacted with a sufficient number of adapters that there is a low probability (e.g., less than about 1% or 0.1%) that any two copies of the same nucleic acid receive the same combination of adapter barcodes from the adapters linked at both ends. The use of adapters in this manner may permit identification of families of nucleic acid sequences with the same start and stop points on a reference nucleic acid and linked to the same combination of barcodes. Such a family may represent sequences of amplification products of a nucleic acid in the sample before amplification. The sequences of family members can be compiled to derive consensus nucleotide(s) or a complete consensus sequence for a nucleic acid molecule in the original sample, as modified by blunt-end formation and adapter attachment. In other words, the nucleotide occupying a specified position of a nucleic acid in the sample can be determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand may be converted to their complements for purposes of compiling sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations (e.g SNVs or indels) in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be an external reference sequence, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (e.g., same as in the reference sequence). If the number of sequenced nucleic acids in the subset including a nucleotide variant exceeding a selected threshold, then a variant nucleotide can be called at the designated position. The threshold can be a number, such as at least 1, 2, 3, 4, 5, 6, 7, 8, 9, or 10 sequenced nucleic acids within the subset including the nucleotide variant, or it can be a ratio, such as at least about 0.5, 1, 2, 3, 4, 5, 10, 15, or 20, of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein, are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, each of which is hereby incorporated by reference in its entirety.

III. Computer Systems

Methods of the present disclosure can be implemented using, or with the aid of, computer systems. For example, such methods, which may comprise (a) directing the obtaining of at least one sample from the subject from at least two different time points to provide at least two samples, wherein a first sample of the at least two samples is obtained at a first time point of the at least two different time points and a second sample of the at least two samples is obtained at a second time point of the at least two different time points; (b) directing the processing of polynucleotides from each of the at least two samples, wherein the processing comprises: (i) partitioning at least a portion of the polynucleotides into at least two partitions based on at least one epigenetic feature, thereby generating partitioned polynucleotides; (ii) tagging at least a portion of the partitioned polynucleotides, thereby generating tagged parent polynucleotides; (iii) amplifying at least a portion of the tagged parent polynucleotides to generate progeny polynucleotides; and (iv) sequencing at least a portion of the progeny polynucleotides to generate a set of sequencing reads; and (c) analyzing a plurality of genomic regions for at least one epigenetic feature from the set of sequencing reads of the at least two samples, to detect the presence or absence of the cancer in the subject at the second time point.

Figure 7:
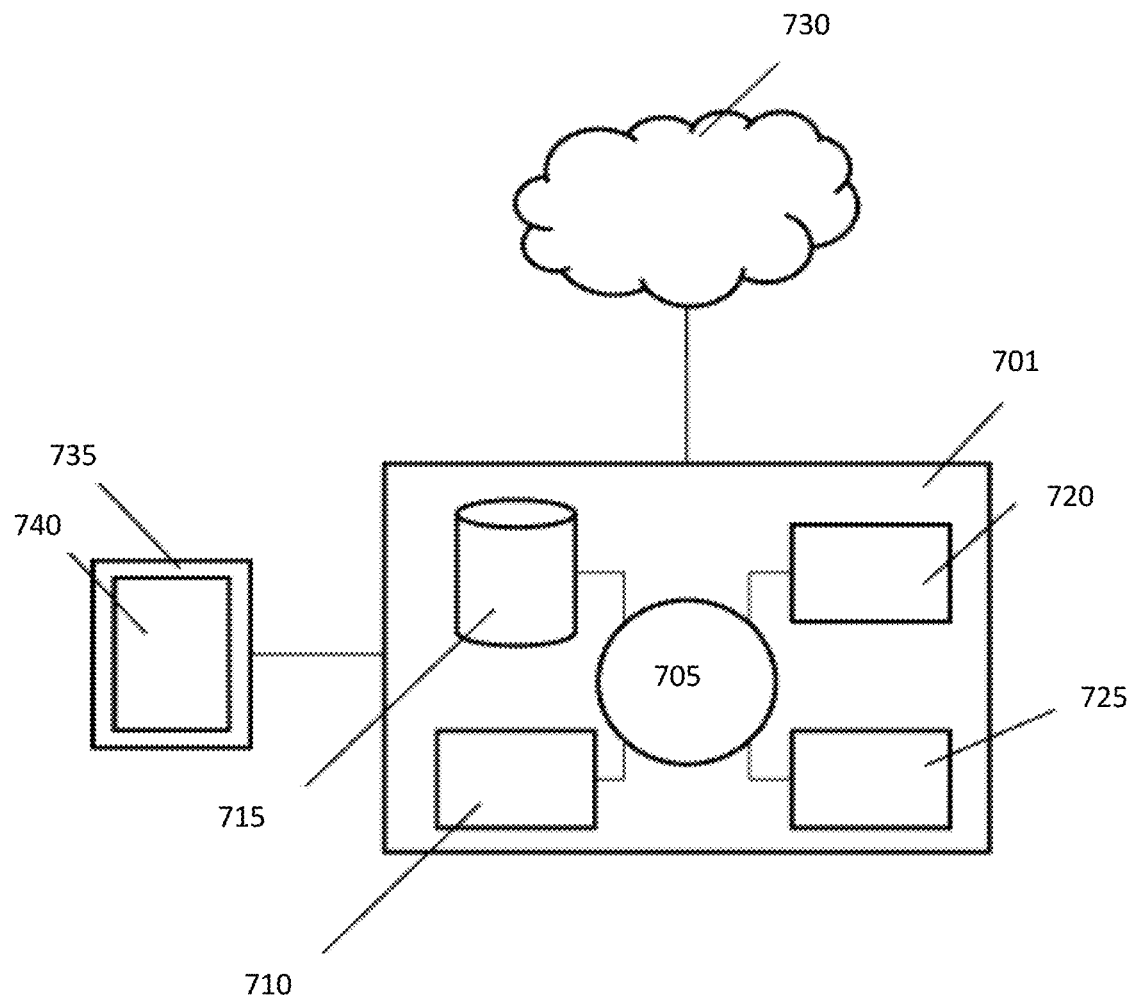
FIG. 7 is a schematic diagram of an example of a system suitable for use with some embodiments of the disclosure.

FIG. 7 shows a computer system 701 that is programmed or otherwise configured to implement the methods of the present disclosure. The computer system 701 can regulate various aspects sample preparation, sequencing, and/or analysis. In some examples, the computer system 701 is configured to perform sample preparation and sample analysis, including nucleic acid sequencing.

The computer system 701 includes a central processing unit (CPU, also "processor" and "computer processor" herein) 705, which can be a single core or multi core processor, or a plurality of processors for parallel processing. The computer system 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage, and/or electronic display adapters. The memory 710, storage unit 715, interface 720, and peripheral devices 725 are in communication with the CPU 705 through a communication network or bus (solid lines), such as a motherboard. The storage unit 715 can be a data storage unit (or data repository) for storing data. The computer system 701 can be operatively coupled to a computer network 730 with the aid of the communication interface 720. The computer network 730 can be the Internet, an internet and/or extranet, or an intranet and/or extranet that is in communication with the Internet. The computer network 730 in some cases is a telecommunication and/or data network. The computer network 730 can include one or more computer servers, which can enable distributed computing, such as cloud computing. The computer network 730, in some cases with the aid of the computer system 701, can implement a peer-to-peer network, which may enable devices coupled to the computer system 701 to behave as a client or a server.

The CPU 705 can execute a sequence of machine-readable instructions, which can be embodied in a program or software. The instructions may be stored in a memory location, such as the memory 710. Examples of operations performed by the CPU 405 can include fetch, decode, execute, and writeback.

The storage unit 715 can store files, such as drivers, libraries, and saved programs. The storage unit 715 can store programs generated by users and recorded sessions, as well as output(s) associated with the programs. The storage unit 715 can store user data, e.g., user preferences and user programs. The computer system 701 in some cases can include one or more additional data storage units that are external to the computer system 701, such as located on a remote server that is in communication with the computer system 701 through an intranet or the Internet. Data may be transferred from one location to another using, for example, a communication network or physical data transfer (e.g., using a hard drive, thumb drive, or other data storage mechanism).

The computer system 701 can communicate with one or more remote computer systems through the network 730. For embodiment, the computer system 701 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 701 via the network 730.

Methods as described herein can be implemented by way of machine (e.g., computer processor) executable code stored on an electronic storage location of the computer system 701, such as, for example, on the memory 710 or electronic storage unit 715. The machine executable or machine-readable code can be provided in the form of software. During use, the code can be executed by the processor 705. In some cases, the code can be retrieved from the storage unit 715 and stored on the memory 710 for ready access by the processor 705. In some situations, the electronic storage unit 715 can be precluded, and machine-executable instructions are stored on memory 710.

In an aspect, the present disclosure provides a non-transitory computer-readable medium comprising computer-executable instructions which, when executed by at least one electronic processor, perform at least a portion of a method comprising: (a) directing the obtaining of at least one sample from the subject from at least two different time points to provide at least two samples, wherein a first sample of the at least two samples is obtained at a first time point of the at least two different time points and a second sample of the at least two samples is obtained at a second time point of the at least two different time points; (b) directing the processing of polynucleotides from each of the at least two samples, wherein the processing comprises: (i) partitioning at least a portion of the polynucleotides into at least two partitions based on at least one epigenetic feature, thereby generating partitioned polynucleotides; (ii) tagging at least a portion of the partitioned polynucleotides, thereby generating tagged parent polynucleotides; (iii) amplifying at least a portion of the tagged parent polynucleotides to generate progeny polynucleotides; and (iv) sequencing at least a portion of the progeny polynucleotides to generate a set of sequencing reads; and (c) analyzing a plurality of genomic regions for at least one epigenetic feature from the set of sequencing reads of the at least two samples, to detect the presence or absence of the cancer in the subject at the second time point.

The code can be pre-compiled and configured for use with a machine have a processer adapted to execute the code or can be compiled during runtime. The code can be supplied in a programming language that can be selected to enable the code to execute in a pre-compiled or as-compiled fashion.

Aspects of the systems and methods provided herein, such as the computer system 701, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semi-conductor memories, tape drives, disk drives and the like, which may provide non-transitory storage at any time for the software programming.

All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as those used across physical interfaces between local devices, through wired and optical landline networks, and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 701 can include or be in communication with an electronic display 735 that comprises a user interface (UI) 740 for providing, for example, one or more results of sample analysis. Examples of UIs include, without limitation, a graphical user interface (GUI) and web-based user interface.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, 7$^{th}$ Ed. (2016), Elmasri, *Fundamentals of Database Systems*, Addison Wesley, 6th Ed. (2010), Coronel, *Database Systems: Design, Implementation, & Management*, Cengage Learning, 11$^{th}$ Ed. (2014), Tucker, *Programming Languages*, McGraw-Hill Science/Engineering/Math, 2nd Ed. (2006), and Rhoton, *Cloud Computing Architected:*

*Solution Design Handbook*, Recursive Press (2011), each of which is hereby incorporated by reference in its entirety.

IV. Applications

A. Cancer and Other Diseases

The present methods can be used to diagnose presence or absence of conditions, particularly cancer, in a subject, to characterize conditions (e.g., staging cancer or determining heterogeneity of a cancer), monitor response to treatment of a condition, effect prognosis risk of developing a condition or subsequent course of a condition. The present disclosure can also be useful in determining the efficacy of a particular treatment option. Successful treatment options may increase the amount of copy number variation or rare mutations detected in subject's blood if the treatment is successful as more cancers may die and shed DNA. In other examples, this may not occur. In another example, perhaps certain treatment options may be correlated with genetic profiles of cancers over time. This correlation may be useful in selecting a therapy.

Additionally, if a cancer is observed to be in remission after treatment, the present methods can be used to monitor residual disease or recurrence of disease.

In some embodiments, the methods and systems disclosed herein may be used to identify customized or targeted therapies to treat a given disease or condition in patients based on the classification of a nucleic acid variant as being of somatic or germline origin. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma. Type and/or stage of cancer can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns, and abnormal changes in nucleic acid 5-methylcytosine.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers can progress to become more aggressive and genetically unstable. Other cancers may remain benign, inactive or dormant. The system and methods of this disclosure may be useful in determining disease progression.

Further, the methods of the disclosure may be used to characterize the heterogeneity of an abnormal condition in a subject. Such methods can include, e.g., generating a genetic profile of extracellular polynucleotides derived from the subject, wherein the genetic profile comprises a plurality of data resulting from copy number variation and rare mutation analyses. In some embodiments, an abnormal condition is cancer. In some embodiments, the abnormal condition may be one resulting in a heterogeneous genomic population. In the example of cancer, some tumors are known to comprise tumor cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation, epigenetic variation, and mutation analyses alone or in combination.

The present methods can be used to diagnose, prognose, monitor or observe cancers, or other diseases. In some embodiments, the methods herein do not involve the diagnosing, prognosing or monitoring a fetus and as such are not directed to non-invasive prenatal testing. In other embodiments, these methodologies may be employed in a pregnant subject to diagnose, prognose, monitor or observe cancers or other diseases in an unborn subject whose DNA and other polynucleotides may co-circulate with maternal molecules.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial Mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay- Sachs, thalassemia, trimethylaminuria, Turner syndrome, velocardiofacial syndrome, WAGR syndrome, Wilson disease, or the like.

In some embodiments, a method described herein comprises detecting a presence or absence of DNA originating or derived from a tumor cell at a preselected timepoint following a previous cancer treatment of a subject previously diagnosed with cancer using a set of sequence information obtained as described herein.

The methods discussed above may further comprise any compatible feature or features set forth elsewhere herein, including in the section regarding methods of determining a risk of cancer recurrence in a test subject and/or classifying a test subject as being a candidate for a subsequent cancer treatment.

B. Methods of Determining a Risk of Cancer Recurrence in a Test Subject and/or Classifying a Test Subject as being a Candidate for a Subsequent Cancer Treatment In some embodiments, a method provided herein is a method of determining a risk of cancer recurrence in a test subject. In some embodiments, a method provided herein is a method of classifying a test subject as being a candidate for a subsequent cancer treatment.

Any of such methods may comprise collecting DNA (e.g., originating or derived from a tumor cell) from the test subject diagnosed with the cancer at one or more preselected timepoints following one or more previous cancer treatments to the test subject. The subject may be any of the subjects described herein. The DNA may be cfDNA. The DNA may be obtained from a tissue sample.

Any of such methods may comprise capturing a plurality of sets of target regions from DNA from the subject, wherein the plurality of target region sets comprises a sequence-variable target region set and an epigenetic target region set, whereby a captured set of DNA molecules is produced. The capturing step may be performed according to any of the embodiments described elsewhere herein.

In any of such methods, the previous cancer treatment may comprise surgery, administration of a therapeutic composition, and/or chemotherapy.

Any of such methods may comprise sequencing the captured DNA molecules, whereby a set of sequence information is produced. The captured DNA molecules of the sequence-variable target region set may be sequenced to a greater depth of sequencing than the captured DNA molecules of the epigenetic target region set.

Any of such methods may comprise detecting a presence or absence of DNA originating or derived from a tumor cell at a preselected timepoint using the set of sequence information. The detection of the presence or absence of DNA originating or derived from a tumor cell may be performed according to any of the embodiments thereof described elsewhere herein.

Methods of determining a risk of cancer recurrence in a test subject may comprise determining a cancer recurrence score that is indicative of the presence or absence, or amount, of the DNA originating or derived from the tumor cell for the test subject. The cancer recurrence score may further be used to determine a cancer recurrence status. The cancer recurrence status may be at risk for cancer recurrence, e.g., when the cancer recurrence score is above a predetermined threshold. The cancer recurrence status may be at low or lower risk for cancer recurrence, e.g., when the cancer recurrence score is above a predetermined threshold. In particular embodiments, a cancer recurrence score equal to the predetermined threshold may result in a cancer recurrence status of either at risk for cancer recurrence or at low or lower risk for cancer recurrence.

Methods of classifying a test subject as being a candidate for a subsequent cancer treatment may comprise comparing the cancer recurrence score of the test subject with a predetermined cancer recurrence threshold, thereby classifying the test subject as a candidate for the subsequent cancer treatment when the cancer recurrence score is above the cancer recurrence threshold or not a candidate for therapy when the cancer recurrence score is below the cancer recurrence threshold. In particular embodiments, a cancer recurrence score equal to the cancer recurrence threshold may result in classification as either a candidate for a subsequent cancer treatment or not a candidate for therapy. In some embodiments, the subsequent cancer treatment comprises chemotherapy or administration of a therapeutic composition.

Any of such methods may comprise determining a disease-free survival (DFS) period for the test subject based on the cancer recurrence score; for example, the DFS period may be 1 year, 2 years, 3, years, 4 years, 5 years, or 10 years.

In some embodiments, the set of sequence information comprises sequence-variable target region sequences, and determining the cancer recurrence score may comprise determining at least a first subscore indicative of the amount of SNVs, insertions/deletions, CNVs and/or fusions present in sequence-variable target region sequences.

In some embodiments, a number of mutations in the sequence-variable target regions chosen from 1, 2, 3, 4, or 5 is sufficient for the first subscore to result in a cancer recurrence score classified as positive for cancer recurrence. In some embodiments, the number of mutations is chosen from 1, 2, or 3.

In some embodiments, the set of sequence information comprises epigenetic target region sequences, and determining the cancer recurrence score comprises determining a second subscore indicative of the changes in the epigenetic features in the epigenetic target region sequences e.g., methylation of hypermethylation variable target regions and/or perturbed fragmentation of fragmentation variable target regions, where "perturbed" means different from DNA found in a corresponding sample from a healthy subject.

In any embodiment where a cancer recurrence score is classified as positive for cancer recurrence, the cancer recurrence status of the subject may be at risk for cancer recurrence and/or the subject may be classified as a candidate for a subsequent cancer treatment.

In some embodiments, the cancer is any one of the types of cancer described elsewhere herein, e.g., colorectal cancer.

C. Therapies and Related Administration

In certain embodiments, the methods disclosed herein relate to identifying and administering customized therapies to patients given the status of a nucleic acid variant as being of somatic or germline origin. In some embodiments, essentially any cancer therapy (e.g., surgical therapy, radiation therapy, chemotherapy, and/or the like) may be included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In certain embodiments, the status of a nucleic acid variant from a sample from a subject as being of somatic or germline origin may be compared with a database of comparator results from a reference population to identify customized or targeted therapies for that subject. Typically, the reference population includes patients with the same cancer or disease type as the test subject and/or patients who are receiving, or who have received, the same therapy as the test subject. A customized or targeted therapy (or therapies) may be identified when the nucleic variant and the comparator results satisfy certain classification criteria (e.g., are a substantial or an approximate match).

In certain embodiments, the customized therapies described herein are typically administered parenterally (e.g., intravenously or subcutaneously). Pharmaceutical compositions containing an immunotherapeutic agent are typically administered intravenously. Certain therapeutic agents are administered orally. However, customized therapies (e.g., immunotherapeutic agents, etc.) may also be administered by methods such as, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

EXAMPLES

Example 1

A set of patients are analyzed here for cancer recurrence post their surgery. For this, from each patient a tumor tissue was collected during the surgery and a blood sample was obtained from the patient four weeks after the surgery. The genomic DNA is extracted from the tissue sample (first sample) and the cell-free DNA (second sample) is extracted from the blood sample. The DNA from the tissue sample is fragmented using fragmentase and cleaned to generate fragments of size 100-200 bp in average. Each sample (tissue DNA sample and cfDNA sample) of the patient undergoes the following steps: The sample is combined with methyl binding domain (MBD) buffers and magnetic beads conjugated with a MBDs protein and incubated overnight. Methylated DNA molecules (if present, in the sample) are bound by the MBD protein during this incubation. Non-methylated or less methylated DNA is washed away from the beads with buffers containing increasing concentrations of salt. Finally, a high salt buffer is used to wash the heavily methylated DNA away from the MBD protein. These washes result in three partitions (or three partitioned sets—hypo, intermediate and hyper) of increasingly methylated DNA. The partitioned DNA in the three partitioned sets are cleaned, to remove salt, and concentrated in preparation for the enzymatic steps of library preparation.

After concentrating the DNA in the partitioned sets, the end overhangs of partitioned DNA are extended, and adenosine residues are added to the 3' ends of fragments. The 5' end of each fragment is phosphorylated. These modifications make the partitioned DNA ligatable. DNA ligase and adapters are added to ligate each partitioned DNA molecule with an adapter on each end. These adapters contain non-unique barcodes and each partitioned set is ligated with adapters having non-unique barcodes that is distinguishable from the barcodes in the adapters used in the other partitioned sets. After ligation, the 3 partitioned sets are pooled together and are amplified by PCR.

Following PCR, amplified DNA is again cleaned and concentrated prior to enrichment. Once concentrated, the amplified DNA is combined with salt buffer and biotinylated RNA probes targeting specific regions of interest and the epigenetic-control nucleic acid molecules and this mixture is incubated overnight. The biotinylated RNA probes are captured by streptavidin magnetic beads and separated from the amplified DNA that was not captured by a series of salt washes, thereby enriching the sample. After enrichment, sample indices are incorporated to the enriched molecules via PCR amplification. After PCR amplification, the amplified molecules from different samples (within a batch) are pooled together and is sequenced using Illumina NovaSeq sequencer.

Figure 8:
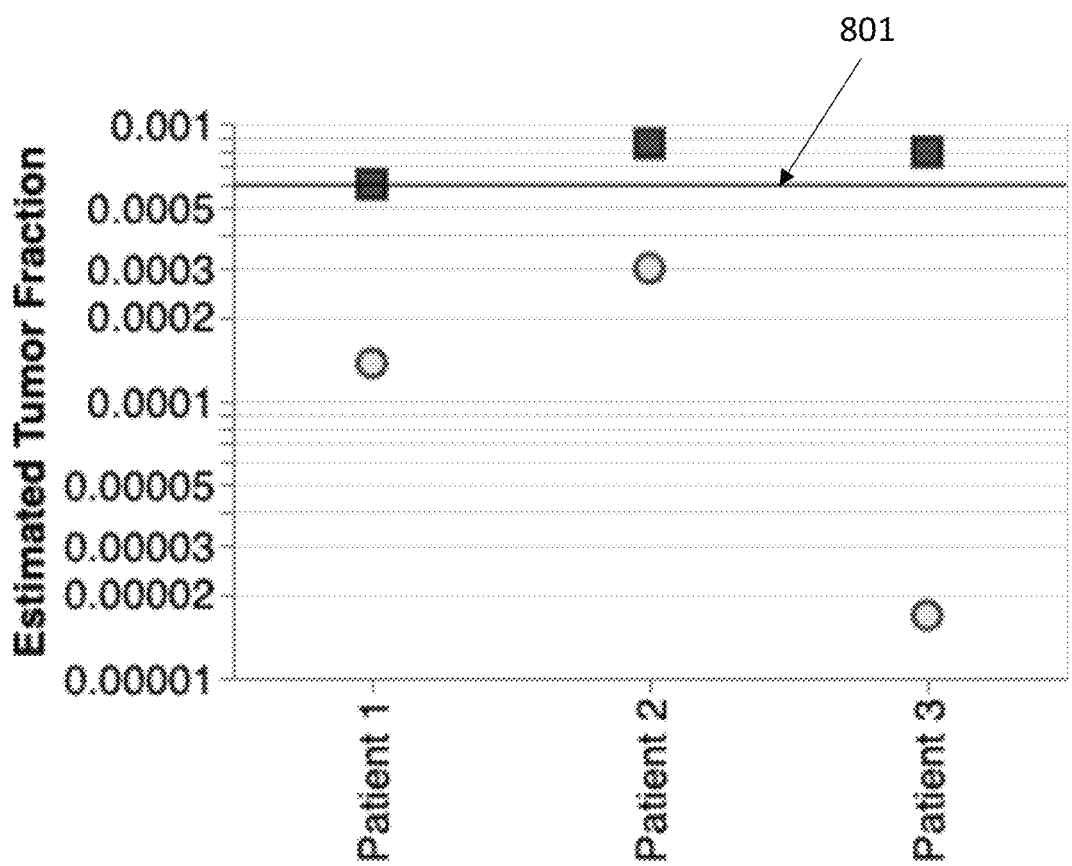
FIG. 8 is a graphical representation of most likely estimate of tumor fraction of three patients determined by analyzing cfDNA sample of the patients with or without using the information obtained from the respective tissue sample obtained during surgery. The circles represent the most likely estimate of tumor fraction determined by analyzing cfDNA sample in the absence of information obtained from a tissue sample and the squares represent the most likely estimate of tumor fraction determined by analyzing cfDNA utilizing the information obtained from a tissue sample. 801 shows the predetermined threshold (0.0006).

The sequence reads generated by the sequencer are then analyzed using bioinformatic tools/algorithms to generate methylation rates for each of the plurality of genomic regions of the tissue sample and cfDNA sample. To show that using information (e.g., methylation rate) obtained from the tissue sample enhances the tumor calling in cfDNA sample, three patients' cfDNA sample is analyzed in two scenarios. In scenario I, the sequence reads of the second sample from each of the three patients are analyzed without taking into account of the information obtained from the tissue sample. In this scenario, the likelihood of tumor fraction for each of the plurality of genomic regions is determined using the methylation rates of the plurality of genomic regions in the cfDNA sample, the partitioning information of the cfDNA molecules and the number of CG (Cytosine-Guanine) residues in the cfDNA molecules. The likelihood of tumor fraction for each of the plurality of genomic regions is then used to determine the overall posterior probability of cancer presence in the cfDNA sample. The overall posterior probability is then used to determine the most likely estimate of tumor fraction. All the three patients are classified as negative for ctDNA, as the most likely estimate tumor fraction of all the three patients (values shown as circles in FIG. 8) was below the predetermined threshold of 0.0006 (in this example) 801. In scenario II, the sequence reads of the second sample from each of the three patients are analyzed by taking into account of the information obtained from their corresponding tissue sample. In this scenario, the 25 genomic regions with highest methylation rates in the first sample (tissue sample) for each of the three patients are determined and only for those genomic regions, likelihood of tumor fraction is determined for their respective second sample using the methylation rates of the 25 genomic regions in the cfDNA sample, the partitioning information of the cfDNA molecules, the number of CG residues in the cfDNA molecules, and the methylation rates of the 25 genomic regions in the tissue sample. The likelihood of tumor fraction for the 25 genomic regions is then used to determine the overall posterior probability of cancer presence, which is in turn used to determine the most likely estimate of tumor fraction in the cfDNA sample. Here, the most likely estimate of tumor fraction of the cfDNA sample for the three patients (values shown as squares in FIG. 8) was above the predetermined threshold 801 and the patients are classified as positive for ctDNA. All these three patients eventually relapsed due to tumor recurrence. This clearly shows that upon using the information obtained from tissue sample, the signal from the tumor is enhanced and the sensitivity of the tumor calling in cfDNA sample is improved.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define the scope of the invention and that methods and structures within the scope of these claims and their equivalents be covered thereby.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

What is claimed is:

1. A method for detecting a presence or absence of cancer in a subject, comprising:
   a) obtaining at least one sample from the subject from at least two different time points to provide at least two samples, wherein a first sample of the at least two samples is obtained at a first time point of the at least two different time points and a second sample of the at least two samples is obtained at a second time point of the at least two different time points, wherein the first time point is prior to or during a cancer treatment and the second time point follows the cancer treatment, and wherein the subject is a human;
   b) processing polynucleotides from each of the at least two samples, wherein the processing comprises:
      i. partitioning at least a portion of the polynucleotides from the first sample into at least two partitions based on DNA methylation and optionally one or more additional epigenetic features, and partitioning at least a portion of the polynucleotides from the second sample into at least two partitions based on DNA methylation and optionally one or more additional epigenetic features, wherein a first partition from the first sample comprises hypomethylated DNA of the first sample, a first partition from the second sample comprises hypomethylated DNA of the second sample, a second partition from the first sample comprises hypermethylated DNA of the first sample, and a second partition from the second sample comprises hypermethylated DNA of the second sample, thereby generating partitioned polynucleotides;
      ii. tagging at least a portion of the partitioned polynucleotides from each of the first and second partitions from the first sample and each of the first and second partitions from the second sample, thereby generating tagged parent polynucleotides;
      iii. amplifying at least a portion of the tagged parent polynucleotides from each of the first and second partitions from the first sample and each of the first and second partitions from the second sample to generate progeny polynucleotides; and
      iv. sequencing at least a portion of the progeny polynucleotides generated from each of the first and second partitions from the first sample and each of the first and second partitions from the second sample to generate a set of sequencing reads; and
   c) analyzing a plurality of genomic regions for DNA methylation and optionally one or more additional epigenetic features from the set of sequencing reads of the at least two samples, to detect the presence or absence of the cancer in the subject at the second time point, wherein the plurality of genomic regions comprise differentially methylated regions that are perturbed by the cancer, the differentially methylated regions comprising hypomethylation variable target regions and/or hypermethylation variable target regions, and wherein the analyzing comprises
      i) mapping the set of sequencing reads to a reference sequence;
      ii) determining a plurality of epigenetic rates for the plurality of genomic regions of the at least two samples;
      iii) adjusting an epigenetic rate threshold based on the epigenetic rate of at least one of the plurality of genomic regions of the first sample; and
      iv) comparing the epigenetic rate for the plurality of genomic regions in the second sample with the adjusted epigenetic rate threshold to detect the presence or absence of the cancer; or
      i) mapping the set of sequencing reads to a reference sequence;
      ii) determining a plurality of epigenetic rates for the plurality of genomic regions of the first sample;
      iii) determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample;
      iv) combining the plurality of likelihoods for the one or more of the plurality of genomic regions to determine an overall posterior probability for the presence of the cancer in the subject; and
      v) comparing the overall posterior probability for the presence of the cancer in the subject with a predetermined threshold to detect the presence or absence of the cancer.

2. The method of claim 1, wherein the first sample is a polynucleotide sample extracted from a tumor tissue specimen, and wherein the second sample is a cell-free polynucleotide sample extracted from a blood sample.

3. The method of claim 1, wherein the first sample is a cell-free polynucleotide sample extracted from a blood sample, and wherein the second sample is a cell-free polynucleotide sample extracted from a blood sample.

4. The method of claim 1, wherein the analyzing comprises:
   i. mapping the set of sequencing reads to a reference sequence;
   ii. determining a plurality of epigenetic rates for the plurality of genomic regions of the first sample;
   iii. determining a likelihood of a tumor fraction for one or more of the plurality of genomic regions in the second sample based on a predetermined set of epigenetic rates of the plurality of genomic regions of the second sample, a set of epigenetic characteristics for a set of cell-free polynucleotides in the second sample mapped to the plurality of genomic regions, and the epigenetic rates of the plurality of genomic regions of the first sample;
   iv. combining the plurality of likelihoods for the one or more of the plurality of genomic regions to determine an overall posterior probability for the presence of the cancer in the subject; and
   v. comparing the overall posterior probability for the presence of the cancer in the subject with a predetermined threshold to detect the presence or absence of the cancer.

5. The method of claim 4, further comprising
   vi. classifying the subject (a) as positive for circulating tumor DNA (ctDNA), if the overall posterior probability for the presence of the cancer in the subject is greater than the predetermined threshold, or (b) as negative for ctDNA, if the overall posterior probability for the presence of the cancer in the subject is less than the predetermined threshold.

6. The method of claim 1, further comprising analyzing the plurality of genomic regions from the set of sequencing reads of the at least two samples to detect the presence of at least one somatic variation in the second sample.

7. The method of claim 6, wherein the at least one somatic variation comprises a single nucleotide variation (SNV), insertion or deletion (indel), copy number variation (CNV), gene fusion, or combination thereof.

8. The method of claim 7, further comprising:
   vi. classifying the subject (a) as positive for circulating tumor DNA (ctDNA), if the overall posterior probability for the presence of the cancer in the subject is greater than or equal to the predetermined threshold or the presence of the at least one somatic variation is detected in the second sample, or (b) as negative for ctDNA, if the overall posterior probability for the presence of the cancer in the subject is less than the predetermined threshold and the presence of the at least one somatic variation is not detected in the second sample.

9. The method of claim 1, wherein the at least one epigenetic rate comprises a methylation rate.

10. The method of claim 1, wherein the one or more of the plurality of genomic regions comprise genomic regions with 50 highest epigenetic rates in the first sample.

11. The method of claim 1, wherein the one or more of the plurality of genomic regions comprise genomic regions with at least 250 highest epigenetic rates in the first sample.

12. The method of claim 1, wherein each of the plurality of genomic regions comprise at least 50 bp.

13. The method of claim 1, wherein the analyzing comprises:
   i) mapping the set of sequencing reads to a reference sequence;
   ii) determining a plurality of epigenetic rates for the plurality of genomic regions of the at least two samples;
   iii) adjusting an epigenetic rate threshold based on the epigenetic rate of at least one of the plurality of genomic regions of the first sample; and
   iv) comparing the epigenetic rate for the plurality of genomic regions in the second sample with the adjusted epigenetic rate threshold to detect the presence or absence of the cancer.

14. The method of claim 13, further comprising classifying the subject (a) as positive for circulating tumor DNA (ctDNA), if the epigenetic rate of at least one of the plurality of genomic regions of the second sample is greater than or equal to the adjusted epigenetic rate threshold, or (b) as negative for ctDNA, if the epigenetic rates of the plurality of genomic regions of the second sample are all less than the adjusted epigenetic rate threshold.

15. The method of claim 7, further comprising:
   vi. classifying the subject (a) as positive for circulating tumor DNA (ctDNA), if the epigenetic rate of at least one of the plurality of genomic regions of the second sample is greater than or equal to the adjusted epigenetic rate threshold or the presence of the at least one somatic variation is detected in the second sample, or (b) as negative for ctDNA, if the epigenetic rates of the plurality of genomic regions of the second sample are all less than the adjusted epigenetic rate threshold and the presence of the at least one somatic variation is not detected in the second sample.

* * * * *